(12) United States Patent
Ishii et al.

(10) Patent No.: US 9,644,028 B2
(45) Date of Patent: May 9, 2017

(54) ANTI-CDH3 HUMANIZED ANTIBODY, DRUG CONJUGATE THEREOF, AND USE THEREOF

(71) Applicant: PERSEUS PROTEOMICS INC., Tokyo (JP)

(72) Inventors: Keisuke Ishii, Tokyo (JP); Katsuyuki Mitomo, Tokyo (JP); Katsushi Kouda, Tokyo (JP); Fumiko Nomura, Tokyo (JP); Yoko Kayukawa, Tokyo (JP); Tadashi Matsuura, Tokyo (JP)

(73) Assignee: PERSEUS PROTEOMICS INC., Tokyo (JP)

( * ) Notice: Subject to any disclaimer, the term of this patent is extended or adjusted under 35 U.S.C. 154(b) by 0 days.

(21) Appl. No.: 14/768,151

(22) PCT Filed: Feb. 14, 2014

(86) PCT No.: PCT/JP2014/053473
§ 371 (c)(1),
(2) Date: Aug. 14, 2015

(87) PCT Pub. No.: WO2014/126198
PCT Pub. Date: Aug. 21, 2014

(65) Prior Publication Data
US 2016/0152703 A1    Jun. 2, 2016

(30) Foreign Application Priority Data

Feb. 15, 2013 (JP) ................................. 2013-027386
Apr. 24, 2013 (JP) ................................. 2013-091163

(51) Int. Cl.
*A61K 39/395* (2006.01)
*C07K 16/28* (2006.01)
*A61K 47/48* (2006.01)

(52) U.S. Cl.
CPC ........ *C07K 16/28* (2013.01); *A61K 47/48384* (2013.01); *A61K 47/48561* (2013.01); *A61K 47/48715* (2013.01); *C07K 2317/24* (2013.01); *C07K 2317/56* (2013.01); *C07K 2317/565* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,208,020 A | 5/1993 | Chari et al. | |
| 5,821,337 A | 10/1998 | Carter et al. | |
| 6,180,370 B1 | 1/2001 | Queen et al. | |
| 6,333,410 B1 | 12/2001 | Chari et al. | |
| 2002/0082396 A1 | 6/2002 | Matsushima et al. | |
| 2012/0136140 A1 | 5/2012 | Aburatani et al. | |
| 2013/0071324 A1 | 3/2013 | Hino et al. | |
| 2013/0317201 A1 | 11/2013 | Ishii et al. | |
| 2014/0221620 A1 | 8/2014 | Zhang et al. | |

FOREIGN PATENT DOCUMENTS

| | | |
|---|---|---|
| CN | 102124344 A | 7/2011 |
| CN | 102753579 A | 10/2012 |
| EP | 0 239 400 A2 | 9/1987 |
| EP | 2634194 A1 | 9/2013 |
| EP | 2 848 686 A1 | 3/2015 |
| JP | 2005-169 A | 1/2005 |
| JP | 2008-516896 A | 5/2008 |
| JP | 4836147 B2 | 12/2011 |
| WO | WO 96/02576 A1 | 2/1996 |
| WO | WO 02/097395 A2 | 12/2002 |
| WO | WO 2006/034488 A2 | 3/2006 |
| WO | WO 2007/102525 A1 | 9/2007 |
| WO | WO 2010/001585 A1 | 1/2010 |
| WO | WO 2010/126137 A1 | 11/2010 |
| WO | WO 2011/080796 A1 | 7/2011 |
| WO | WO 2011/099524 A1 | 8/2011 |
| WO | WO 2011-526583 A | 10/2011 |
| WO | WO 2012/057315 A1 | 5/2012 |
| WO | WO 2012/057328 A1 | 5/2012 |
| WO | WO 2012/176765 A1 | 12/2012 |
| WO | WO 2013/150623 A1 | 10/2013 |

OTHER PUBLICATIONS

Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Barbas III et al., "Phage Display, A Laboratory Manual," Protocol 9.5, Cold Spring Harbor Laboratory Press, 2001, pp. 9.52-9.65 (Total 8 pages).

(Continued)

*Primary Examiner* — Sheela J Huff
(74) *Attorney, Agent, or Firm* — Birch, Stewart, Kolasch & Birch, LLP

(57) ABSTRACT

The present invention provides an anti-CDH3 humanized antibody having lower immunogenicity, and an anti-CDH3 humanized antibody drug conjugate having the aforementioned anti-CDH3 humanized antibody. The present invention provides a conjugate of an anti-CDH3 humanized antibody and a drug by conjugating a drug having cytotoxicity to an anti-CDH3 humanized antibody having complementarity determining region sequences derived from the heavy chain variable region of an antibody produced by cells having Accession No. NITE BP-1536, and complementarity determining region sequences derived from the light chain variable region thereof, and which also comprises a heavy chain human subgroup III consensus framework sequence or a human germline sequence selected under optimal alignment as a framework region sequence of the heavy chain variable region, and a light chain human κ subgroup I consensus framework sequence or a human germline sequence selected under optimal alignment as a framework region sequence of the light chain variable region.

36 Claims, 16 Drawing Sheets
(5 of 16 Drawing Sheet(s) Filed in Color)

(56) References Cited

OTHER PUBLICATIONS

Carter et al., "Humanization of an Anti-p185HER2 Antibody for Human Cancer Therapy," Proc. Natl. Acad. Sci. USA, Immunology, vol. 89, May 1992, pp. 4285-4289.

Chari et al., "Immunoconjugates Containing Novel Maytansinoids: Promising Anticancer Drugs," Cancer Research, vol. 52, Jan. 1, 1992, pp. 127-131.

Chothia et al., "Canonical Structures for the Hypervariable Regions of Immunoglobulins," J. Mol. Biol., vol. 196, 1987, pp. 901-917.

Du et al., "Differential Cellular Internalization of Anti-CD19 and CD22 Immunotoxins Results in Different Cytotoxic Activity," Cancer Res., vol. 68, No. 15, Aug. 1, 2008, pp. 1-17.

Gough, "Rapid and Quantitative Preparation of Cytoplasmic RNA from Small Number of Cells," Analytical Biochemistry, vol. 173, 1988, pp. 93-95.

International Preliminary Report on Patentability and Written Opinion of the International Searching Authority (forms PCT/IB/373, PCT/ISA/237 and PCT/IB/338), issued Aug. 27, 2015, for International Application No. PCT/JP2014/053473, along with English translations.

International Search Report (form PCT/ISA/210), issued Mar. 18, 2014, for International Application No. PCT/JP2014/053473.

Junutula et al., "Site-specific Conjugation of a Cytotoxic Drug to an Antibody Improves the Therapeutic Index," Nature Biotechnology, vol. 26, No. 8, Aug. 2008 (Published Online Jul. 20, 2008), pp. 925-932.

Kabat et al., "Sequences of Proteins of Immunological Interest," vol. 1, Fifth Edition, Public Health Service, National Institutes of Health, Bethesda, USA, 1991, pp. 103-108 and 324-331.

Lewis Phillips et al., "Targeting HER2-Positive Breast Cancer with Trastuzumab-DM1, an Antibody-Cytotoxic Drug Conjugate," Cancer Res. vol. 68, No. 22, Nov. 15, 2008, pp. 9280-9290 (Total 11 pages).

Riechmann et al., "Reshaping Human Antibodies for Therapy," Nature, vol. 332, Mar. 24, 1988, pp. 323-327.

Shulman et al., "A Better Cell Line for Making Hybridomas Secreting Specific Antibodies," Nature, vol. 276, No. 5685, Nov. 16,1978, pp. 269-270 (Total 5 pages).

Sims et al., "A Humanized CD18 Antibody Can Block Function without Cell Destruction," The Journal of Immunology, vol. 151, No. 4, Aug. 15, 1993, pp. 2296-2308.

Singh et al., "Antibody-Cytotoxic Agent Conjugates: Preparation and Characterization," Therapeutic Antibodies: Methods and Protocols, vol. 525, 2009, pp. 445-467.

Stephan et al., "Anti-CD22-MCC-DM1 and MC-MMAF Conjugates: Impact of Assay Format on Pharmacokinetic Parameters Determination," Bioconjugate Chem., vol. 19, No. 8, 2008 (Published on Web Jul. 19, 2008), pp. 1673-1683.

Tan et al., "Superhumanized Antibodies: Reduction of Immunogenic Potential by Complementarity-Determining Region Grafting with Human Germline Sequences: Application to an Anti-CD28," The Journal of Immunology, 2002, vol. 169, pp. 1119-1125.

Tempest et al., "Reshaping a Human Monoclonal Antibody to Inhibit Human Respiratory Syncytial Virus Infection in Vivo," Bio/Technology, vol. 9, No. 3, Mar. 1991, pp. 266-271 (Total 9 pages).

Urlaub et al., "Effect of Gamma Rays at the Dihydrofolate Reductase Locus: Deletions and Inversions," Somatic Cell and Molecular Genetics, vol. 12, No. 6, 1986, pp. 555-566.

Verma et al., "Trastuzumab Emtansine for HER2-Positive Advanced Breast Cancer," The New England Journal of Medicine, vol. 367, No. 19, Nov. 8, 2012, pp. 1783-1791.

Widdison et al., "Semisynthetic Maytansine Analogues for the Targeted Treatment of Cancer," J. Med. Chem., vol. 49, No. 14, 2006 (Published on Web Jun. 10, 2006), pp. 4392-4408.

Yoshida et al., "Teratocarcinoma Cell Adhesion: Identification of a Cell-Surface Protein Involved in Calcium-Dependent Cell Aggregation," Cell, vol. 28, Feb. 1982, pp. 217-224.

Zhang et al., "PF-03732010: A Fully Human Monoclonal Antibody against P-Cadherin with Antitumor and Antimetastatic Activity," Cancer Therapy: Preclinical, Clinical Cancer Research, vol. 16, No. 21, Nov. 1, 2010 (Published Online First Sep. 9, 2010), pp. 5177-5188 (Total 13 pages).

Extended European Search Report issued in European Patent Application No. 14751339.4 on Sep. 5, 2016.

Chinese Office Action and Search Report, issued Nov. 2, 2016, for Chinese Application No. 201480009141.8, with an English translation of the Chinese Office Action.

* cited by examiner

Figure 1
A:
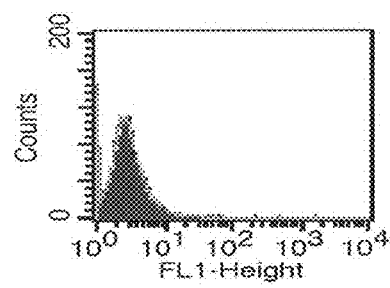
CHO
B:
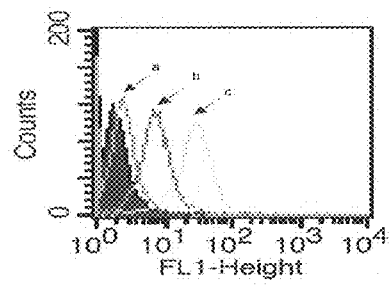
CHO that forcibly expresses CDH3
C:
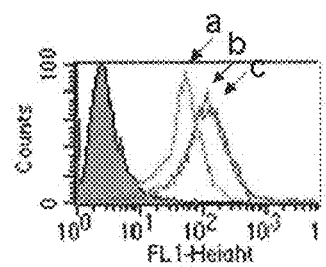
NCI-H358

Figure 2
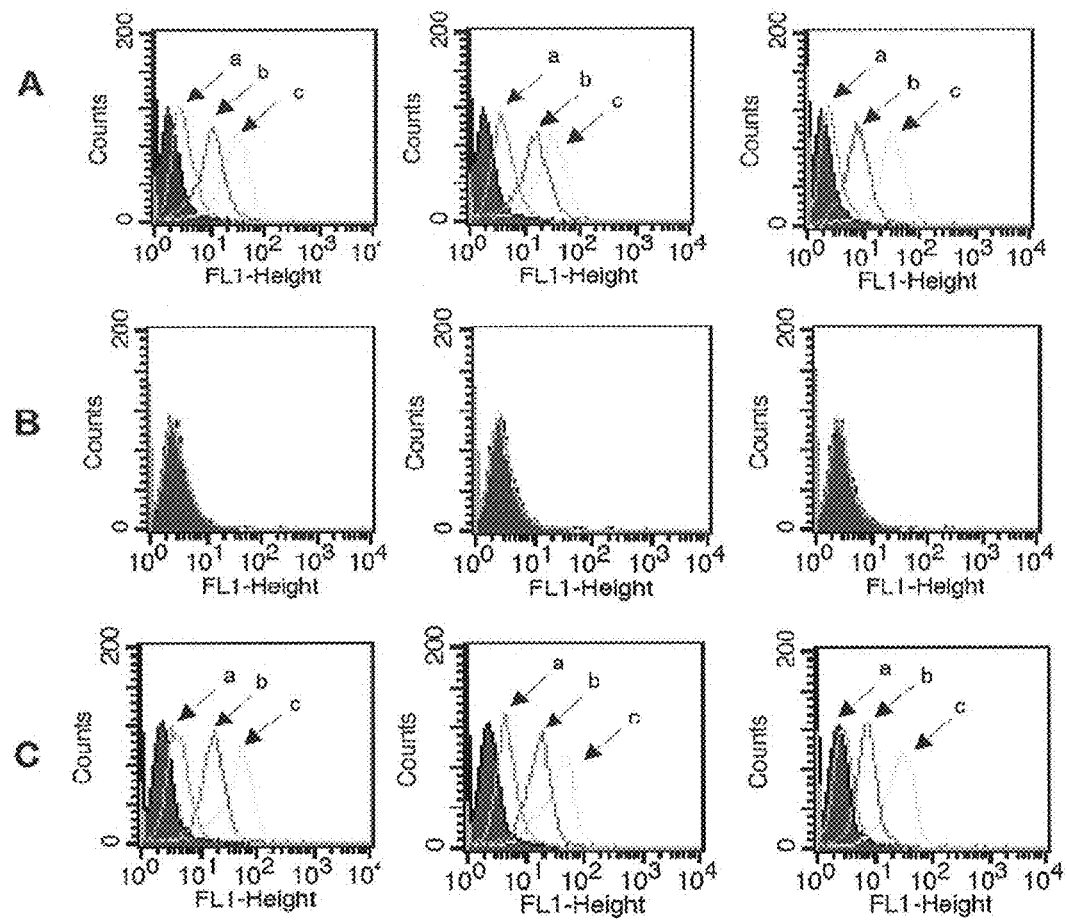
D: Mouse antibody (PPAT-076-44M) derived from Accession No. NITE BP-1536
CHO that forcibly expresses DH3  CHO     NCI-H358
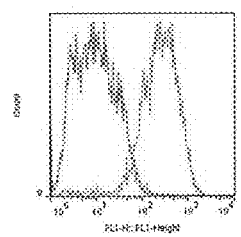 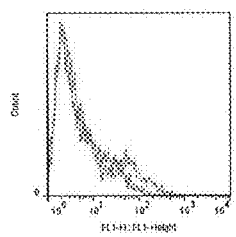 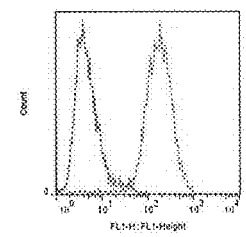

A

B

C

Figure 5
A: NCI-H358
PPAT-076-44C     PPAT-076-44Ha     PPAT-076-44Hb
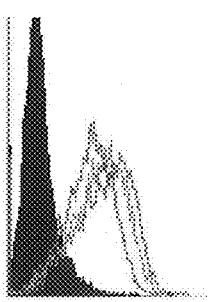 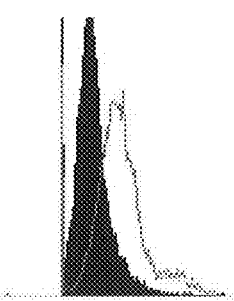 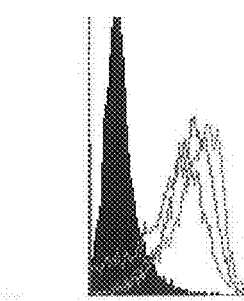
PPAT-076-44Hc     PPAT-076-44Hd
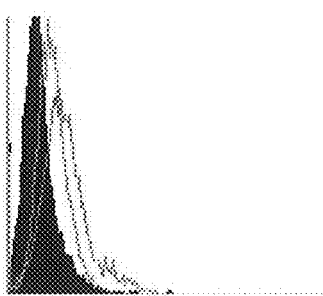 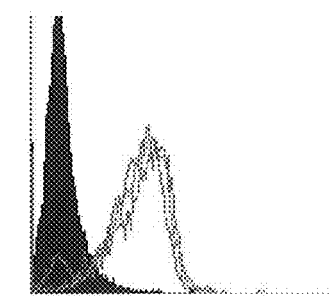
B: CHO cells
PPAT-076-44C     PPAT-076-44Hb     PPAT-076-44Hd
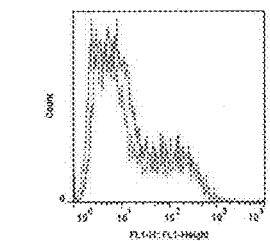 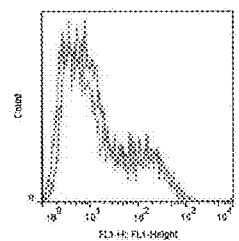 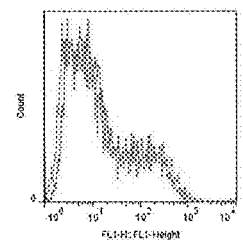
C: Cells that forcibly express CDH3
PPAT-076-44C     PPAT-076-44Hb     PPAT-076-44Hd
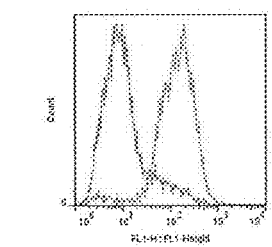 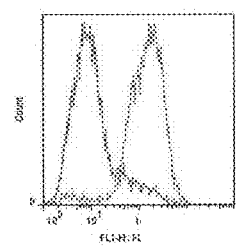 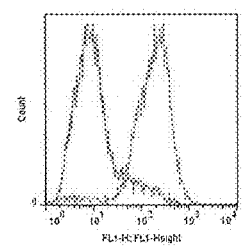

Figure 7
A: NCI-H358
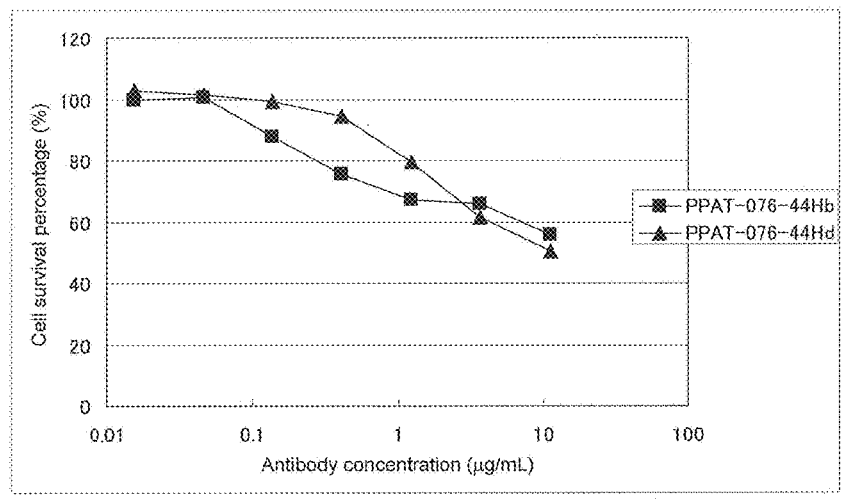
B: HCC-1954
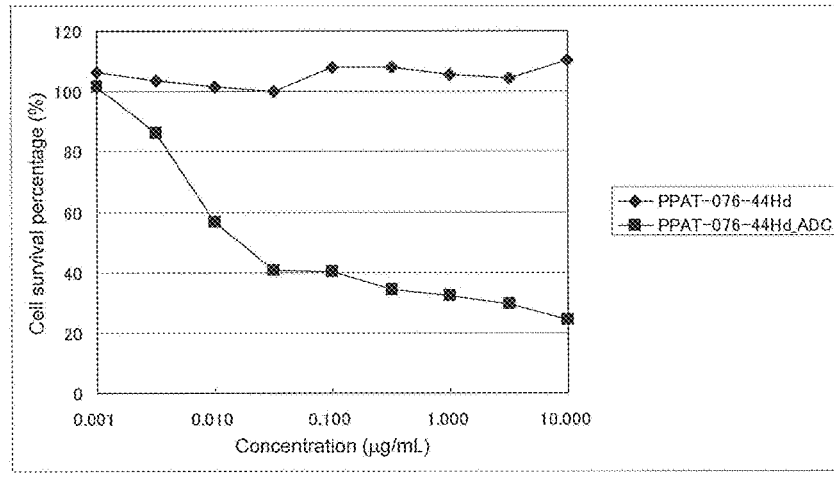

Figure 7
C: HCC70
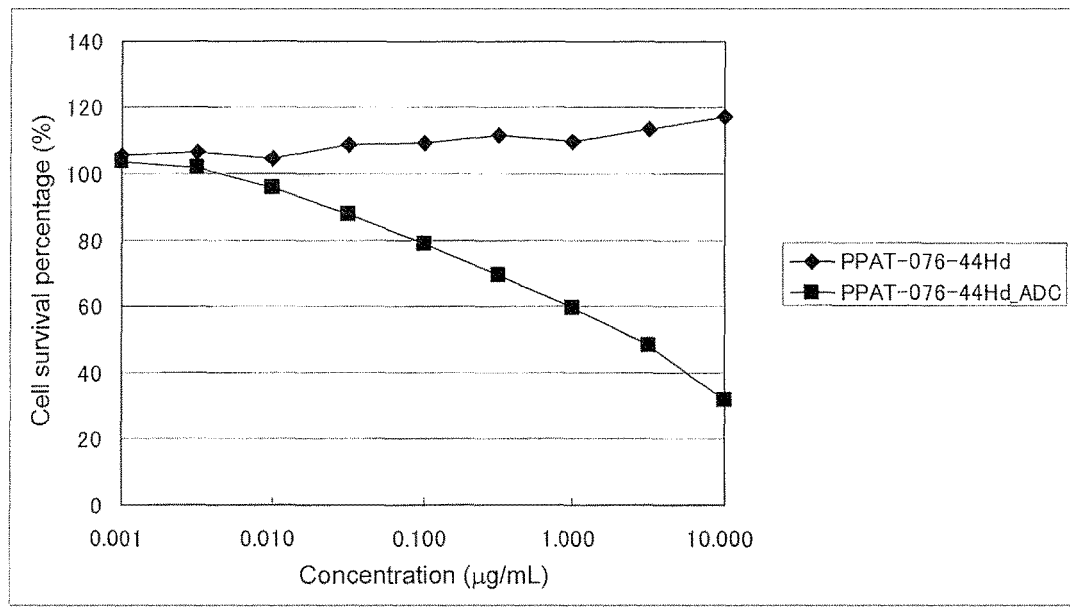
D: Individual cancer cell lines
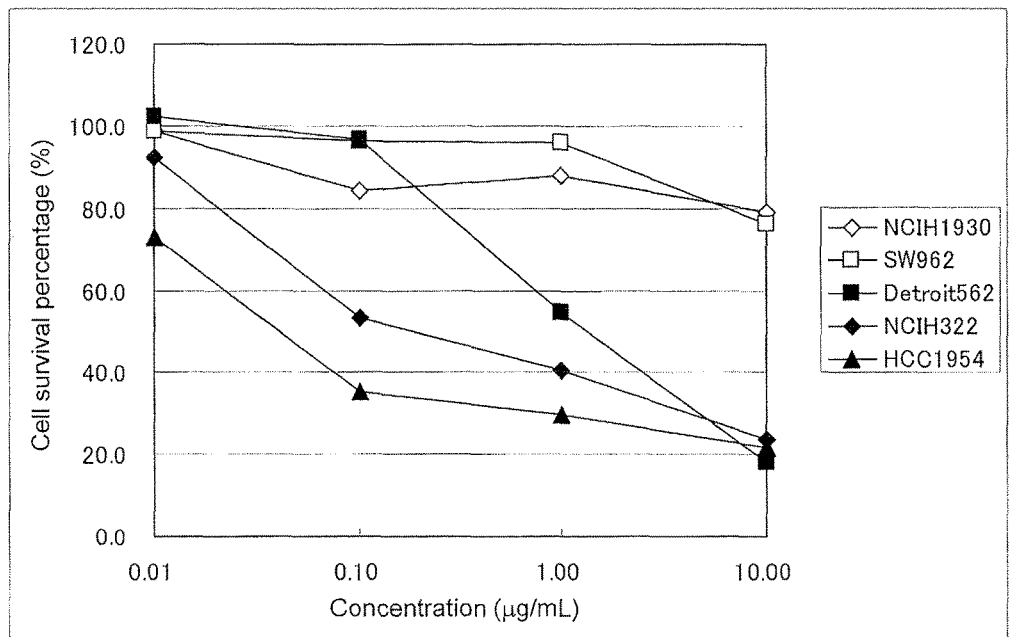

HCC1954

HCC70

HCC70

Oka-C-1

Figure 15
A: PPAT-076-44Hb
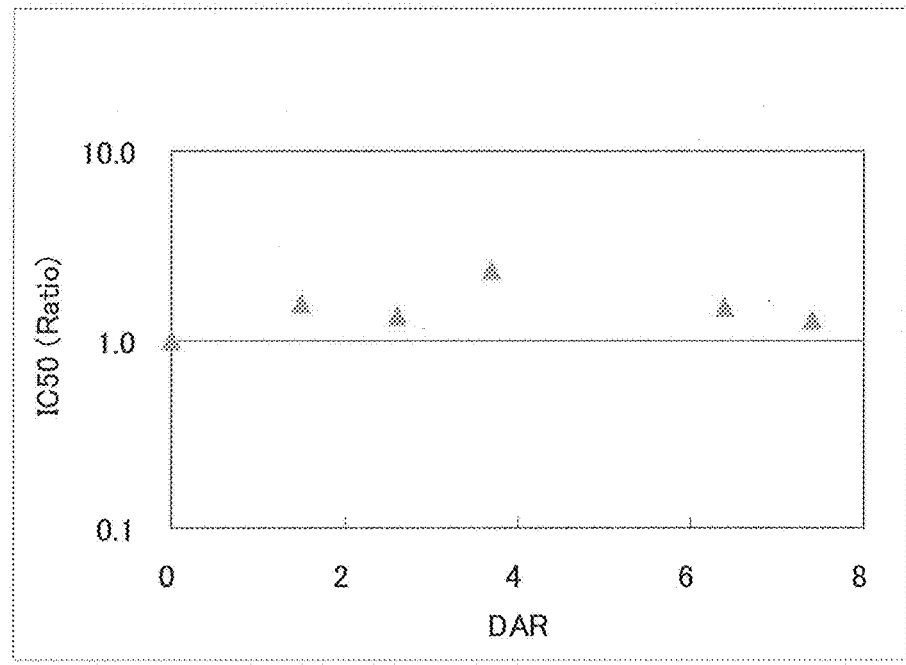
B: PPAT-076-44Hd
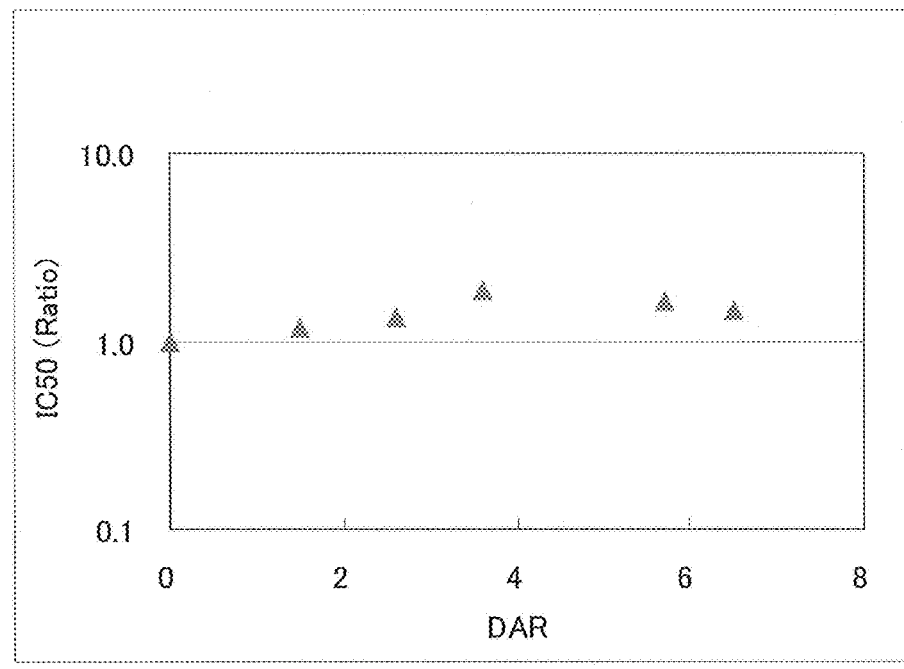

Figure 16
A: HCC1954
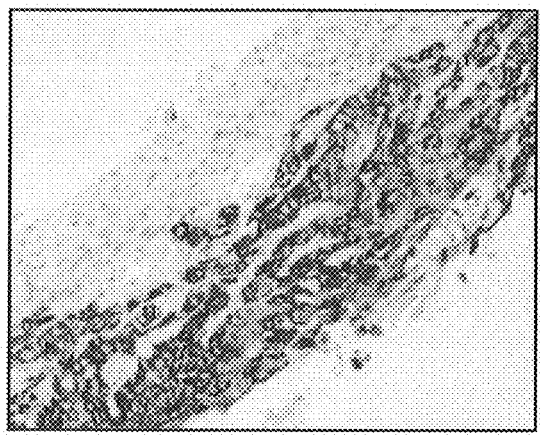
B: HCC70
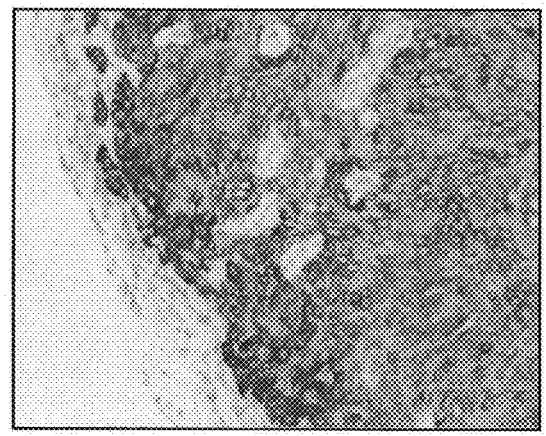
C: Oka-C-1
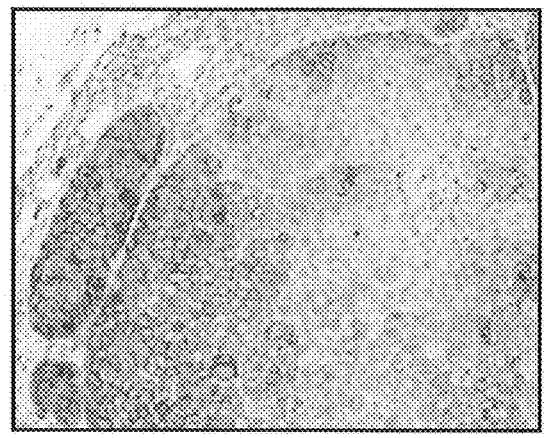

ANTI-CDH3 HUMANIZED ANTIBODY, DRUG CONJUGATE THEREOF, AND USE THEREOF

REFERENCE TO SEQUENCE LISTING SUBMITTED VIA EFS-WEB

This application includes an electronically submitted sequence listing in .txt format. The .txt file contains a sequence listing entitled "2015-11-30 2870-0617PUS1 ST25.txt" created on Nov. 30, 2015 and is 54,223 bytes in size. The sequence listing contained in this .txt file is part of the specification and is hereby incorporated by reference herein in its entirety.

TECHNICAL FIELD

The present invention relates to an anti-CDH3 humanized antibody and an immune complex thereof, and particularly to a drug conjugate thereof. Moreover, the present invention relates to a method of using an anti-CDH3 humanized antibody and an immune complex thereof.

BACKGROUND ART

Cancer is a serious disease that accounts for a major cause of death. However, therapeutic needs therefor have not yet been met. In recent years, in order to overcome the problem of conventional chemotherapy that causes damage even to normal cells, studies have been intensively conducted regarding cancer therapy using molecularly targeted drugs, in which a drug targeting a specific molecule that is expressed specifically in a cancer cell is designed, and the therapy is then carried out using the drug.

As one of the targets, CDH3 (P-cadherin) which is a cell membrane surface antigen has been identified. CDH3 is a membrane protein that has been discovered as a molecule that is calcium-dependently associated with hemophilic cell adhesion (Yoshida and Takeichi, Cell 28: 217-224, 1982 (Non Patent Literature 1)). A protein, which has cadherin repeats consisting of approximately 110 amino acid residues having high homology to one another, is referred to as a "cadherin superfamily," and CDH3 is a main member of the cadherin superfamily.

An increase in the expression of CDH3 in certain types of cancer cells has been reported. Thus, cancer therapy has been studied in which an antibody is used on cancer cells having higher expression of CDH3 in cancer tissues than in normal tissues (WO 2002/097395 (Patent Literature 1), WO 2007/102525 (Patent Literature 2), JP Patent Publication (Kohyo) No. 2011-526583 A (Patent Literature 4), and WO 2011/080796 A1 (Patent Literature 5)).

A large number of molecular-targeted drugs, which target a specific antigen as mentioned above, have already been placed on the market as antibody drugs, and a majority of the drugs have antibody-dependent cellular cytotoxicity (ADCC; Antibody Dependent Cellular Cytotoxicity) as a principal mode of action. However, their drug effects are not necessarily sufficient, and thus, technology development is proceeding towards the achievement of a stronger anticancer effect.

An effective means for enhancing the anticancer ability of an antibody is the binding of the antibody to a substance having strong toxicity (toxin). If toxin alone were administered to a patient, it would also affect normal tissues, and thereby, it could not be an effective therapeutic means. However, as a result of the binding of the toxin to an antibody that binds to a cancer cell-specific antigen, the toxin is able to achieve a capacity of killing only cancer cells, while it does not affect normal tissues. Such a drug is referred to as an antibody drug conjugate (ADC; Antibody Drug Conjugate). That is to say, a toxin shows no toxicity in a state in which it binds to an antibody. However, when a certain type of antibody binds to a cell that expresses a target antigen, it is incorporated into the cell and is then decomposed by a lysosome. Accordingly, the certain type of antibody, to which a toxin binds, is incorporated into the cell, and it is then decomposed therein, so that the toxin is released. As a result, the toxin is expressed only in a specific cell, and the cell is then killed by the effect thereof.

Examples of a drug ingredient used in ADC include bacterial protein toxins such as diphtheria toxin, vegetable protein toxins such as ricin, and low-molecular-weight toxins such as an auristatin, a maytansinoid or a calicheamicin and the derivatives thereof.

In ADC, a drug that is bound to an antibody circulates in the blood and then accumulates in a target tumor, and thereafter, it exhibits its drug effects. The release of a drug in sites other than tumor sites (the release from the antibody) is not necessarily preferable because it is likely to cause side effects. That is, a drug that is bound to an antibody is preferably designed such that it is removed from the antibody after it has been incorporated into a cell.

In recent years, from the aforementioned viewpoint, a drug (developed drug name: T-DM1), in which a toxin is bound, via a non-cleavable linker (SMCC), to trastuzumab that had already been commercially available as a therapeutic agent for breast cancer, has been developed by Genentech, and extremely high clinical effects have been obtained (N. Engl. J. Med. 2012 Nov 8; 367 (19): 1783-91 (Non Patent Literature 2)). In addition, an antibody drug conjugate, in which an antibody is bound to a drug component via a cleavable linker, has also been developed. For example, the development of an antibody drug conjugate, in which a drug is bound to a HuN901 antibody via a cleavable linker (SPP), that targets diseases expressing NCAM antigen, has been promoted by Immunogen.

Moreover, an agent for radioimmunotherapy, in which a radioactive material is bound to an antibody and the thus obtained antibody is subjected to the radioimmunotherapy, has also been developed. As a drug formed by binding a radioactive material 90Y (yttrium) or 111In (indium) to a chimeric anti-CD20 antibody, zevalin (common name: ibritumomab tiuxetan) has been placed on the market.

When the present antibody is used in the form of a drug conjugate or the like, and in particular, when the antibody is administered to a patient for a long period of time, the immunogenicity of the antibody to be administered that may generate an antibody against a heterologous immunoglobulin (e.g., a human anti-mouse antibody (HAMA)) is desirably a minimum or nothing. It is advantageous to produce a drug conjugate using such an antibody.

As a means for obtaining such an antibody, for example, a technique of producing a humanized antibody by combining the complementarity determining region (CDR) obtained from a heterologous organism such as a mouse with the framework region (FR) of an antibody derived from a human has been commonly used by a person skilled in the art (JP Patent Publication (Kokai) No. 2005-000169 A (Patent Literature 12), and Japanese Patent No. 4836147 (Patent Literature 13)). However, when inappropriate FR is combined with CDR, undesirable results such as the disappearance of affinity and a decrease in stability are frequently obtained. To cope with such phenomena, a method called "reshape," which comprises substituting amino acid residues derived from the antibody serving as a transplant donor with amino acid residues in the corresponding positions in the framework region, has been carried out. If appropriate substitutions were carried out, a reduction in affinity possibly caused by humanization could be improved (Nature; 332, p. 323 (1988) (Non Patent Literature 3), and U. S. Patent No. 6180370 (Patent Literature 3)).

Hence, the CDR sequence derived from a heterologous organism such as a mouse and the FR sequence derived from a human, which are used in the present humanized antibody, are preferably 100% identical to their original amino acid sequences. However, substitution of amino acid residues is commonly carried out for the purpose of maintaining the binding of an antibody to an antigen in the process of humanization and chimerization. For the purpose of maintaining affinity, it is also preferable to add a genetic modification to an antibody within a range in which the binding ability of the antibody to CDH3 is maintained and the immunogenicity thereof is not extremely increased. The sequence consisting of CDR and FR, which are combined for humanization, shows a sequence homology of at least 90%, 91%, 92%, 93%, 94%, 95%, 96%, 97%, 98%, 99% or more, with the original sequence, or it is 100% identical to the original sequence. The antibody comprising such a partially modified sequence is considered to be an antibody that maintains the properties of CDR derived from the original hybridoma in the sense that it specifically binds to a specific epitope of CDH3.

Using the thus obtained humanized antibody, the immunogenicity of the antibody is kept to the minimum, and further, an immune complex comprising the humanized antibody, which has a strong cytotoxicity such as ADC, is provided for the treatment of diseases. This clearly benefits patients whom the drug is administered to. Moreover, in the present technical field, there is a further demand for drugs used to treat various cancers such as lung cancer, colon cancer and breast cancer. An example of such a drug that is particularly useful for this purpose is an anti-CDH3 humanized antibody drug conjugate, which has significantly low toxicity but has advantageous therapeutic effectiveness.

PRIOR ART LITERATURES

Patent Literature

Patent Literature 1: WO 2002/097395
Patent Literature 2: WO 2007/102525
Patent Literature 3: U.S. Pat. No. 6,180,370
Patent Literature 4: JP Patent Publication (Kohyo) No. 2011-526583 A
Patent Literature 5: WO 2011/080796 A1
Patent Literature 6: WO 2013/150623
Patent Literature 7: EP239400
Patent Literature 8: WO 96/02576
Patent Literature 9: JP Patent Publication (Kohyo) No. 2008-516896 A
Patent Literature 10: U.S. Pat. No. 5,208,020
Patent Literature 11: U.S. Pat. No. 6,333,410 B1
Patent Literature 12: JP Patent Publication (Kokai) No.2005-000169 A
Patent Literature 13: Japanese Patent No. 4836147

Non Patent Literature

Non Patent Literature 1: Yoshida and Takeichi, Cell 28: 217-224, 1982
Non Patent Literature 2: N. Engl. J. Med. 2012 Nov. 8; 367(19): 1783-91
Non Patent Literature 3: Nature; 332, p. 323 (1988)
Non Patent Literature 4: Somat. Cell. Mol. Genet; 12, p. 5555 (1986)
Non Patent Literature 5: Nature; 276, p. 269 (1978)
Non Patent Literature 6: Cancer Res.; 68(22), p. 9280 (2008)
Non Patent Literature 7: Nature Biotechnology; 26(8), p. 925 (2008)
Non Patent Literature 8: Bio Conjugate Chemistry; 19, p. 1673 (2008)
Non Patent Literature 9: Cancer Res.; 68(15), p. 6300 (2008)
Non Patent Literature 10: Analytical Biochemisty; 173, p. 93 (1988)
Non Patent Literature 11: "Phage Display - A Laboratory Manual -" PROTOCOL 9.5
Non Patent Literature 12: J. Med. Chem.; 49, p. 4392 (2006)
Non Patent Literature 13: Cancer Res.; 52, p. 127 (1992)
Non Patent Literature 14: Journal of Immunology; 169, p. 1119 (2002)
Non Patent Literature 15: Sequences of proteins of immunological interest, 5th Ed.,
Public Health Service, National Institutes of Health, Bethesda, MD (1991)
Non Patent Literature 16: J. Mol Biol.; 196, p. 901 (1987)
Non Patent Literature 17: J. Immunol.; 151, p. 2296 (1993)
Non Patent Literature 18: J. Mol. Biol.; 196: p. 901 (1987))
Non Patent Literature 19: Biotechnology; 9, p. 266 (1991)
Non Patent Literature 20: Proc. Natl. Acad. Sci. USA; 89, p. 4285 (1992)
Non Patent Literature 21: Methods. Mol. Biol.; 525, p. 445 (2009)

SUMMARY OF INVENTION

Object to be Solved by the Invention

It is an object of the present invention to produce an anti-CDH3 humanized antibody having lower immunogenicity, and to provide an anti-CDH3 humanized antibody drug conjugate comprising the aforementioned anti-CDH3 humanized antibody that more efficiently kills cancer cells expressing CDH3.

Means for Solving the Object

As a result of intensive studies directed towards achieving the aforementioned object, the present inventors have combined the CDR sequences of an antibody specifically recognizing CDH3 with various human-derived FR sequences, and have introduced appropriate amino acid mutations therein to improve affinity, so that the inventors have produced an anti-CDH3 humanized antibody having low immunogenicity. Thereafter, using this anti-CDH3 humanized antibody, the present inventors have succeeded in producing an anti-CDH3 humanized antibody drug conjugate that more efficiently kills cancer cells expressing CDH3, thereby completing the present invention.

The present invention provides an anti-CDH3 humanized antibody, which comprises complementarity determining region sequences (CDR-H1, H2, and H3) derived from the heavy chain variable region of an antibody produced by cells having Accession No. NITE BP-1536 (hereinafter this mouse antibody is referred to as antibody number: PPAT-076-44M), and complementarity determining region sequences (CDR-L1, L2, and L3) derived from the light chain variable region thereof, and which also comprises the consensus framework residues of human heavy chain subgroup III and the consensus framework residues of human light chain κ subgroup I.

The present invention further provides an anti-CDH3 humanized antibody, which comprises the complementarity determining region sequences (CDR-H1, H2, and H3) of the heavy chain variable region that are shown in SEQ ID NO: 56, SEQ ID NO: 57, and SEQ ID NO: 58 respectively, and the complementarity determining region sequences (CDR-L1, L2, and L3) of the light chain variable region that are shown in SEQ ID NO: 59, SEQ ID NO: 60, and SEQ ID NO: 61 respectively, and which also comprises the consensus framework residues of human heavy chain subgroup III and the consensus framework residues of human light chain κ subgroup I.

The present invention further provides an anti-CDH3 humanized antibody, which comprises complementarity determining region sequences (CDR-H1, H2, and H3) derived from the heavy chain variable region of an antibody produced by cells having Accession No. NITE BP-1536, and complementarity determining region sequences (CDR-L1, L2, and L3) derived from the light chain variable region thereof, and which also comprises framework region sequences that are derived from a human germline and are selected under optimal alignment.

The present invention further provides an anti-CDH3 humanized antibody, which comprises the complementarity determining region sequences (CDR-H1, H2, and H3) of the heavy chain variable region that are shown in SEQ ID NO: 56, SEQ ID NO: 57, and SEQ ID NO: 58 respectively, and the complementarity determining region sequences (CDR-L1, L2, and L3) of the light chain variable region that are shown in SEQ ID NO: 59, SEQ ID NO: 60, and SEQ ID NO: 61 respectively, and which also comprises framework region sequences that are derived from a human germline and are selected under optimal alignment.

The present invention further provides an anti-CDH3 humanized antibody, which shows a sequence homology of at least 90% with the aforementioned anti-CDH3 humanized antibody, and which is capable of recognizing CDH3.

The present invention further provides an anti-CDH3 humanized antibody, wherein one to several amino acids in the framework region portions of the aforementioned antibody are substituted with other amino acids, and the anti-CDH3 humanized antibody is capable of recognizing CDH3.

The present invention further provides an anti-CDH3 humanized antibody, wherein one to several amino acids in the complementarity determining region sequences of the aforementioned antibody, which are at the boundary with the framework regions, are substituted with other amino acids, and the anti-CDH3 humanized antibody is capable of recognizing CDH3.

Preferably, the amino acid to be substituted is the amino acid at position 55 (Kabat's numbering) in the light chain variable region.

Preferably, the amino acids to be substituted are one or more selected from the amino acids at positions 49, 71 and 78 (Kabat's numbering) in the heavy chain variable region.

Preferably, the amino acid at position 55 (Kabat's numbering) in the light chain variable region is substituted with alanine.

Preferably, the amino acid at position 71 (Kabat's numbering) in the heavy chain variable region is substituted with lysine.

Preferably, the amino acid at position 78 (Kabat's numbering) in the heavy chain variable region is substituted with valine.

Preferably, the amino acid at position 49 (Kabat's numbering) in the heavy chain variable region is substituted with alanine.

Preferably, the aforementioned antibody has one or more substitutions selected from the substitution of the amino acid residue at position 49 (Kabat's numbering) in the heavy chain variable region with alanine, the substitution of the amino acid residue at position 71 (Kabat's numbering) in the heavy chain variable region with lysine, the substitution of the amino acid residue at position 78 (Kabat's numbering) in the heavy chain variable region with valine, and the substitution of the amino acid residue at position 55 (Kabat's numbering) in the light chain variable region with alanine.

The present invention provides an antibody set forth in any one of the followings:
(1) an anti-CDH3 humanized antibody having the amino acid sequence shown in SEQ ID NO: 48 in the heavy chain variable region and the amino acid sequence shown in SEQ ID NO: 49 in the light chain variable region; (Antibody number: PPAT-076-44Ha)
(2) an anti-CDH3 humanized antibody having the amino acid sequence shown in SEQ ID NO: 50 in the heavy chain variable region and the amino acid sequence shown in SEQ ID NO: 51 in the light chain variable region; (Antibody number: PPAT-076-44Hb)
(3) an anti-CDH3 humanized antibody having the amino acid sequence shown in SEQ ID NO: 52 in the heavy chain variable region and the amino acid sequence shown in SEQ ID NO: 53 in the light chain variable region; (Antibody number: PPAT-076-44Hc) and
(4) an anti-CDH3 humanized antibody having the amino acid sequence shown in SEQ ID NO: 54 in the heavy chain variable region and the amino acid sequence shown in SEQ ID NO: 55 in the light chain variable region: (Antibody number: PPAT-076-44Hd).

Preferably, the antibody of the present invention has an ability to bind to CDH3.

Preferably, the antibody of the present invention is Fab, $F(ab')^2$, or scFv.

The present invention further provides a partial sequence of the aforementioned antibody, wherein the partial sequence has an ability to bind to CDH3.

Preferably, the CDH3 is human CDH3.

Preferably, the CDH3 is an extracellular region shown in SEQ ID NO: 2 (corresponding to amino acids 1-654 of SEQ ID NO:2).

The present invention further provides an immune complex, in which the aforementioned anti-CDH3 humanized antibody, the fragment thereof, or the partial sequence thereof is conjugated to a chemotherapeutic agent or a radioactive material.

Preferably, the chemotherapeutic agent is a cytotoxic substance.

Preferably, the cytotoxic substance is a maytansinoid or a derivative thereof, or an auristatin or a derivative thereof.

Preferably, the cytotoxic substance is a maytansinoid selected from DM1, DM3 and DM4, or a derivative thereof, or an auristatin selected from MMAE and MMAF, or a derivative thereof.

Preferably, an average of one to seven DM1 molecules are bound to a single molecule of the anti-CDH3 humanized antibody, the fragment thereof, or the partial sequence thereof.

Preferably, the anti-CDH3 humanized antibody, the fragment thereof, or the partial sequence thereof is conjugated to a chemotherapeutic agent via a linker.

Preferably, the anti-CDH3 humanized antibody, the fragment thereof, or the partial sequence thereof is conjugated to a chemotherapeutic agent, via an intramolecular disulfide bond in the Fc region of the antibody, or by modifying the Fc region of the antibody through a genetic engineering technique.

Preferably, the linker is a divalent reaction crosslinking reagent.

Preferably, the linker is selected from the group consisting of N-succinimidyl 4-(maleimidomethyl)cyclohexanecarboxylate (SMCC), sulfosuccinimidyl-4-(N-maleimidomethyl)-cyclohexane-1-carboxylate (Sulfo-SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimide butyric acid N-succinimidyl ester (GMBS), ε-maleimidocaproic acid N-hydroxysuccinimide ester (EMCS), m-maleimide benzoyl-N-hydroxysuccinimide ester (MBS), N-(α-maleimidoacetoxy)-succinimide ester (AMAS), succinimidyl-6-(β-maleimidopropionamide)hexanoate (SMPH), N-succinimidyl 4-(p-maleimidophenyl)butyrate (SMPB), N-(p-maleimidophenyl)isocyanate (PMPI), N-succinimidyl 4(2-pyridylthio)pentanoate (SPP), N-succinimidyl(4-iodoacetyl)aminobenzoate (SIAB), 6-maleimidocaproyl (MC), maleimidopropanoyl (MP), p-aminobenzyloxycarbonyl (PAB), and N-succinimidyl (4-(2-pyridylthio)butanoate (SPDB).

Preferably, the linker is cleaved by protease.

Preferably, the linker comprises at least one of valine-citrulline (Val-Cit), alanine-phenylalanine (ala-phe), and para-aminobenzoic acid (PABA).

Preferably, cytotoxic performance is reinforced by humanization of the framework region sequences of antibody variable regions.

The present invention further provides a medicament for treating a disease that is characterized by overexpression of CDH3, wherein the medicament comprises the aforementioned immune complex.

Preferably, the disease characterized by overexpression of CDH3 is cancer.

Preferably, the cancer is selected from among colorectal cancer, non-small-cell lung cancer, breast cancer, cancer of the head and neck, ovarian cancer, lung cancer, invasive bladder cancer, pancreatic cancer, metastatic brain tumor, thyroid cancer, squamous cell carcinoma of the head and neck, squamous cell carcinoma of the esophagus, squamous cell carcinoma of the lung, squamous cell carcinoma of the skin, melanoma, mammary cancer, pulmonary adenocarcinoma, squamous cell carcinoma of the uterine cervix, squamous cell carcinoma of the pancreas, squamous cell carcinoma of the colon, squamous cell carcinoma of the stomach, prostate cancer, osteosarcoma, and soft tissue sarcoma.

Preferably, the medicament of the present invention is used as an antitumor agent.

The present invention further provides a method of treating a disease that is characterized by overexpression of CDH3, which comprises administering the aforementioned immune complex to a patient.

The present invention further provides a use of the aforementioned immune complex for a production of a medicament for treating a disease that is characterized by overexpression of CDH3.

Advantageous Effects of Invention

The anti-CDH3 humanized antibody is anticipated to have lower immunogenicity than that of the original antibody thereof. A humanized antibody is composed of an appropriate combination of the CDR sequences of the original antibody and human-derived FR sequences. If such a humanized antibody does not exhibit affinity for an antigen, an attempt is further made to recover affinity by introduction of amino acid mutations into the variable region of the antibody. As a result of the combination of the CDR sequences and appropriate FR sequences and as necessary, introduction of amino acid mutations, an anti-CDH3 humanized antibody specifically binding to CDH3 can be obtained. An immune complex obtained by conjugating the thus obtained anti-CDH3 humanized antibody of the present invention with a chemotherapeutic agent exhibits a stronger cytotoxicity to cancer cells expressing CDH3, when compared with an antibody that does not bind to a chemotherapeutic agent. Moreover, the immune complex obtained by conjugating the anti-CDH3 humanized antibody of the present invention with a chemotherapeutic agent exhibits improved affinity in comparison to an anti-CDH3 chimeric antibody as described in WO 2013/150623 (Patent Literature 6), and it also exhibits a stronger cytotoxicity in comparison to an immune complex obtained by connecting the anti-CDH3 chimeric antibody with a chemotherapeutic agent. Accordingly, by administration of the immune complex of the present invention to a patient having cancer cells that express CDH3, high anticancer action can be exhibited, and at the same time, a reduction in its own immunogenicity can also be achieved. The immune complex of the present invention is useful as an anticancer agent.

BRIEF DESCRIPTION OF DRAWINGS

The patent or application file contains at least one color drawing. Copies of this patent or patent application publication with color drawing will be provided by the USPTO upon request and payment of the necessary fee.

FIG. 1 shows the results of flow cytometry, in which a cell line with forcible expression of human CDH3 was reacted with a commercially available anti-human CDH3 antibody. A: CHO cells, B: CHO cells with forcible expression of CDH3, and C: lung cancer-derived cell line NCI-H358. a: 0.01 μg/mL anti-CDH3 antibody, b: 0.1 μg/mL anti-CDH3 antibody, and c: 1 μg/mL anti-CDH3 antibody.

FIG. 2 shows the results of flow cytometry performed on the obtained antibodies. Three cases of typical flow cytometry results obtained from the obtained antibody group are shown in FIGS. 2A to 2C. A: CHO cells with forcible expression of CDH3, B: CHO cells, and C: lung cancer-derived cell line NCI-H358. a: 0.01 μg/mL anti-CDH3 antibody, b: 0.1 μg/mL anti-CDH3 antibody, and c: 1 μg/mL anti-CDH3 antibody. FIG. 2D shows the results of flow cytometry performed on a mouse antibody (PPAT-076-44M) purified from the hybridoma derived from Accession No. NITE BP-1536. The right peak in each view of FIG. 2D indicates a negative control in which an antibody with identical isotype was used, and the left peak in each view indicates the results obtained by measuring PPAT-076-44M at 10 μg/mL.

FIG. 5 shows the results of flow cytometry in which individual CDH3 antibodies were each reacted with the cells mentioned below. The used cell lines were A: lung cancer-derived cell line NCI-H358, B: CHO cells, and C: CHO cells with forcible expression of CDH3. The peak on the left side in each view indicates a negative control.

FIG. 7 shows the results of a cytotoxicity test performed on CDH3 antibody drug conjugates. A: NCI-H358 cell line, antibody drug conjugates (PPAT-076-44Hb and PPAT-076-44Hd, to which a drug is bound), B: HCC1954 cell line, antibody drug conjugate (PPAT-076-44Hd, to which a drug is bound), C: HCC70 cell line, antibody drug conjugate (PPAT-076-44Hd, to which a drug is bound), and D: the cell lines shown in Table 1, antibody conjugate (PPAT-076-44Hd, to which a drug is bound).

FIG. 15 shows the relative affinity of CDH3 antibody drug conjugates having different average drug-to-antibody ratios (DAR), with respect to an antibody to which a drug is not bound. A: PPAT-076-44Hb, and B: PPAT-076-44Hd.

FIG. 16 shows the expression of CDH3 in the cancer-bearing tumor tissue portions of cancer-bearing mouse models used in animal tests. A: HCC1954, B: HCC70, and C: Oka-C-1.

EMBODIMENTS OF CARRYING OUT THE INVENTION

Figure 3:
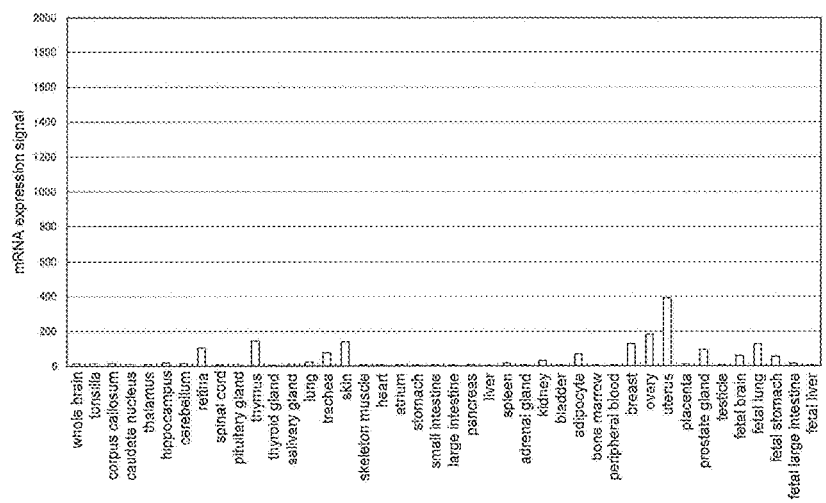
FIG. 3 shows the results regarding the expression of CDH3 mRNA in various types of tumor tissues. A: normal tissues, B: various types of cancer tissues, and C: the degree of differentiation of pancreatic cancer.
Figure 3:
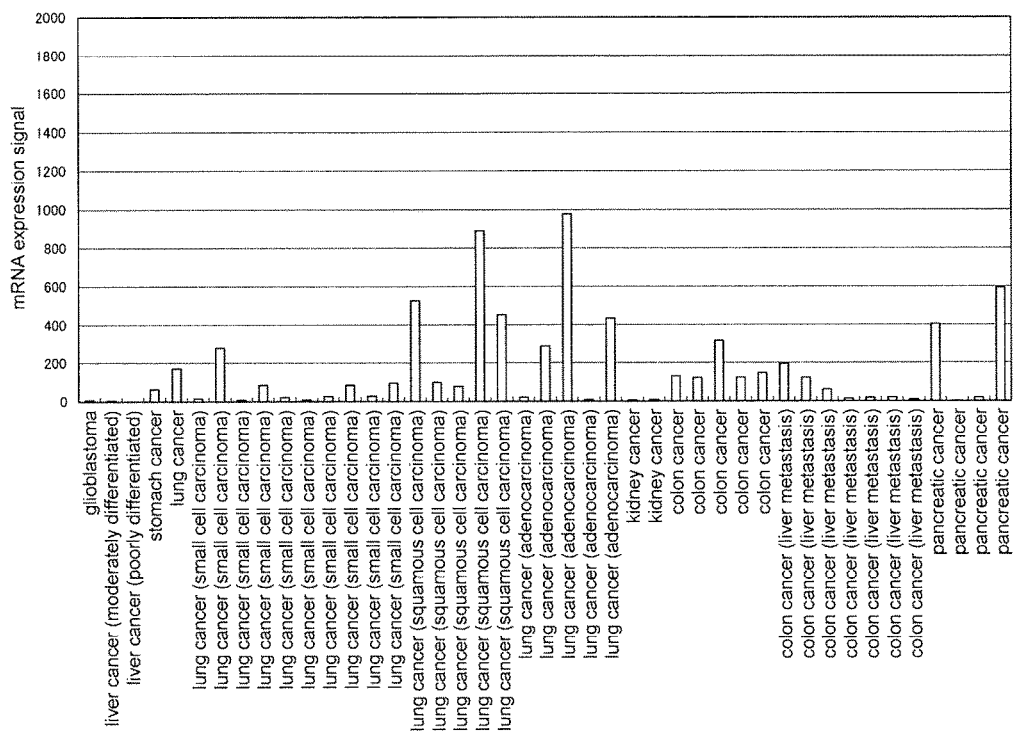
Figure 3:
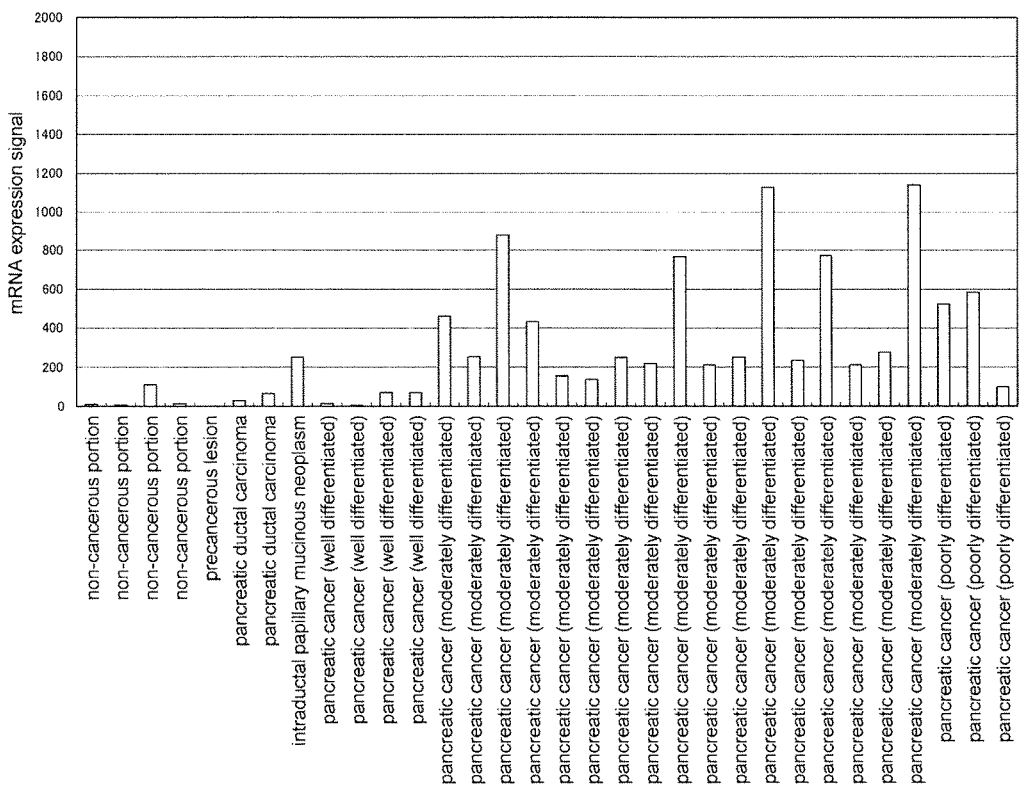

Hereinafter, the present invention will be described more in detail.

The present invention relates to an anti-CDH3 humanized antibody and a method of using the same. The anti-CDH3 humanized antibody of the present invention is provided by combining the CDR sequences of an antibody specifically recognizing CDH3 with various suitable human-derived FR sequences. Moreover, the present anti-CDH3 humanized antibody is provided by introducing a suitable amino acid mutation therein in order to improve its affinity. In one aspect, the antibody of the present invention binds to CDH3 expressed on the surface of a cell. In one aspect, the antibody of the present invention binds to an epitope in the CDH3 region. The antibody of the present invention binds preferably to CDH3 expressed on the surface of a human cell, and particularly preferably to CDH3 expressed on the surface of a cancer cell. In one aspect, the antibody of the present invention may be a humanized antibody fragment selected from Fab, Fab'-SH, Fv, scFv, and (Fab')$_2$ fragments. Such an antibody is efficiently bound to a chemotherapeutic agent via, for example, various types of linkers, so that it can be used as an antibody drug conjugate. Furthermore, the antibody of the present invention can also be bound to toxin via any given spacer. That is to say, according to the present invention, an anti-CDH3 humanized antibody drug conjugate that efficiently kills cancer cells is provided.

As an antigen used to generate the antibody of the present invention, CDH3 or a partial peptide thereof can be used. As an example, a soluble CDH3 protein that corresponds to a CDH3 extracellular region (corresponding to amino acids at positions 1 to 654 of SEQ ID NO: 2) can be used, but the examples of the antigen are not limited thereto.

The antibody of the present invention is a humanized monoclonal antibody. In the present invention, a hybridoma is obtained by immunization of a mouse, and is used as a raw material for obtaining such a humanized monoclonal antibody. Such a raw material can be obtained by various methods that are well known in the present field. The raw material can be obtained, for example, by the below-mentioned method, but the method is not limited thereto.

In order to establish a hybridoma that generate an antibody specifically binding to CDH3, first, CDH3 or a partial peptide thereof is administered as an antigen to a mouse. The dosage amount of such an antigen per mouse is 0.1 to 100 mg if an adjuvant is not used, and is 1 to 100 μg when an adjuvant is used. Examples of such an adjuvant used herein include a Freund's complete adjuvant (FCA), a Freund's incomplete adjuvant (FIA), and an aluminum hydroxide adjuvant. Immunization is mainly carried out by injecting the antigen into the vein, subcutis, or abdominal cavity. In addition, immunization intervals are not particularly limited, and the immunization is carried out 1 to 10 times, and more preferably 2 to 5 times, at intervals of several days to several weeks, and preferably at intervals of 2 to 5 weeks. Thereafter, one to sixty days, and preferably one to fourteen days after the final immunization, antibody-producing cells are collected. Examples of the antibody-producing cells include splenic cells, lymph node cells, and peripheral blood cells. Among these cells, splenic cells or local lymph node cells are preferable.

To obtain hybridomas, cell fusion of antibody-producing cells with myeloma cells is carried out. As myeloma cells, commercially available, established cells, which have drug selectivity to a HAT medium and the like and are derived from mice, can be used. Examples of the myeloma cells include P3X63-Ag.8.U1 (P3U1) and NS-1.

For cell fusion, antibody-producing cells ($1 \times 10^6$ to $1 \times 10^7$ cells/mL) are mixed with myeloma cells ($2 \times 10^5$ to $2 \times 10^6$ cells/mL) in an animal cell culture medium containing no serum, such as DMEM or a RPMI-1640 medium, so that a fusion reaction can be carried out in the presence of a cell fusion promoter. As a cell fusion promoter, polyethylene glycol with a mean molecular weight of 1000 to 6000 Daltons or the like can be used. In addition, antibody-producing cells may also be fused with myeloma cells using a commercially available cell fusion apparatus that utilizes electrical stimulation.

Hybridomas can be obtained by an operation to culture a selection medium. A cell suspension is appropriately diluted, for example, with a fetal bovine serum-containing RPMI-1640 medium, and the resulting cell suspension is seeded at a cell density of approximately $3 \times 10^5$ cells/well on a microtiter plate. Thereafter, a selection medium is added to each well, and a culture is then carried out, while exchanging the selection medium with a fresh one, as appropriate. As a result, cells growing approximately 14 days after initiation of the culture in the selection medium can be obtained as hybridomas.

Thereafter, the presence or absence of an antibody of interest in a culture supernatant of the growing hybridomas is screened. The screening of hybridomas may be carried out according to an ordinary method, and the type of the screening method is not particularly limited. For instance, an aliquot of the culture supernatant of the growing hybridomas contained in the well is collected, and it is then subjected to enzyme immunoassay, radioimmunoassay or the like, so that hybridomas that produce an antibody binding to CDH3 can be screened. The fused cells are cloned according to limiting dilution or the like, and thus, hybridomas can be finally established as cells that produce a monoclonal antibody.

Using the established hybridomas as raw materials, humanization of an antibody derived therefrom can be achieved by a known method. Specifically, a DNA sequence designed to ligate the CDR of a mouse antibody to the framework region (FR) of a human antibody is synthesized from several oligonucleotides produced to have some overlapped portions at the termini thereof according to a PCR method. The obtained DNA is ligated to DNA encoding the constant region of a human antibody, and the thus ligated DNA portion is then incorporated into an expression vector, and this expression vector is then introduced into a host, so that a humanized antibody can be generated (EP239400 (Patent Literature 7), International Publication WO 96/02576 (Patent Literature 8), etc.).

The complementarity determining region (CDR) sequence is particularly different in the variable regions among antibodies, and this sequence indicates a sequence region that plays an extremely important role for determination of the specificity of the antibody. Amino acid residues in this region are considered to comprise many residues that are directly associated with the binding ability and specificity of the antibody to an antigen, and three regions are present in each of the light chain and heavy chain variable regions.

CDR is determined by sequence comparison according to Kabat et al. (Sequences of proteins of immunological interest, 5th Ed., Public Health Service, National Institutes of Health, Bethesda, Md. (1991) (Non Patent Literature 15)), and it is also determined based on its three-dimensional structure according to Chothia et al. (J. Mol. Biol.; 196, p. 901 (1987) (Non Patent Literature 16)).

The CDR determined by Kabat is generally located around residues 24-34, 50-56, and 89-97 in the light chain variable region, and also around residues 31-35, 50-65, and 95-102 in the heavy chain variable region. However, it is not always necessary that all of the residues in this region are directly associated with the binding of the antibody to an antigen. It is not the case that the residues are completely identical to the CDR region determined based on the three-dimensional structure. It is to be noted that the number assignment system used to describe an amino acid residue number in the present description is based on a Kabat's numbering system.

The human FR sequence is appropriately selected on a timely basis. In the present description, the selected human FR sequence comprises a light chain variable region or a heavy chain variable region obtained from a human consensus framework sequence.

The human consensus framework sequence is an FR sequence that indicates amino acid residues most commonly appearing in the human immunoglobulin light chains or heavy chain variable region. In general, the human immunoglobulin light chain or heavy chain variable region is selected from subgroups of variable region sequences. According to Kabat et al., the light chain variable region is a light chain human κ subgroup I, and the heavy chain variable region is a heavy chain human subgroup III.

In one embodiment, the light chain human κ subgroup I consensus sequence comprises at least a part of or all of the following sequences, and it is configured such that CDR sequences are sandwiched by a part of or all of the sequences of FR-L1, FR-L2, FR-L3 and FR-L4.

(FR-L1)
SEQ ID NO: 62
DIQMTQSPSSLSASVGDRVTITCRASQ:

(FR-L2)
SEQ ID NO: 63
WYQQKPGKAPK:

(FR-L3)
SEQ ID NO: 64
LQSGVPSRFSGSGSGTDFTLTISSLQPEDFATYYC:

(FR-L4)
SEQ ID NO: 65
FGQGTKVEIK:

In one embodiment, the heavy chain human subgroup III consensus sequence comprises at least a part of or all of the following sequences, and it is configured such that CDR sequences are sandwiched by a part of or all of the sequences of FR-H1, FR-H2, FR-H3 and FR-H4.

(FR-H1)
SEQ ID NO: 66
EVQLVESGGGLVQPGGSLRLSCAASGF:

(FR-H2)
SEQ ID NO: 67
WVRQAPGKGLEWV:

(FR-H3)
SEQ ID NO: 68
YADSVKGRFTISRDNSKNTLYLQMNSLRAEDTAVYYC:

(FR-H4)
SEQ ID NO: 69
WGQGTLVTVSS:

The above-mentioned human consensus framework sequence is composed of amino acid residues that appear at the highest frequency in each subgroup.

In addition, in the present invention, a framework sequence derived from a human germline selected under optimal alignment can also be used. This framework sequence complies with a case in which a human consensus framework sequence is not necessarily suitable for antibody humanization, and it is known as a best-fit method.

Specifically, the variable region sequence of a mouse antibody is screened against a known library of human variable region sequences. As a result, a human variable region sequence that is most similar to the mouse antibody variable region sequence can be used as a human framework sequence derived from the germline of a humanized antibody (Sims et al., J. Immunol.; 151, p. 2296 (1993) (Non Patent Literature 17), Chothia et al., J. Mol. Biol.; 196, p. 901 (1987) (Non Patent Literature 18), and Tempest et al., Biotechnology; 9, p. 266 (1991) (Non Patent Literature 19)).

The most sequence-similar germline sequence can be confirmed by carrying out an alignment against the sequence of the original antibody, using database in which a large number of such libraries have been registered (e.g., IMGT/V-QUEST).

In one embodiment, the light chain germline sequence comprises at least a part of or all of the following sequences, and it is configured such that CDR sequences are sandwiched by a part of or all of the sequences of FR-L1, FR-L2, FR-L3 and FR-L4.

```
(FR-L1)
                                              SEQ ID NO: 72
DIQLTQSPSSLSASVGDRVTITCRASQ:

(FR-L2)
                                              SEQ ID NO: 73
WYQQKPGKAPK:

(FR-L3)
                                              SEQ ID NO: 74
LESGVPSRFSGSGSGTDFTLTISSLQPEDFATYYC:

(FR-L4)
                                              SEQ ID NO: 75
FGQGTKVEIK:
```

In one embodiment, the heavy chain germline sequence comprises at least a part of or all of the following sequences, and it is configured such that CDR sequences are sandwiched by a part of or all of the sequences of FR-H1, FR-H2, FR-H3 and FR-H4.

```
(FR-H1)
                                              SEQ ID NO: 76
QVQLVESGGGVVQPGRSLRLSCAASGF:

(FR-H2)
                                              SEQ ID NO: 77
WVRQAPGKGLEWV:

(FR-H3)
                                              SEQ ID NO: 78
YADSVKGRFTISRDNSKNTLYLQMNSLRAEDTAVYYC:

(FR-H4)
                                              SEQ ID NO: 79
WGQGTLVTVSS:
```

Whether or not a framework (FR) sequence selected by a certain method is suitable for humanization can be determined based on whether or not the combination of the CDR sequences of each antibody clone and the FR sequence is appropriate and whether or not an appropriate conformation can be maintained with respect to an antigen to which the antibody is to be bound.

With regard to a humanized antibody expressed by transplantation of the alternate combination of CDR sequences and human-derived FR sequences, if the selected sequences were not suitable, a reduction in affinity would often occur. This means that several residues present in the FR region also play an important role for the maintenance of the structure. In order to cope with this phenomenon, an amino acid residue substitution can be carried out. For example, as a result of the alignment, several amino acid residues can be substituted with the amino acid residues derived from a mouse antibody, which are present in locations homologous to a human-derived sequence (reshape). Thereby, there is a case in which a reduction in affinity caused by humanization can be improved.

The positions of amino acid residues to be substituted are different depending on a target antibody. In many cases, such positions cannot be specified until the antibody is actually expressed. In the after-mentioned Examples, one or more amino acid residues at positions selected from position 55 in the light chain variable region and positions 49, 71 and 78 in the heavy chain variable region, which have been substituted in relatively many publications (e.g., Proc. Natl. Acad. Sci. U.S.A.; 89, p. 4285 (1992) (Non Patent Literature 20)), were substituted, so that a reduction in affinity could be improved. However, positions to be substituted, combinations, and the types of amino acid residues after completion of the substitution are not limited thereto, and are, determined, as appropriate.

Many hosts used to produce antibodies are derived from mammals. A person skilled in the art could appropriately select a specific host cell system that is most suitable for a gene product to be expressed. Examples of a common host cell system include, but are not limited to, a CHO-derived cell line (a Chinese hamster ovary cell line), CV1 (a monkey kidney system), COS (a derivative of CV1 to an SV40T antigen), SP2/0 (mouse myelomas), P3x63-Ag3.653 (mouse myelomas), 293 (human kidney), and 293T (a derivative of 293 to an SV40T antigen). Such a host cell system is available from various types of manufacturers, the American Tissue Culture Collection (ATCC), or study paper-publishing institutions described in some publications.

As a host cell system, either a CHO-derived cell line involving defective expression of a dgfr gene, or SP2/0, can be preferably used (Urland, G. et al., Somat. Cell. Mol. Genet.; 12, p. 5555 (1986) (Non Patent Literature 4), and Schulman, M. et al., Nature; 276, p, 269 (1978) (Non Patent Literature 5)). Most preferably, the host cell system is DHFR-deficient CHO.

Transfection of a plasmid into a host cell can be carried out by any given technique. Specific examples of such a transfection method include, but are not limited to, transfection (including a calcium phosphate method, a DEAE method, lipofection, and electroporation), a method of introducing DNA utilizing an envelope such as Sendai virus, microinjection, and infection using viral vectors such as retrovirus or adenovirus (Current Protocols in Molecular Biology, Chapter 9 Introduction of DNA into Mammalian Cells, John Wiley and Sons, Inc.), Introduction of a plasmid into a host by electroporation is most preferable.

These antibodies may be any one of a monovalent antibody, a divalent antibody and a polyvalent antibody, as long as they are capable of recognizing CDH3. The antibodies may also be low-molecular-weight antibodies such as an antibody fragment, or modifications of antibodies. Moreover, the antibodies may also be antibody fragments or low-molecular-weight antibodies, such as Fab, Fab', F (ab')$_2$, Fv, ScFv (single chain Fv) or Diabody, with which an Fc portion is fused. In order to obtain such antibodies, genes encoding these antibodies may be constructed, and they may be then each introduced into expression vectors, and they may be then allowed to express in suitable host cells.

A preferred use aspect of the antibody of the present invention can be an immune complex in which a chemotherapeutic agent such as a cytotoxic substance is bound to an antibody, namely, an antibody drug conjugate (ADC). The immune complex of the present invention is allowed to come into contact with, for example, cancer cells that express CDH3, so as to damage the cancer cells.

Examples of the chemotherapeutic agent used in the present invention include duocarmycin, analogs and derivatives of duocarmycin, CC-1065, duocarmycin analogs comprising CBI as a main ingredient, duocarmycin analogs comprising MCBI as a main ingredient, duocarmycin analogs comprising CCBI as a main ingredient, doxorubicin, doxorubicin conjugates, morpholino-doxorubicin, cyanomorpholino-doxorubicin, dolastatin, dolastatin-10, combretastatin, calicheamicin, maytansine, maytansine analogs, DM1, DM2, DM3, DM4, DMI, auristatin E, auristatin EB (AEB), auristatin EFP (AEFP), monomethyl auristatin E (MMAE), monomethyl auristatin F (MMAF), 5-benzoyl valeric acid AE ester (AEVB), tubulysin, disorazole, epothilone, paclitaxel, docetaxel, SN-38, topotecan, rhizoxin, echinomycin, colchicine, vinblastine, vindesine, estramustine, cemadotin, eryuterobin, methotrexate, methopterin, dichloromethotrexate, 5-fluorouracil, 6-mercaptopurine, cytosine arabinoside, melphalan, leurosine, leurosideine, actinomycin, daunorubicin, daunorubicin conjugates, mitomycin C, mitomycin A, carminomycin, aminopterin, tallysomycin, podophyllotoxin, podophyllotoxin derivatives, etoposide, etoposide phosphate, vincristine, taxol, taxol taxotere retinoic acid, butyric acid, $N^8$-acetyl spermidine and camptothecin. However, the examples of the present chemotherapeutic agent are not limited thereto.

The immune complex of the present invention can be produced by binding the above-described chemotherapeutic agent to an antibody according to a known method. The antibody may be directly bound to the chemotherapeutic agent via their linking group or the like, or they may be indirectly bound to each other via a linker or another substance.

Examples of the linking group used when a drug is directly bound to the antibody include a disulfide bond using an SH group and a bond mediated by maleimide. For instance, an intramolecular disulfide bond in the Fc region of the antibody and the disulfide bond of a drug are reduced, and they are then bound to each other via a disulfide bond. Moreover, there is also a method involving mediation of maleimide. Furthermore, as an alternative method, there is also a method of introducing cysteine into an antibody in a genetically engineering manner It is also possible to indirectly bind the antibody to the chemotherapeutic agent via another substance (linker). The linker desirably has one or two or more types of functional groups that react with the antibody, or with the drug, or with both of them. Examples of such a functional group include an amino group, a carboxyl group, a mercapto group, a maleimide group, and a pyridinyl group.

Examples of the linker include N-succinimidyl 4-(maleimidomethyl)cyclohexanecarboxylate (SMCC), sulfosuccinimidyl-4-(N-maleimidomethyl)-cyclohexane-1-carboxylate (Sulfo-SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimide butyric acid N-succinimidyl ester (GMBS), ε-maleimidocaproic acid N-hydroxysuccinimide ester (EMCS), m-maleimide benzoyl-N-hydroxysuccinimide ester (MB S), N-(α-maleimidoacetoxy)-succinimide ester (AMAS), succinimidyl-6-(β-maleimidopropionamide) hexanoate (SMPH), N-succinimidyl 4-(p-maleimidophenyl) butyrate (SMPB), N-(p-maleimidophenyl)isocyanate (PMPI), N-succinimidyl 4(2-pyridylthio)pentanoate (SPP), N-succinimidyl(4-iodo-acetyl)aminobenzoate (SIAB), 6-maleimidocaproyl (MC), maleimidopropanoyl (MP), p-aminobenzyloxycarbonyl (PAB), and N-succinimidyl (4-(2-pyridylthio)butanoate (SPDB), but the examples are not limited thereto. As such a linker, a peptide linker such as valine-citrulline (Val-Cit) or alanine-phenylalanine (ala-phe) may be combined with para-aminobenzoic acid (PABA), or alternatively, the aforementioned linkers may be combined with one another, as appropriate and may be then used.

With regard to the method of binding a drug to an antibody, such binding can be carried out according to the methods described, for example, in Cancer Res.; 52, p. 127 (1992) (Non Patent Literature 13), Cancer Res.; 68 (22), p. 9280 (2008) (Non Patent Literature 6), Nature Biotechnology; 26 (8), p. 925 (2008) (Non Patent Literature 7), Bio Conjugate Chemistry; 19, p. 1673 (2008) (Non Patent Literature 8), Cancer Res.; 68 (15), p. 6300 (2008) (Non Patent Literature 9), or JP Patent Publication (Kohyo) No. 2008-516896 A (Patent Literature 9).

Another embodiment of the present invention includes what is called immunotoxin, in which a toxin is bound to an antibody in a chemical or genetically engineering manner. Examples of the toxin used in the present invention include, but are not limited to, diphtheria toxin A chain, Pseudomonas endotoxin, ricin A chain, abrin A chain, modeccin A chain, gelonin, and saporin.

In a further embodiment of the present invention, a radioactive material can be bound to the antibody. When the antibody is used as a therapeutic agent for cancer, the radioactive material is preferably a cytotoxic radioactive metal. On the other hand, when the antibody is used as a diagnostic agent for cancer, it is preferably a non-cytotoxic radioactive metal.

Examples of the cytotoxic radioactive metal include yttrium 90 (90Y), rhenium 186 (186Re), rhenium 188 (188Re), copper 67 (67Cu), iron 59 (59Fe), strontium 89 (89Sr), gold 198 (198Au), mercury 203 (203Hg), lead 212 (212Pb), dysprosium 165 (165Dy), ruthenium 103 (103Ru), bismuth 212 (212Bi), bismuth 213 (213Bi), holmium 166 (166Ho), samarium 153 (153Sm), and lutetium 177 (177Lu). Among these radioactive metals, 90Y, 153Sm, and 177Lu are preferable in terms of half-life, radiation energy, an ease labeling reaction, a labeling rate, the stability of a complex, etc. However, examples of the cytotoxic radioactive metal are not limited thereto.

On the other hand, examples of the non-cytotoxic radioactive metal that is preferably used in diagnostic agents include, but are not limited to, technetium 99m (99mTc), indium 111 (111In), indium 113m (113mIn), gallium 67 (67Ga), gallium 68 (68Ga), thallium 201 (201T1), chromium 51 (51Cr), cobalt 57 (57Co), cobalt 58 (58Co), cobalt 60 (60Co), strontium 85 (85Sr), mercury 197 (197Hg), and copper 64 (64Cu).

In order to bind such a radioactive metallic element to the anti-cadherin antibody, it is preferable that a metal-chelating reagent is reacted with the antibody, and that the reaction product is further reacted with a radioactive metallic element, so as to form a complex. To the thus obtained modified antibody, the radioactive metallic element is bound via the metal-chelating reagent.

Examples of the metal-chelating reagent used in the formation of such a complex include: (1) quinoline derivatives such as 8-hydroxyquinoline, 8-acetoxyquinoline, 8-hydroxyquinaldine, oxyquinoline sulfate, O-acetyloxine, O-benzoyloxine, O-p-nitrobenzoyloxine, and quinolone compounds having a quinoline skeleton (e.g., norfloxacin, ofloxacin, enoxacin, ciprofloxacin, lomefloxacin, tosfloxacin, fleroxacin, and sparfloxacin); (2) compounds such as chloranilic acid, aluminon, thiourea, pyrogallol, cupferron, Bismuthiol (II), galloyl gallic acid, thiolide, 2-mercaptobenzothiazole, and tetraphenylarsonium chloride; (3) ethylenediaminetetraacetic acid (EDTA), diethylenetriaminepentaacetic acid (DTPA), and compounds having a skeleton similar thereto (dihydroxyethylglycine, diaminopropanoltetraacetic acid, ethylenediamine diacetic acid, ethylenediaminedipropionic acid hydrochloride, hydroxyethylethylenediaminetriacetic acid, ethylenediaminetetrakis (methylenesulfonic acid), glycol ether diaminetetraacetic acid, hexamethylenediaminetetraacetic acid, hydroxyethyliminodiacetic acid, iminodiacetic acid, diaminopropanetetraacetic acid, nitrilotriacetic acid, nitrilotripropionic acid, nitrilotris(methylenesulfonic acid) trisodium salt, triethylenetetraminehexaacetic acid, methyl DTPA, cyclohexyl DTPA, aminobenzyl EDTA, isothiocyanobenzyl EDTA, isothiocyanobenzyl DTPA, methylisothiocyanobenzyl DTPA, cyclohexylisothiocyanobenzyl DTPA, maleimidopropylamidobenzyl EDTA, maleimidopentylamidobenzyl EDTA, maleimidodecylamidobenzyl EDTA, maleimidopentylamidobenzyl DTPA, maleimidodecylamidobenzyl EDTA, and maleimidodecylamidobenzyl DTPA); and (4) 1,4,7,10-tetraazacyclododecane-1,4,7,10-tetraacetic acid (DOTA), 1,4,7-triazacyclononane-1,4,7-triacetic acid (NOTA), 1,4,8,11-tetraazacyclotetradecane-1,4,8,11-tetraacetic acid (TETA), 1,4,7,10-tetraazacyclododecane (Cyclen), 1,4,8,11-tetraazacyclotetradecan (Cyclam), isothiocyanobenzyl DOTA, and isothiocyanobenzyl NOTA.

Among these metal-chelating reagents, isothiocyanobenzyl DOTA, methylisothiocyanobenzyl DTPA, and cyclohexylisothiocyanobenzyl DTPA are preferable in terms of the ease of a reaction of introducing a metal chelate into the antibody, a labeling rate, the stability of a complex, etc.

Such a radioactive metallic element can be bound to the antibody according to an ordinary method. For example, the antibody is reacted with a metal-chelating reagent to prepare a label precursor, and the precursor is then reacted with a radioactive metallic element.

The immune complex provided by the present invention can appropriately comprise a pharmaceutically acceptable carrier, excipient, diluent and the like, so that the drug can be retained in a stable state. The immune complex of the present invention can be formulated in the form of an injection, for example. The applied dose of the immune complex of the present invention depends on the degree of symptoms, age and body weight of a patient, an administration method, and the like. The weight of the antibody serving as an active ingredient is generally in the range of approximately 10 ng to approximately 100 mg/kg body weight.

The disease that can be treated by the immune complex of the present invention is not particularly limited, as long as CDH3 is expressed in the cells of a patient suffering from the disease. Examples of the disease include, but are not limited to, colorectal cancer, non-small-cell lung cancer, breast cancer, cancer of the head and neck, ovarian cancer, lung cancer, invasive bladder cancer, pancreatic cancer, metastatic brain tumor, thyroid cancer, squamous cell carcinoma of the head and neck, squamous cell carcinoma of the esophagus, squamous cell carcinoma of the lung, squamous cell carcinoma of the skin, melanoma, mammary cancer, pulmonary adenocarcinoma, squamous cell carcinoma of the uterine cervix, squamous cell carcinoma of the pancreas, squamous cell carcinoma of the colon, squamous cell carcinoma of the stomach, prostate cancer, osteosarcoma, and soft tissue sarcoma.

The present invention will be more specifically described in the following examples. However, these examples are provided for illustrative purpose only, and thus, the examples are not intended to limit the content of the present invention. It is to be noted that all of the prior art publications cited in the present description are incorporated herein by reference in their entirety.

EXAMPLES

Example 1

Establishment of CDH3-Expressing CHO Cell Line

In order to obtain a cell line used in screening for an anti-CDH3 antibody, CHO cells expressing the full-length CDH3 were established.

(1) Construction of CDH3 Gene Expression Vector

In order to insert the full-length human CDH3 DNA shown in SEQ ID NO: 1 into a mammalian expression vector pEF4/myc-HisB (Invitrogen), the DNA was digested with two types of restriction enzymes, KpnI (TAKARA BIO INC.) and XbaI (TAKARA BIO INC.), at 37° C. for 1 hour. Thereafter, the resulting DNA was inserted into the pEF4/myc-HisB that had also been digested with KpnI and XbaI according to an ordinary method using T4 DNA ligase (Promega), thereby obtaining an expression vector, pEF4-CDH3-myc-His.

(2) Obtainment of CDH3 Stable Expression Cell Line

On the day before transfection, CHO cells ($8 \times 10^5$) were seeded on a dish with a diameter of 10 cm in accordance with the protocols included with FuGENE (registered trademark) 6 Transfection Reagent (Roche Diagnostics), and they were then cultured overnight. Thereafter, 8 µg of the expression vector pEF4-CDH3-myc-His and 16 µL of the FuGENE 6 reagent were mixed into 400 µL of a serum-free RPMI1640 medium (SIGMA-ALDRICH), and the obtained mixture was then left at room temperature for 15 minutes. Thereafter, the reaction mixture was added to the cell culture, so as to perform transfection. Two days after the transfection, cloning was carried out by limiting dilution using a selective reagent (Zeocin (registered trademark)).

The cloning and selection of CDH3 full-length expression CHO were carried out by a Western blotting method using Anti-c-Myc Monoclonal Antibody (SANTA CRUZ BIOTECHNOLOGY). As a result, a CDH3 full-length expression CHO cell line (EXZ1501) having a high expression level and a high growth rate was obtained. The measurement results obtained by examining the reactivity of this cell line, CHO cells as a parent cell line, and an NCI-H358 lung cancer cell line that had been confirmed to express CDH3, with a commercially available anti-CDH3 antibody (R & D SYSTEMS) by flow cytometry are shown in FIG. 1.

Example 2

Production of Soluble CDH3 Antigen

In order to be used as an immunogen in the production of an anti-CDH3 antibody, a soluble CDH3 (sCDH3) protein, in which its C-terminal transmembrane region and the subsequent regions were deleted, was produced.

(1) Construction of Soluble CDH3 Antigen Expression Vector

Using full-length CDH3 cDNA as a template, a PCR reaction was carried out using a forward primer (CGCGG-TACCATGGGGCTCCCTCGT; SEQ ID NO: 3) and a reverse primer (CCGTCTAGATAACCTCCCTTCCA-GGGTCC; SEQ ID NO: 4) that had been designed to amplify a region corresponding to the CDH3 extracellular region (which corresponded to positions 1-2010 of SEQ ID NO: 1; hereinafter referred to as "sCDH3 cDNA"). KOD-Plus (Toyobo Co., Ltd.) was used in the reaction, and the reaction was carried out under reaction conditions of 30 cycles consisting of 15 seconds at 94° C., 30 seconds at 55° C., and 90 seconds at 68° C.

Thereafter, a gel fragment containing an approximately 2.0-kbp band that was a size of interest was cut out in agarose gel electrophoresis, and using QIA (registered trademark) Quick Gel Extraction Kit (QIAGEN), sCDH3 cDNA of interest was obtained.

In order to insert this sCDH3 cDNA into an expression vector pEF4/myc-HisB, the DNA was digested with two types of restriction enzymes KpnI and XbaI, and it was then inserted into pEF4/myc-HisB that had also been digested with KpnI and XbaI according to an ordinary method using T4 DNA ligase, so as to obtain an expression vector pEF4-sCDH3-myc-His.

(2) Expression of Soluble CDH3 Protein

On the day before transfection, CHO cells ($8 \times 10^5$) were seeded on a dish with a diameter of 10 cm in accordance with the protocols included with the FuGENE 6 Transfection Reagent, and they were then cultured overnight. Thereafter, 8 µg of the expression vector pEF4-CDH3-myc-His and 16 µL of the FuGENE 6 reagent were mixed into 400 µL of a serum-free RPMI1640 medium (SIGMA-ALDRICH), and the obtained mixture was then left at room temperature for 15 minutes. Thereafter, the reaction mixture was added to the cell culture, so as to perform transfection. Two days after the transfection, cloning was carried out by limiting dilution using a selective reagent (Zeocin).

Soluble CDH3-expressing CHO cells were selected according to a Western blot method using an anti-c-Myc monoclonal antibody (SANTA CRUZ BIOTECHNOLOGY). It was attempted to select a cell line, which was able to secrete a large amount of soluble CDH3 into the culture supernatant and which was able to grow favorably. As a result, a soluble CDH3-expressing CHO cell line (EXZ1702) was obtained. Using three roller bottles each having a culture area of 1,500 cm², the selected soluble CDH3-expressing CHO cell line (EXZ1702) was cultured for 72 hours in 333 mL of a serum-free medium CHO-S-SFM-II (Invitrogen) per roller bottle. Thereafter, a culture supernatant was recovered. A soluble CDH3 protein was obtained from the recovered culture supernatant according to affinity chromatography using HisTrap (registered trademark) HP column (GE Healthcare Biosciences) and gel filtration chromatography using Superdex (registered trademark) 200 pg column (GE Healthcare Biosciences).

Example 3

Production of Anti-CDH3 Mouse Antibody (1) Production of Monoclonal Antibody Using Soluble CDH3 Protein as Immunogen 50 µg of a soluble CDH3 protein dissolved in a normal saline and Titer-MAX Gold (registered trademark) (Titer-Max) were mixed in equal volumes. The obtained mixture was injected into the abdominal cavity and subcutis of each MRL/lpr mouse (Japan SLC, Inc.), so as to carry out initial immunization. The second immunization and the subsequent immunizations were carried out by mixing a soluble CDH3 protein (protein amount: 25 µg) that had been prepared in the same manner as described above with Titer-MAX gold and then injecting the obtained mixture into the abdominal cavity and subcutis of the mouse. Three days after the final immunization, splenic cells were aseptically prepared from the mouse, and the splenic cells were then fused with mouse myeloma cells SP2/O-Ag14 or P3-X63-Ag8.653 according to an ordinary method (polyethylene glycol method).

(2) Selection of Anti-CDH3 Mouse Antibody-Producing Hybridomas

An anti-CDH3 mouse antibody was selected by flow cytometry using a CHO cell line (EXZ1501) expressing full-length CDH3. Specifically, the CHO cell line (EXZ1501) that expressed full-length CDH3 was treated with 2 mM EDTA-PBS, so that it was removed from the culture plate. Thereafter, the cells were suspended in a FACS solution (PBS containing 1% BSA, 2mM EDTA, and 0.1% NaN$_3$) to a cell density of $1 \times 10^6$ cells/mL. This cell suspension was seeded on a 96-well plate to an amount of 50 µL/well, and a culture supernatant of hybridomas was then added thereto, so that they were reacted at 4° C. for 60 minutes. Thereafter, the reaction solution was washed with a FACS solution (200 µL/well) two times, and AlexaFluor 488-labeled anti-mouse IgG-goat F(ab')$_2$ (Invitrogen) was then added to the resultant. Then, the mixture was reacted at 4° C. for 30 minutes. Thereafter, the reaction solution was washed with a FACS solution two times, and it was then subjected to flow cytometry, so as to select hybridomas that were reacted with the CDH3-expressing CHO cells.

Typical reaction results obtained from the reactions of an antibody obtained from the aforementioned hybridomas with CDH3-expressing CHO cells (EXZ1501), with CHO cells as a parent cell line, and with a human bronchioalveolar carcinoma cell line NCI-H358 are shown in FIGS. 2A to 2C. It was confirmed that all of the selected hybridomas reacted with CDH3-expressing CHO cells (EXZ1501) and NCI-H358, and did not react with CHO cells. FIG. 2D shows the results of flow cytometry performed on a mouse antibody (antibody No.: PPAT-076-44M) that was purified from hybridomas derived from Accession No. NITE BP-1536.

Example 4

Expression of CDH3 mRNA in Normal Tissues and Cancer Tissues

Samples were recovered from normal human tissues and various types of cancer tissues according to laser capture microdissection, and total RNA was then prepared from each sample according to an ordinary method using ISO-GEN (NIPPON GENE CO., LTD.). 10 ng each of RNA was subjected to gene expression analysis in accordance with Expression Analysis Technical Manual (Affymetrix) using GeneChip U-133B (Affymetrix). The mean value of the expression scores of all genes was set at 100, and genes whose expression had been promoted in cancer cells were then searched. As a result, it was found that the expression of CDH3 had a certain limit in normal human tissues, and that CDH3 was highly expressed in lung cancer, colon cancer, and pancreatic cancer (FIGS. 3A and 3B). Moreover, the expression of CDH3 mRNA was examined in several pancreatic cancer tissues having different degrees of differentiation. As a result, regardless of the degree of differentiation, tissues in which high expression of CDH3 mRNA was observed were found (FIG. 3C).

Example 5

Expression of CDH3 Protein in Cancer Tissues Observed According to Immunohistochemical Staining In order to confirm the expression of the CDH3 protein in clinical cancer specimens, immunostaining was carried out using cancer specimen tissue arrays.

As such cancer specimen tissue arrays, those of pancreatic cancer (adenocarcinoma), lung cancer (adenocarcinoma), lung cancer (squamous cell carcinoma), and colon cancer (adenocarcinoma), manufactured by Shanghai Outdo Biotech Co., Ltd., were used.

A slide of each tissue array was subjected to a deparaffinization treatment, and was then activated in 10mM Tris 1 mM EDTA (pH 9.0) at 95° C. for 40 minutes. Endogenous peroxidase was deactivated using a blocking reagent included with ENVISION+ Kit (Dako), and it was then reacted with an anti-CDH3 antibody 610227 (BD BIOSCIENCE) and with an anti-HBs antibody Hyb-3423 used as a negative control in a concentration of 5 µg/mL at 4° C. overnight. Thereafter, the antibody solution was washed out, and the array was then reacted with a polymer secondary antibody reagent included with ENVISION+Kit at room temperature for 30 minutes. Thereafter, color development was carried out with a coloring reagent included with ENVISION+Kit, and nuclear staining was then performed with a hematoxylin-eosin solution.

Figure 4:
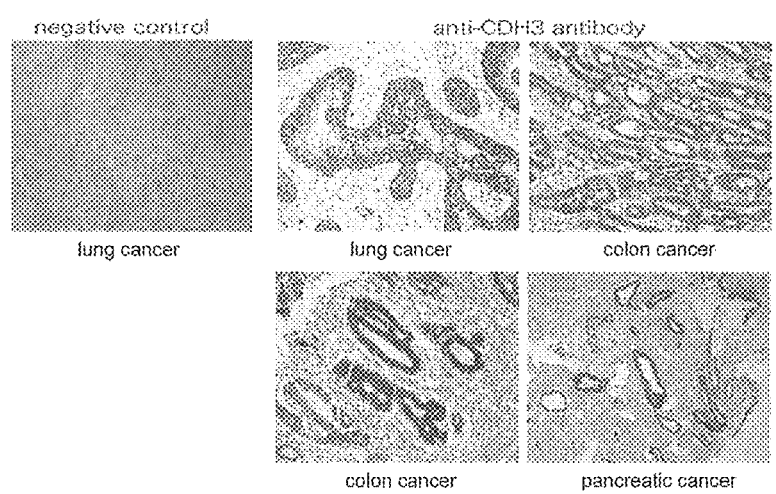
FIG. 4 shows the results regarding the expression of CDH3 in various types of human tumor tissues.

The results are shown in FIG. 4. Cancer cells were stained with the anti-CDH3 antibody, but normal cells were not stained therewith.

Example 6

Purification of RNA from Hybridomas

Cytoplasmic RNA was isolated from mouse hybridoma cells producing the CDH3 antibody according to the method described in Gough, Rapid and quantitative preparation of cytoplasmic RNA from small numbers of cells, Analytical Biochemisty, 173, pp. 93-95 (1988) (Non Patent Literature 10) (wherein another TNE buffer (25 mM Tris-HCl, pH 7.5; 1% NP-40; 150 mM NaCl; 1 mM EDTA, pH 8.0) was used in the present operation, instead of the lysis buffer described in the aforementioned study paper). As a specific operation procedure, hybridoma cells ($5 \times 10^6$) was suspended in 0.2 mL of a TNE buffer to dissolve the cell membrane therein, and the cell nucleus was then removed by centrifugation. To approximately 0.2 mL of the obtained cytoplasm supernatant, 0.2 mL of an extraction buffer (10 mM Tris-HCl, pH 7.5; 0.35 M NaCl; 1% (w/v) SDS; 10 mM EDTA, pH 8.0; 7 M urea) was added. The obtained mixture was extracted with phenol and chloroform, and glycogen (Roche; Cat No. 901393) was then added as a carrier to the obtained RNA solution. The reaction mixture was precipitated with ethanol. Subsequently, 10 to 50 µL of sterile distilled water was added to the RNA precipitate, resulting in a cytoplasmic RNA concentration of 0.5 to 2 µg/µL, so that the precipitate was dissolved therein.

Example 7

Construction of cDNA Library from RNA Prepared from Hybridomas

In order to synthesize single-stranded cDNA, 0.5 to 3 µg of the above-prepared cytoplasmic RNA was added to a reaction solution containing 50 mM Tris-HCl, pH 8.3 (room temperature); 75 mM KCl; 3 mM $MgCl_2$; 10 mM DTT, 100 ng of random primer, 0.5 mM dNTP, and 200 units of Superscript II (reverse transcriptase, Invitrogen) to prepare 20 µL of a reaction mixture, and the reaction mixture was then incubated at 42° C. for 50 minutes. The thus synthesized cDNA library was directly used as a template in a polymerase chain reaction (PCR) method.

Example 8

Amplification of Genes Encoding Anti-CDH3 Mouse Antibody Variable Regions by PCR Method In order to determine the sequences of anti-CDH3 mouse antibody variable regions, using the cDNA library obtained in Example 7 as a template, anti-CDH3 mouse antibody variable region genes were amplified by a PCR method. The primers used herein were all synthesized by Hokkaido System Science Co., Ltd. Gene amplification was carried out using the below-mentioned combinations.

A. PCR Primers for Gene Encoding Mouse Light Chain Variable Region

Using two types of primer sets, namely, (1) a PCR primer having homology with a FR1 portion at the 5'-terminus, and 4 primer sets having homology with a J chain gene in a mouse light chain at the 3'-terminus, and (2) primer sets having homology with an light chain signal portion at the 5'-terminus (7 primer sets), and a primer with a KC portion at the 3'-terminus (KVL antisense primer), mouse immunoglobulin light chain variable region DNA was isolated from the cDNA by a polymerase chain reaction. The primer sequences are as shown below.

It is to be noted that, in the nucleotide sequences, M indicates A or C; R indicates A or G; W indicates A or T; S indicates C or G; Y indicates C or T; K indicates G or T; V indicates A, C or G; H indicates A, C or T; D indicates A, G or T; B indicates C, G or T; and N indicates A, C, G or T.

(1) 4 Sense Primer Sets for Cloning of Mouse Light Chain Variable Region 17 types of sense primers and 3 types of reverse primers were synthesized with reference to "Phage Display—A Laboratory Manual-, Barbas Burton Scott Silverman" PROTOCOL 9.5 (Non Patent Literature 11).

```
VK sense primer (FR1 portion, a mixture of the
following 17 primers)
                                        SEQ ID NO: 5
5'-GAYATCCAGCTGACTCAGCC-3' (Degeneracy 2):

SEQ ID NO: 6
5'-GAYATTGTTCTCWCCCAGTC-3' (Degeneracy 4):

SEQ ID NO: 7
5'-GAYATTGTGMTMACTCAGTC-3' (Degeneracy 8):

SEQ ID NO: 8
5'-GAYATTGTGYTRACACAGTC-3' (Degeneracy 8):

SEQ ID NO: 9
5'-GAYATTGTRATGACMCAGTC-3' (Degeneracy 8):

SEQ ID NO: 10
5'-GAYATTMAGATRAMCCAGTC-3' (Degeneracy 16):

SEQ ID NO: 11
5'-GAYATTCAGATGAYDCAGTC-3' (Degeneracy 12):

SEQ ID NO: 12
5'-GAYATYCAGATGACACAGAC-3' (Degeneracy 4):
```

```
                                                 SEQ ID NO: 13
5'-GAYATTGTTCTCAWCCAGTC-3' (Degeneracy 4):

SEQ ID NO: 14
5'-GAYATTGWGCTSACCCAATC-3' (Degeneracy 8):

SEQ ID NO: 15
5'-GAYATTSTRATGACCCARTC-3' (Degeneracy 16):

SEQ ID NO: 16
5'-GAYRTTKTGATGACCCARAC-3' (Degeneracy 16):

SEQ ID NO: 17
5'-GAYATTGTGATGACBCAGKC-3' (Degeneracy 12):

SEQ ID NO: 18
5'-GAYATTGTGATAACYCAGGA-3' (Degeneracy 4):

SEQ ID NO: 19
5'-GAYATTGTGATGACCCAGWT-3' (Degeneracy 4):

SEQ ID NO: 20
5'-GAYATTGTGATGACACAACC-3' (Degeneracy 2):

SEQ ID NO: 21
5'-GAYATTTTGCTGACTCAGTC-3' (Degeneracy 2):

J antisense (4 primer sets)
J1/J2 antisense primer (1)
                                                 SEQ ID NO: 22
5'-GGSACCAARCTGGAAATMAAA-3' (Degeneracy: 8):

J4 antisense primer (2)
                                                 SEQ ID NO: 23
5'-GGGACAAAGTTGGAAATAAAA-3':

J5 antisense primer (3)
                                                 SEQ ID NO: 24
5'-GGGACCAAGCTGGAGCTGAAA-3':
A mixture of J1/J2, J4, and J5 antisense
primers (4)
```

(2) 7 Primer Sets for Cloning of Mouse Light Chain Variable Region

VK sense primer (signal peptide portion, wherein the nucleotide sequence was modified based on the Mouse Ig-Primer Set of Novagen (Novagen; Merck, Cat. No. 69831-3), such that restriction sites were removed therefrom)

```
Sense primer set A
                                                 SEQ ID NO: 25
5'-ATGRAGWCACAKWCYCAGGTCTTT-3':

Sense primer set B
                                                 SEQ ID NO: 26
5'-ATGGAGACAGACACACTCCTGCTAT-3':

Sense primer set C
                                                 SEQ ID NO: 27
5'-ATGGAGWCAGACACACTSCTGYTATGGGT-3':

Sense primer set D (a mixture of the following two
primers)
                                                 SEQ ID NO: 28
5'-ATGAGGRCCCCTGCTCAGWTTYTTGGIWTCTT-3':

SEQ ID NO: 29
5'-ATGGGCWTCAAGATGRAGTCACAKWYYCWGG-3':

Sense primer set E (a mixture of the following
three primers)
                                                 SEQ ID NO: 30
5'-ATGAGTGTGCYCACTCAGGTCCTGGSGTT-3':

SEQ ID NO: 31
5'-ATGTGGGGAYCGKTTTYAMMCTTTTCAATTG-3':

SEQ ID NO: 32
5'-ATGGAAGCCCCAGCTCAGCTTCTCTTCC-3':

Sense primer set F (a mixture of the following
four types of primers was used)
                                                 SEQ ID NO: 33
5'-ATGAGIMMKTCIMTTCAITTCYTGGG-3':

SEQ ID NO: 34
5'-ATGAKGTHCYCIGCTCAGYTYCTIRG-3':

SEQ ID NO: 35
5'-ATGGTRTCCWCASCTCAGTTCCTTG-3':

SEQ ID NO: 36
5'-ATGTATATATGTTTGTTGTCTATTTCT-3':

Sense primer set G (a mixture of the following
four types of primers was used)
                                                 SEQ ID NO: 37
5'-ATGAAGTTGCCTGTTAGGCTGTTGGTGCT-3':

SEQ ID NO: 38
5'-ATGGATTTWCARGTGCAGATTWTCAGCTT-3':

SEQ ID NO: 39
5'-ATGGTYCTYATVTCCTTGCTGTTCTGG-3':

SEQ ID NO: 40
5'-ATGGTYCTYATVTTRCTGCTGCTATGG-3':

KVL antisense primer
                                                 SEQ ID NO: 41
5'-ACTGGATGGTGGGAAGATGGA-3':
```

B. PCR Primers for Gene Encoding Mouse Heavy Chain Variable Region

Using a primer having homology with a mouse heavy chain signal portion (4 primer sets) at the 5'-terminus and a primer having homology with a KC portion at the 3'-terminus, or using 1 primer set having homology with a FR1 portion at the 5'-terminus and two types of primer sets having homology with the constant region of a mouse heavy chain (IGHC) at the 3'-terminus, mouse immunoglobulin heavy chain variable region DNA was isolated from the cDNA by a polymerase chain reaction. The primer sequences are as follows.

(3) Primers for Cloning of Mouse Heavy Chain Variable Region

VH sense primer (signal portion: 4 primer sets, designed with reference to Table 2.12.2 shown in Current Protocols in Immunology (John Wiley and Sons, Inc.), Unit 2.12 Cloning, Expression, and Modification of Antibody V Regions).

```
                                                 SEQ ID NO: 42
5'-ATGGRATGSAGCTGKGTMATSCTCTT-3' (Degeneracy 32):

SEQ ID NO: 43
5'-ATGRACTTCGGGYTGAGCTKGGTTTT-3' (Degeneracy 8):

SEQ ID NO: 44
5'-ATGGCTGTCTTGGGGCTGCTCTTCT-3':

SEQ ID NO: 45
5'-ATGGRCAGRCTTACWTYY-3' (Degeneracy 32):
```

(4) Primers for Cloning of Mouse Heavy Chain Variable Region

VH sense primer (FR1 portion, designed by modifying the nucleotide sequence of the sense primer described in Tan et al., Journal of Immunology; 169, p. 1119 (2002) (Non Patent Literature 14))

```
                                        SEQ ID NO: 46
5'-SAGGTSMARCTKSAGSAGTCWGG-3' (Degeneracy 256):
```

VH antisense primer (antisense primer common in (3) and (4), which was designed by degenerating the nucleotide sequence such that it can anneal with all isoforms of mouse IgG)

```
                                        SEQ ID NO: 47
   5'-CASCCCCATCDGTCTATCC-3' (Degeneracy 6):
```

Example 9

Determination of Sequences of Variable Regions of Anti-CDH3 Mouse Antibody

The variable region in each of the light chain and heavy chain of an anti-CDH3 mouse monoclonal antibody was amplified by a PCR method employing DNA Engine (Bio-Rad), using the primers shown in Example 8. The amplified DNA fragment was incorporated into a subcloning vector pGEM (Promega), and the nucleotide sequence of the DNA fragment in this vector was then determined using T7, SP6 universal primers.

Among variable regions of the thus sequenced anti-CDH3 mouse antibody (antibody No.: PPAT-076-44M) derived from the mouse hybridoma having Accession No. NITE BP-1536, amino acid sequences corresponding to the CDRs are shown below.

```
         (CDR-H1)
                                  SEQ ID NO: 56
         SLTSYGVH:

(CDR-H2)
                                  SEQ ID NO: 57
         GVIWSGGSTD:

(CDR-H3)
                                  SEQ ID NO: 58
         ARNSNNGFAY:

(CDR-L1)
                                  SEQ ID NO: 59
         NIYSNLA:

(CDR-L2)
                                  SEQ ID NO: 60
         LLVYAAKN:

(CDR-L3)
                                  SEQ ID NO: 61
         QHFYDTPWT:
```

It is to be noted that CDR-H1, H2 and H3 indicate CDR sequences constituting individual antibody heavy chains, and that CDR-L1, L2 and L3 indicate CDR sequences constituting individual antibody light chains.

The nucleotide sequences of both the light chain and heavy chain variable regions of the antibody were searched on the IMGT/V-QUEST. Thereafter, it was confirmed that the antibody gene could be surely cloned.

Example 10

Construction of Transient Expression Vector for Anti-CDH3 Antibody

With regard to genes encoding the V regions of the light chain and heavy chain of the cloned anti-CDH3 mouse antibody, a gene, with which a gene encoding a human Ck region was connected, was designed for a chimeric light chain expression vector, and a gene, with which a gene encoding a human Cgl region was connected, was designed for a chimeric heavy chain expression vector. Then, the thus designed full-length light chain and heavy chain chimeric antibody genes were artificially synthesized by GenScript. To both ends of the gene, restriction enzyme sites (NheI on the 5'-end side, and EcoRI on the 3'-end side) were added.

Thereby, an anti-CDH3 chimeric antibody derived from cells having Accession No. NITE BP-1536 (hereinafter referred to as antibody No. PPAT-076-44C, wherein the antibody has the same heavy chain and light chain variable region sequences as those of PPAT-076-44M) was synthesized, and was then used for chimeric antibody expression vector.

The cells having Accession No. NITE BP-1536 were deposited with the National Institute of Technology and Evaluation (NITE) Patent Microorganisms Depositary (NPMD) (2-5-8, Kazusa Kamatari , Kisarazu-shi, Chiba-ken, Japan, postal code: 292-0818) on Feb. 13, 2013 (the request for transfer to an international deposition: Jan. 24, 2014 under the Budapest Treaty; Receipt No. NITE ABP-1536).

For humanization, a region corresponding to FR is replaced with a human-derived FR sequence, and the artificial synthesis of a full-length antibody was carried out in the same manner as described above. As the amino acid sequence of the region corresponding to FR, human consensus frame sequences (SEQ ID NOs: 62 to 69) or a germline frame sequences (SEQ ID NOs: 72 to 79) were used. The germline frame sequence was designed by inputting the nucleotide sequence of the cloned anti-CDH3 mouse antibody into IMGT/V-QUEST, and then selecting a sequence having the highest similarity. In addition, substitution of the amino acid sequence that corresponded to a reduction in affinity (reshape) was also carried out.

The amino acid sequences of the heavy chain or light chain variable regions of the anti-CDH3 humanized antibodies used herein are shown below.

Antibody Nos. PPAT-076-44Ha, PPAT-076-44Hb, PPAT-076-44Hc, and PPAT-076-44Hd have the same CDR sequence as that of antibody No. PPAT-076-44M.

Antibody Nos. PPAT-076-44Ha and PPAT-076-44Hb comprise a human consensus framework sequence as FR, whereas antibody Nos. PPAT-076-44Hc and PPAT-076-44Hd comprise, as FR, a human germline sequence that is most similar to the original mouse antibody. Moreover, PPAT-076-44Hb and PPAT-076-44Hd comprise substitution of amino acid sequences, as also described below.

Antibody No.; PPAT-076-44Ha (having the heavy chain variable region shown in SEQ
ID NO: 48 and the light chain variable region shown in SEQ ID NO: 49)

SEQ ID NO: 48

EVQLVESGGGLVQPGGSLRLSCAASGFSLTSYGVHWVRQAPGKGLEWVGVIWS

GGSTDYADSVKGRFTISRDNSKNTLYLQMNSLRAEDTAVYYCARNSNNGFAYW

GQGTLVTVSS: (heavy chain variable region)

SEQ ID NO: 49

DIQMTQSPSSLSASVGDRVTITCRASQNIYSNLAWYQQKPGKAPKLLVYAAKNLQ

SGVPSRFSGSGSGTDFTLTISSLQPEDFATYYCQHFYDTPWTFGQGTKVEIK: (light chain variable regions)

Antibody No.; PPAT-076-44Hb (having the heavy chain variable region shown in SEQ
ID NO: 50 and the light chain variable region shown in SEQ ID NO: 51)

SEQ ID NO: 50

EVQLVESGGGLVQPGGSLRLSCAASGFSLTSYGVHWVRQAPGKGLEWVAVIWSG

GSTDYADSVKGRFTISKDNSKNTVYLQMNSLRAEDTAVYYCARNSNNGFAYWG

QGTLVTVSS: (heavy chain variable region)
(G49A, R71K, and L78V are substituted with respect to SEQ ID NO: 48)

SEQ ID NO: 51

DIQMTQSPSSLSASVGDRVTITCRASQNIYSNLAWYQQKPGKAPKLLVYAAKNLA

SGVPSRFSGSGSGTDFTLTISSLQPEDFATYYCQHFYDTPWTEGQGTKVEIK: (light chain variable region)
(Q55A is substituted with respect to SEQ ID NO: 49)

Antibody No.; PPAT-076-44Hc (having the heavy chain variable region shown in SEQ
ID NO: 52 and the light chain variable region shown in SEQ ID NO: 53)

SEQ ID NO: 52

QVQLVESGGGVVQPGRSLRLSCAASGFSLTSYGVHWVRQAPGKGLEWVGVIWS

GGSTDYADSVKGRFTISRDNSKNTLYLQMNSLRAEDTAVYYCARNSNNGFAYW

GQGTLVTVSS: (heavy chain variable region)

SEQ ID NO: 53

DIQLTQSPSSLSASVGDRVTITCRASQNIYSNLAWYQQKPGKAPKLLVYAAKNLE

SGVPSRFSGSGSGTDFTLTISSLQPEDFATYYCQHFYDTPWTFGQGTKVEIK: (light chain variable region)

Antibody No.; PPAT-076-44Hd (having the heavy chain variable region shown in SEQ
ID NO: 54 and the light chain variable region shown in SEQ ID NO: 55)

SEQ ID NO: 54

QVQLVESGGGVVQPGRSLRLSCAASGFSLTSYGVHWVRQAPGKGLEWVGVIWS

GGSTDYADSVKGRFTISKDNSKNTVYLQMNSLRAEDTAVYYCARNSNNGFAYW

GQGTLVTVSS: (heavy chain variable region)
(R71K and L78V are substituted with respect to SEQ ID NO: 52)

SEQ ID NO: 55

DIQLTQSPSSLSASVGDRVTITCRASQNIYSNLAWYQQKPGKAPKLLVYAAKNLA

SGVPSRFSGSGSGTDFTLTISSLQPEDFATYYCQHFYDTPWTFGQGTKVEIK: (light chain variable region)
(E55A is substituted with respect to SEQ ID NO: 53)

After completion of the conversion of the amino acid sequence, with regard to an artificially synthetic gene that had been designed to have a desired sequence, a heavy chain variable region gene was inserted into pCXN3 vector, into which a human IgG1-derived constant region gene had been incorporated, and a light chain variable region gene was inserted into a pCXN3 vector, into which a human κ chain-derived constant region gene had been incorporated, so as to construct an anti-CDH3 humanized antibody (or chimeric antibody) light chain expression vector and an anti-CDH3 humanized antibody (or chimeric antibody) heavy chain expression vector.

Example 11

Transient Expression and Purification of Anti-CDH3 Antibody (1) Transient Expression of Anti-CDH3 Antibody For transient expression of an anti-CDH3 antibody, Free-Style (Life Technologies, Inc.) was used. Floating cells for gene transfer, 293-F (Life Technologies, Inc.), were subcultured on the previous day. On the day of transfection, for the expression of one type of antibody, 400 mL of a cell suspension, which had been adjusted to have a cell density of $1 \times 10^6$ cells/mL, was prepared. A total of 200 μg of a plasmid (100 μg of the antibody heavy chain expression vector and 100 µg of the antibody light chain expression vector) was suspended in OptiPRO SFM, so as to prepare Solution (I). Subsequently, 200 µL of MAX reagent was added to 8 mL of OptiPRO SFM to prepare Solution (II). The Solution (I) was mixed with the Solution (II), and the mixed solution was then left at rest at room temperature for 10 to 20 minutes. A total of 16 mL of this reaction solution was added to 400 mL of 293 expression medium in which 293-F cells were suspended, and the obtained mixture was then cultured for 6 to 7 days at 37° C. in 8% $CO_2$, using a cell culture shaker TAITEC BioShaker BR-43FL. After the culture for 6 to 7 days, a culture supernatant comprising each recombinant antibody was recovered, and it was then subjected to purification.

(2) Purification of Anti-CDH3 Antibody

An IgG antibody protein contained in the culture supernatant was purified by Ab-Capcher ExTra (ProteNova Co., Ltd.) affinity column, using AKTAprime (GE Healthcare Biosciences). The obtained peak fraction was subjected to gel filtration, using Sephacryl S-300 column that had been equilibrated with Dulbecco's PBS used as a solvent, so that it was further purified. The quantity of the purified IgG antibody protein was calculated using an absorption coefficient. The absorption coefficient of the IgG antibody was calculated by subjecting the total amino acid sequence of each antibody to EXPASY ProtParam (http://web.expasy.org/protparam/).

Example 12

Quantification of Antibody by Enzyme-Linked Immunosorbent Assay (ELISA)

A culture supernatant of the transfected CHO cells was measured by ELISA, and it was confirmed that a chimeric antibody had been produced. To detect the chimeric antibody, a plate was coated with goat anti-human IgG (H+L) (which had previously been absorbed against mouse, rabbit, bovine, and mouse IgG) (COSMO BIO: AQI, Cat. No. A-110UD). After blocking, the culture supernatant obtained from CHO cells capable of producing anti-CDH3 chimeric antibody was subjected to serial dilution, and was then added to each well. After the plate had been subjected to incubation and washing, goat anti-human IgG (H+L) (which had previously been absorbed against mouse, rabbit, bovine, and mouse IgG)—HRP (COSMO BIO: AQI, Cat. No. A-110UD) was added to the plate. Following incubation and washing, a TMB coloring solution (AR BROWN CO., LTD., Cat. TM4999) was added to the plate. Incubation was further carried out, the reaction was then terminated, and the absorbance at 450 nm was then measured. Purified human IgG was used as a standard.

Example 13

Binding Activity of Antibody

Antibodies having the sequences shown in Example 10 were evaluated by flow cytometry, in terms of binding activity.

A cell line that would be used as a reaction target (an NCI-H358 cell line that had been confirmed to express CDH3 at a high level) was treated with 2 mM EDTA-PBS, so that the cells were removed from a culture plate, and the obtained cells were then suspended in a FACS solution to a cell density of $1 \times 10^6$ cells/mL. This cell suspension was seeded on a 96-well plate, resulting in an amount of 50 µL/well, and the purified chimeric antibody was then added to the plate to result in a concentration of 10 µg/mL, followed by performing a reaction at 4° C. for 60 minutes. Thereafter, the reaction mixture was washed with a FACS solution (150 µL/well) two times, and 4 µg/ml AlexaFlour488-labeled anti-human IgG/goat F(ab')$_2$ (Invitrogen) was then added to the resultant. The obtained mixture was reacted at 4° C. for 30 minutes. Thereafter, the cells were washed with a FACS solution two times, and was then subjected to flow cytometry.

As a result, the humanized antibodies (PPAT-076-44Ha and PPAT-076-44Hc) were found to have weak reactivity with a CDH3-expressing cancer cell line (NCI-H358). Moreover, the antibodies subjected to the reshape (PPAT-076-44Hb and PPAT-076-44Hd) were found to have strong reactivity with NCI-H358 (FIG. 5A). Furthermore, PPAT-076-44Hb and PPAT-076-44Hd did not react with CHO cells, but these antibodies reacted with CHO cells that were forced to express CDH3, as they reacted with the NCI-H358 cell line (FIGS. 5B and 5C).

As described above, in humanization of a PPAT-076-44M-derived mouse antibody, a sequence that was considered to be a CDR sequence was combined with a consensus or human germline-derived frame sequence, so as to obtain an antibody that exhibited binding activity although the activity was not sufficient. Accordingly, it is assumed that the aforementioned CDR sequence would be a reasonable sequence. Since the binding activity of the humanized antibody derived from PPAT-076-44M is recovered by performing the reshape, the thought that some amino acid residues play an important role for the maintenance of the structure is supported.

Example 14

Synthesis of Drug

Figure 6:
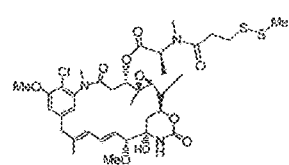
FIG. 6 shows the structure of DM1SMe.

DM1 SMe was prepared as described in U.S. Pat. No. 5,208,020 (Patent Literature 10) and U.S. Pat. No. 6,333,410 B1 (Patent Literature 11). The synthesis of DM1 SMe was outsourced to SYNSTAR JAPAN CO., LTD. The structural formula thereof is shown in FIG. 6.

Example 15

Preparation of Drug-Bound Antibody

1. Reduction Treatment of Bound Drug 0.78 mg of DM1 SMe dissolved in 300 µL of ethanol, 180 µL of a 50 mM potassium phosphate buffer (pH 7.5), and 20 µL of a TCEP Solution (Bond Breaker, Thermo Fisher Scientific K. K.) were mixed with one another, and the obtained mixture was then reacted in a nitrogen atmosphere at room temperature for 30 minutes or longer, so that the drug was reduced.

The reduced drug was purified by HPLC, and the solvent was then distilled away. The residue was dissolved in dimethylacetamide to a concentration of 10 mg/mL.

2. Preparation of Maleimidated Antibody

Sulfo-SMCC (PIERCE) was added to a 1 mg/mL antibody at a molar ratio of 30 : 1 or greater, and the obtained mixture was then reacted at 30° C. for 1 hour.

In order to remove an excessive amount of crosslinker, the reaction product was subjected to a desalination treatment with a desalination column that had been equilibrated with 50 mM potassium phosphate, 50 mM NaCl and 2 mM EDTA (pH 6.5) (ZebaSpinColumn, Thermo Fisher Scientific K. K.).

3. Modification of Antibody with Drug

A 1 mg/mL maleimidated antibody was reacted with a reducing agent that was 1.7-fold larger than the number of the bound maleimide groups in 50 mM potassium phosphate, 50 mM NaCl, and 2 mM EDTA (pH 6.5) at room temperature overnight. Subsequently, an excessive amount of drug was removed from the reaction mixture by gel filtration.

Example 16

Quantification of Amount of Drug Bound to Antibody

The number of drugs bound per antibody was determined by measuring the absorbance at 252 nm and 280 nm The determination was carried out with reference to the methods described in J. Med. Chem., 49, 4392-4408 (2006) (Non Patent Literature 12) and Methods. Mol. Biol. 525, pp. 445-67 (2009) (Non Patent Literature 21), also using the absorption coefficients described in the aforementioned publications ($sAb_{280}$=223,000 $M^{-1}cm^{-1}$, $\epsilon Ab_{252}$=82,510 $M^{-1}cm^{-1}$, $\epsilon DM1_{280}$=5,180 $M^{-1}cm^{-1}$, and $\epsilon DM1_{252}$=26,160 $M^{-1}cm^{-1}$).

Example 17

Cytotoxicity Test

The cytotoxicity and specificity of a drug-bound antibody were evaluated, using a cell growth measurement reagent (Dojindo Laboratories, Cell counting assay kit-8) in which WST-8 was used as a chromogenic substrate.

Specifically, various types of cancer cell lines were allowed to coexist with a humanized antibody drug conjugate in any given amounts, and the obtained mixture was then incubated at 37° C. for 3 days in a 5% $CO_2$ environment. As a medium, a medium predetermined for each cell line, to which FBS had been added, was used. Thereafter, the cell growth measurement reagent was added to the resultant, and the obtained mixture was then left. Subsequently, the absorbance A450/620 was measured. The value of absorbance obtained from a well, to which only the cancer cell line had been added and no antibodies had been added, was set at 100%, and the obtained relative value was indicated as a cell survival percentage.

In FIG. 7A, NCI-H358 was used as a cell line, and as antibody drug conjugates, PPAT-076-44Hb and PPAT-076-44Hd, to each of which a drug was bound, were used. Both of the antibody drug conjugates exhibited cytotoxicity.

In FIG. 7B, HCC1954 was used as a cell line, and as an antibody drug conjugate, PPAT-076-44Hd, to a drug was bound, was used. In FIG. 7C, HCC70 was used as a cell line, and as an antibody drug conjugate, PPAT-076-44Hd, to a drug was bound, was used. Since both of these cell lines express CDH3, the drug conjugate of PPAT-076-44Hd exhibits cytotoxicity.

In FIG. 7D, the cell lines shown in Table 1 below were used, and as an antibody drug conjugate, PPAT-076-44Hd, to a drug was bound, was used. The drug was bound to each antibody by the method described in Example 15. The mRNA signal values of the cell lines shown in Table 1 were average values obtained from the public database (https://cabig-stage.nci.nih.gov/community/caA rray_GSKdata/).

Cell lines having small signal values (NCIH1930 and SW962) were examined as CDH3 expression negative controls. The cell lines expressing CDH3 were inhibited in terms of cell growth, regardless of the type of carcinoma.

All of the drug conjugates used herein had DAR of 3 to 4.

TABLE 1

Cell lines used in the test and diseases of the cell lines

| Name of cell line | Name of disease | Average CDH3 mRNA signal |
|---|---|---|
| NCIH1930 | lung cancer | 9.4 |
| SW962 | vulva carcinoma | 539 |
| Detroit562 | pharynx carcinoma | 1509 |
| NCIH322 | lung cancer | 1568 |
| NCIH358 | lung cancer | 2179 |
| HCC1954 | breast cancer | 2269 |

Example 18

HCC 1954 Cancer-Bearing Animal Tests Using Humanized Antibodies

The tumor-reducing effects of antibody drug conjugates using humanized antibodies (PPAT-076-44Hb and PPAT-076-44Hd) were confirmed using xenograft models, into which the breast cancer cell line HCC1954 had been transplanted.

The drug-to-antibody ratios (DAR) of the two antibody drug conjugates quantified by the method of Example 16 were PPAT-076-44Hb (DAR 3.69) and PPAT-076-44Hd (DAR 3.51).

For cancer bearing, an anti-asialo GM1 antibody (WAKO 014-09801) was first dissolved in 1 mL of Otsuka Distilled Water, and 4 mL of Otsuka Saline was then added to the solution to a total amount of 5 mL. Thereafter, 100 µL of the obtained solution was intraperitoneally administered to each mouse. Subsequently, HCC 1954 was cultured in an RPMI1640 medium that contained 10% FBS, and the culture was then transplanted at an amount of $5 \times 10^6$ cells/mouse into the subcutis of the right abdominal wall of an SCID mouse (female, CLEA Japan, Inc.).

Figure 8:
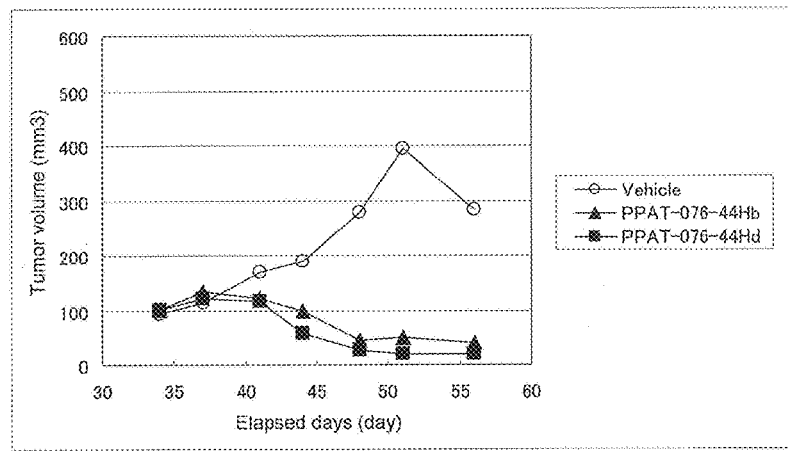
FIG. 8 shows the results of an animal test (HCC 1954 breast cancer model), in which CDH3 antibody drug conjugates (PPAT-076-44Hb and PPAT-076-44Hd, to which a drug is bound) were used.

The test was carried out on 5 mice in each group. The antibody was administered into the caudal vein of each mouse at a dose of 5 mg/kg, once a week, twice in total. The results obtained by measuring the tumor volume are shown in FIG. 8. As shown in FIG. 8, the antibody drug conjugate comprising the humanized antibody exhibited a high anti-tumor effect.

Example 19

HCC70 Cancer-Bearing Animal Test Using Humanized Antibodies (1)

The tumor-reducing effects of antibody drug conjugates comprising the humanized antibody (PPAT-076-44Hb) or the chimeric antibody (PPAT-076-44C) were confirmed using xenograft models, into which the breast cancer cell line HCC70 had been transplanted.

The DARs of the two antibody drug conjugates were PPAT-076-44Hb (DAR 2.90) and PPAT-076-44C (DAR 3.07).

For cancer bearing, an anti-asialo GM1 antibody (WAKO 014-09801) was first dissolved in 1 mL of Otsuka Distilled Water, and 4 mL of Otsuka Saline was then added to the solution to a total amount of 5 mL. Thereafter, 100 μL of the obtained solution was intraperitoneally administered to each mouse. Subsequently, HCC70 was cultured in an RPMI1640 medium that contained 10% FBS, and the culture was then transplanted at an amount of $5 \times 10^6$ cells/mouse into the subcutis of the right abdominal wall of an SCID mouse (female, CLEA Japan, Inc.).

Figure 9:
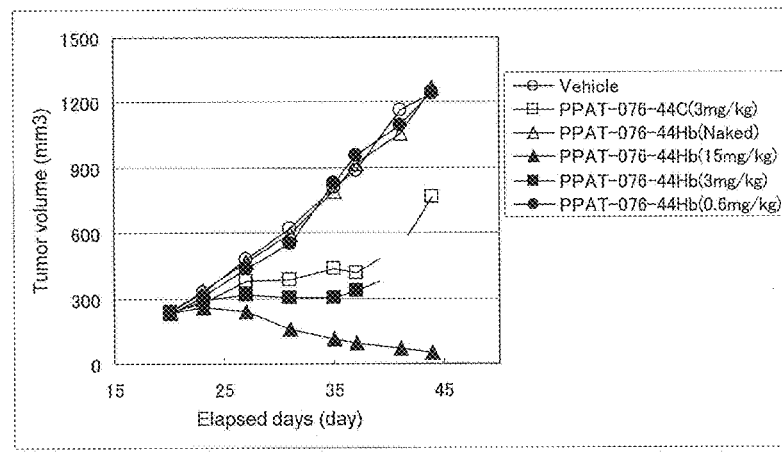
FIG. 9 shows the results of an animal test (HCC70 breast cancer model), in which a CDH3 humanized antibody drug conjugate (PPAT-076-44Hb, to which a drug is bound) was used, wherein the results involve dose dependency and the results of a comparison made with a chimeric antibody drug conjugate (PPAT-076-44C, to which a drug is bound).

The test was carried out on 5 mice in each group. The humanized antibody conjugate was used at a dose of 0.6, 3.0 or 15 mg/kg, the chimeric antibody conjugate was used at a dose of 3.0 mg/kg, and the drug-unbound humanized antibody (Naked) was used at a dose of 15 mg/kg. These antibodies were each administered once a week, twice in total. The results obtained by measuring the tumor volume are shown in FIG. 9. As shown in FIG. 9, the antibody drug conjugate comprising the humanized antibody repeatedly exhibited an antitumor effect that was higher than that of the antibody drug conjugate comprising the chimeric antibody.

Example 20

HCC70 Cancer-Bearing Animal Test Using Humanized Antibody (2)

The tumor-reducing effects of antibody drug conjugates comprising the humanized antibody (PPAT-076-44Hd) or the chimeric antibody (PPAT-076-44C) were confirmed using xenograft models, into which the breast cancer cell line HCC70 had been transplanted.

The cancer bearing was carried out in the same manner as that in Example 19. The humanized antibody conjugate was used at a dose of 0.6, 3.0 or 15 mg/kg, the chimeric antibody conjugate was used at a dose of 3.0 mg/kg, and the drug-unbound humanized antibody (Naked) was used at a dose of 15 mg/kg. These antibodies were each administered via the caudal vein of each mouse, once a week, twice in total. The test was carried out on 5 mice in each group. The DARs of the two antibody drug conjugates were PPAT-076-44C (DAR 3.07) and PPAT-076-44Hd (DAR 2.98).

Figure 10:
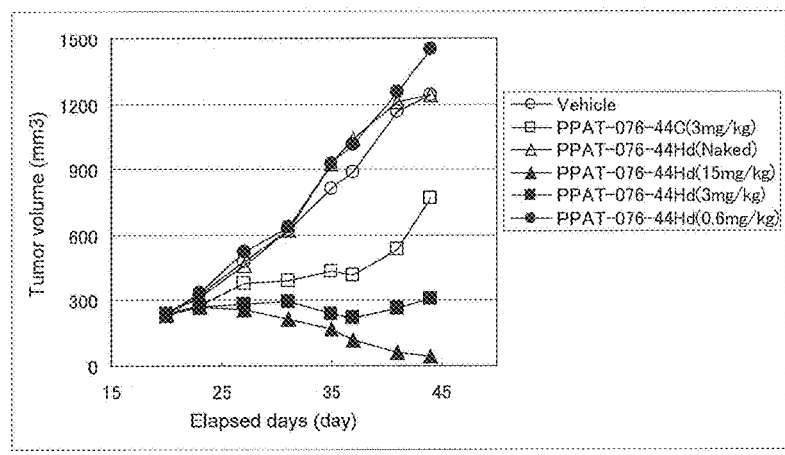
FIG. 10 shows the results of an animal test (HCC70 breast cancer model), in which a CDH3 humanized antibody drug conjugate (PPAT-076-44Hd, to which a drug is bound) was used, wherein the results involve dose dependency and the results of a comparison made with a chimeric antibody drug conjugate (PPAT-076-44C, to which a drug is bound).

The results obtained by measuring the tumor volume are shown in FIG. 10. As shown in FIG. 10, the humanized antibody exhibited a high antitumor effect as a result of the binding of the drug to the antibody, and a dose-dependent antitumor effect could be confirmed. Moreover, as in the case of Example 19, the humanized antibody exhibited again an antitumor effect that was higher than that of the chimeric antibody, when they were administered at the same dose (3.0 mg/kg).

Example 21

OKa-C-1 Cancer-Bearing Animal Test Using Humanized Antibody

Figure 11:
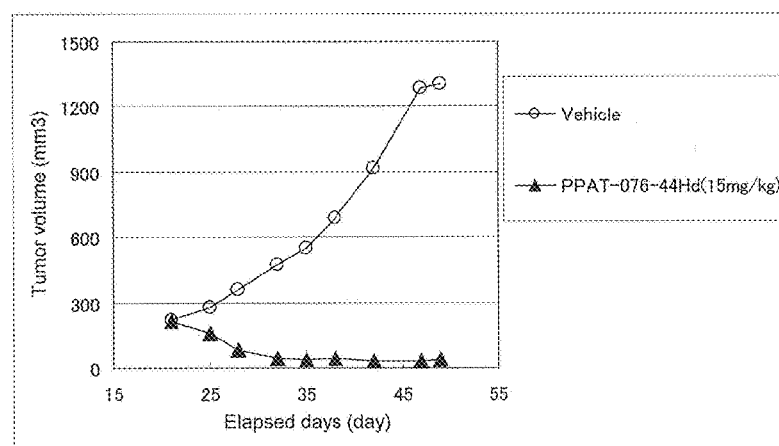
FIG. 11 shows the results of an animal test (OKa-C-1 lung cancer model), in which CDH3 humanized antibody drug conjugate (PPAT-076-44Hd, to which a drug is bound) was used.

The performance of the antibody drug conjugate of the present invention to suppress the growth of a tumor was confirmed using xenograft models, into which the lung cancer cell line OKa-C-1 (National Institute of Biomedical Innovation, JCRB1343) had been transplanted. For cancer bearing, the lung cancer cell line OKa-C-1 was cultured in RPMI1640 medium that contained 10% FBS, and the obtained culture was then transplanted at an amount of $6.5 \times 10^6$ cells/mouse into the subcutis of the right abdominal wall of an SCID mouse (female, CLEA Japan, Inc.). The humanized antibody conjugate was administered to each mouse at a dose of 15 mg/kg, via the caudal vein thereof, once a week, twice in total. The test was carried out on 3 mice in each group. Herein, PPAT-076-44Hd was used as a humanized antibody, and a drug was bound to each antibody by the method described in Example 15. The average drug-to-antibody ratio (DAR) per single antibody molecule was quantified by the method described in Example 16. As a result, the DAR was found to be 3.04. The results obtained by measuring the tumor volume are shown in FIG. 11. As shown in FIG. 11, it was confirmed that the present antibody drug conjugate exhibited a high antitumor effect on lung cancer cell line OKa-C-1, as well as on the breast cancer cell line, as a result of the binding of the drug to the humanized antibody.

Example 22

Expression of CDH3 N-Terminus Partial Length Protein (1) Construction of Expression Vector for CDH3 N-Terminus Partial Length Protein In order to confirm the reactivity of the obtained CDH3 antibody, the N-terminal region of a CDH3 antigen was ligated to the Fc portion of mouse IgG2a, so as to prepare a fusion protein. The cDNA sequence of the fusion protein is as shown in SEQ ID NO: 70, and the amino acid sequence thereof is as shown in SEQ ID NO: 71. As a signal peptide, that of an antibody x chain was used. For subcloning, the restriction enzyme NheI site was added to the 5 prime side, and the EcoRI site was added to the 3 prime side (synthesized by GenScript, U.S.A.). Thereafter, the resultant was incorporated into a mammalian expression vector pCAGGS that had been digested by NheI and EcoRI, or into pCAGGS-DHFR into which a mouse DHFR gene had been incorporated for gene amplification.

(2) Expression and Purification of CDH3 N-Terminus Partial Length Protein

Figure 12:
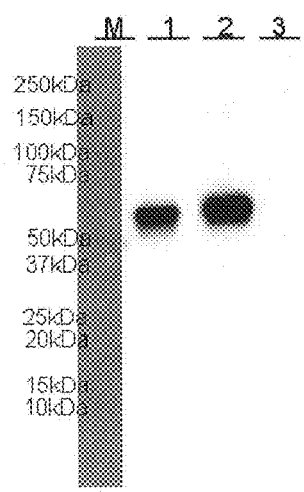
FIG. 12 shows the results regarding the expression of a CDH3 N-terminus partial length protein. A: CBB staining (right lane: expression product, left lane: molecular weight marker). B: Western blotting (M: size marker, 1: commercially available CDH3 antibody (BD BIOSCIENCE), 2: commercially available CDH3 antibody (R & D Systems), and 3: no antibodies).

For transient expression, FreeStyle (Life Technologies, Inc.) was used. As cells for production of the protein, 293-F (Life Technologies, Inc.) was used. As a gene transfer reagent, FreeStyle Max Transfection Reagent (Life Technologies, Inc.) was used. 293F cells, into which a Fe fusion soluble antigen gene had been introduced, were produced by performing a culture for 4 to 7 days, using a TAITEC shaker capable of controlling the $CO_2$ concentration. The produced fusion protein was purified with a Protein A Sepharose (ProteNova Co., Ltd.) column. A view of the transiently expressed and purified antigen which was stained with CBB, is shown in FIG. 12A, and a stained image of a commercially available CDH3 antibody (BD BIOSCIENCE and R & D Systems) used as a primary antibody is shown in FIG. 12B. As a secondary labeled antibody, Anti Mouse IgG F (ab') 2-HRP (goat IgG) (CAPPEL #55553) was used.

Example 23

Solid-Phase ELISA of CDH3 N-Terminus Partial Length Protein

Figure 13:
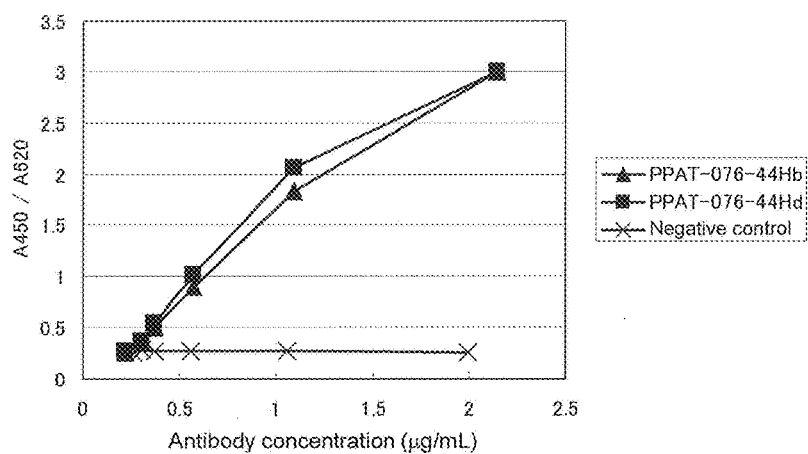
FIG. 13 shows the measurement results of ELISA, in which a CDH3 N-terminus partial length protein was used as a solid phase.

The CDH3 N-terminus partial length protein was diluted with PBS to 2.5 μg/mL, and the obtained solution was then dispensed into a 96-well plate in an amount of 100 μL/well, and it was then left at rest at 4° C. overnight. On the following day, the solution in each well was discarded, and the well was then washed with buffer A (50 mM Tris-HCl/ 150 mM NaCl/1 mM CaCl2/0.05% Tween 20 (pH 7.5)). Subsequently, a dilution series of a test substance (anti- CDH3 antibody) was prepared, and it was then dispensed into the plate in an amount of 100 μL/well, followed by shaking at room temperature for 1 hour. Thereafter, the solution was discarded, and the well was then washed with buffer A. Thereafter, A HRP-labeled antibody (HRP-goat anti human IgG (H+L) (absorbed with mouse, rabbit, bovine IgG) (American Qualex International, cat. A-110PD)) was 10,000 times diluted with buffer A, and it was then dispensed into the plate in an amount of 100 μL/well, followed by shaking at room temperature for 1 hour. Thereafter, the plate was washed with buffer A, and a TMB coloring solution was then added to the plate in an amount of 100 μL/well, followed by leaving it at rest in a dark place for 15 minutes for color development. A stop solution was added to the plate in an amount of 100 μL/well, and the absorbance at 450 nm was then measured using a plate reader. The results are shown in FIG. 13. As test substances, PPAT-076-44Hb and PPAT-076-44Hd were used.

Example 24

Production of Alexa488-Labeled Antibody

An antibody to be used for labeling was substituted with a labeling buffer (50mM NaHCO3, 0.5 M NaCl, pH 8.5). 0.5 μl of 25 mM Alexa488 (1 mg of Alexa488 dissolved in 62.1 μl of DMF, Life Technologies, Inc.) was added to 1 mg of an antibody, and the obtained mixture was then left at rest under light shielding conditions at room temperature for 1 hour. Thereafter, the buffer was exchanged with PBS.

Example 25

Antibody Affinity Comparison Test (1)

The influence of humanization on affinity was confirmed by carrying out a competition test using a flow cytometer (FACS). A test antibody whose dilution series had been prepared, a cell line that expressed CDH3, and a certain amount of Amaxa488-labeled antibody that was competitive with the test antibody were allowed to coexist, and the reaction was then carried out at room temperature for 1 hour. Thereafter, the reaction product was washed with a FACS solution, and FACS measurement was then carried out. From the GEO mean value of each antibody concentration, the inhibitory percentage was calculated, when the GEO mean value of only the competitive antibody was set at 100%, so as to obtain IC50. The obtained IC50 value was defined as an index for affinity.

Figure 14:
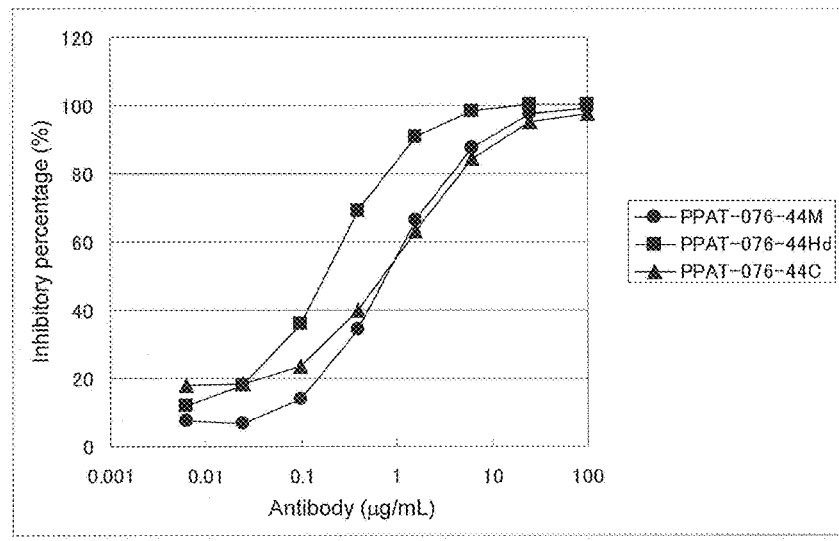
FIG. 14 shows the results obtained by comparing affinity between PPAT-076-44Hd (humanized antibody) and the parent antibodies PPAT-076-44M (mouse antibody) and PPAT-076-44C (chimeric antibody).

As the antibody to be competitive with the test antibody, a mouse antibody purified from a product produced by the cells with No. NITE BP-989, which was labeled by the method described in Example 24, was used. As the test antibodies, PPAT-076-44Hd, PPAT-076-44C, and PPAT-076-44M were used. The results are shown in FIG. 14. The test antibodies were all competitive with the Alexa488-labeled antibody, but the competitive degrees thereof were different. It was demonstrated that the humanized antibody (PPAT-076-44Hd) of the present application had an improved affinity degree, when compared with mouse and chimeric antibodies.

Example 26

Antibody Affinity Comparison Test (2)

The influence of the average drug-to-antibody ratio (DAR) of the drug binding to the humanized antibody of the present invention on affinity was confirmed by the same competition test using FACS as that in Example 25. The antibody drug conjugate was prepared in the range of average DAR of 0 to 8 by the method described in Example 15. The DAR was quantified by the method described in Example 16.

As a cell line, NCI-H358 was used. When PPAT-076-44Hb and PPAT-076-44Hd were measured, a mouse antibody purified from a product produced by the cells with No. NITE BP-989, which was labeled with Alexa488 by the method described in Example 24, was used. By the same FACS competition test as that described in Example 25, each IC50 value was calculated as an index for affinity.

The comparison shown in FIG. 15 (A : PPAT-076-44Hb, B: PPAT-076-44Hd) is indicated with a relative value obtained when the IC50 value of each antibody to which a drug has not been bound is defined as 1. The figure shows that the affinity of both of the humanized antibodies is not decreased by the binding of a drug to the antibodies.

Example 27

Confirmation of CDH3 Expression in Cancer-Bearing Model Lines

In order to confirm the expression of a CDH3 protein in cancer-bearing model lines, cancer-bearing tissue sections were immunostained. Each cell line was transplanted into the subcutis of a mouse, and the mouse was then left for a predetermined days to produce a cancer-bearing mouse. Tumor tissues obtained from such a cancer-bearing mouse were subjected to a deparaffinization treatment, and the resulting tissues were then activated in an autoclave at 121° C. for 15 minutes. Thereafter, endogenous peroxidase was inactivated with methanol containing 0.3% $H_2O_2$, and was then subjected to a blocking treatment with 10% goat serum. The resulting tissues were reacted with the anti-CDH3 antibody 610227 (BD BIOSCIENCE) at 4° C. overnight. After the antibody solution had been washed away, the residue was reacted with Histofine Simple Stain MAX-PO second antibody reagent at room temperature for 1 hour. A Histofine DAB substrate kit was used according to protocols included therewith, so as to carry out DAB color development, and nuclear staining was then carried out using a hematoxylin-eosin solution. The results are shown in FIG. 16 (A : HCC1954, B: HCC70, and C: OKa-C-1). The cell membrane portion of the cancer-bearing tumor was stained with the anti-CDH3 antibody.

The invention claimed is:

1. An anti-CDH3 humanized antibody, which comprises the complementarity determining region sequences of the heavy chain variable region that are shown in SEQ ID NO: 56, SEQ ID NO: 57, and SEQ ID NO: 58, and the complementarity determining region sequences of the light chain variable region that are shown in SEQ ID NO: 59, SEQ ID NO: 60, and SEQ ID NO: 61, and which also comprises the consensus framework residues of human heavy chain subgroup III and the consensus framework residues of human light chain κ subgroup I.

2. An anti-CDH3 humanized antibody, which comprises the complementarity determining region sequences of the heavy chain variable region that are shown in SEQ ID NO: 56, SEQ ID NO: 57, and SEQ ID NO: 58, and the complementarity determining region sequences of the light chain variable region that are shown in SEQ ID NO: 59, SEQ ID NO: 60, and SEQ ID NO: 61, and which also comprises framework region sequences that are obtained from a human germline and are the highest similarity to the mouse sequence.

3. An anti-CDH3 humanized antibody, which shows a sequence homology of at least 90% with the anti-CDH3 humanized antibody according to claim 1, and which is capable of recognizing CDH3.

4. An anti-CDH3 humanized antibody, wherein one to several amino acids in the framework region portions of the antibody according to claim 1 are substituted with other amino acids, and the anti-CDH3 humanized antibody is capable of recognizing CDH3.

5. The anti-CDH3 humanized antibody according to claim 4, wherein the amino acid to be substituted is the amino acid at position 55 (Kabat's numbering) in the light chain variable region.

6. The anti-CDH3 humanized antibody according to claim 4, wherein the amino acids to be substituted are one or more selected from the amino acids at positions 71 and 78 (Kabat's numbering) in the heavy chain variable region.

7. The anti-CDH3 humanized antibody according to claim 1, wherein the amino acid to be substituted is the amino acid at position 49 (Kabat's numbering) in the heavy chain variable region.

8. The anti-CDH3 humanized antibody according to claim 4, wherein the amino acid at position 55 (Kabat's numbering) in the light chain variable region is substituted with alanine.

9. The anti-CDH3 humanized antibody according to claim 4, wherein the amino acid at position 71 (Kabat's numbering) in the heavy chain variable region is substituted with lysine.

10. The anti-CDH3 humanized antibody according to claim 4, wherein the amino acid at position 78 (Kabat's numbering) in the heavy chain variable region is substituted with valine.

11. The anti-CDH3 humanized antibody according to claim 1, wherein the amino acid at position 49 (Kabat's numbering) in the heavy chain variable region is substituted with alanine.

12. The anti-CDH3 humanized antibody according to claim 1, which has one or more substitutions selected from the substitution of the amino acid residue at position 49 (Kabat's numbering) in the heavy chain variable region with alanine, the substitution of the amino acid residue at position 71 (Kabat's numbering) in the heavy chain variable region with lysine, the substitution of the amino acid residue at position 78 (Kabat's numbering) in the heavy chain variable region with valine, and the substitution of the amino acid residue at position 55 (Kabat's numbering) in the light chain variable region with alanine.

13. The anti-CDH3 humanized antibody according to claim 2 which has one or more substitutions selected from the substitution of the amino acid residue at position 71 (Kabat's numbering) in the heavy chain variable region with lysine, the substitution of the amino acid residue at position 78 (Kabat's numbering) in the heavy chain variable region with valine, and the substitution of the amino acid residue at position 55 (Kabat's numbering) in the light chain variable region with alanine.

14. An antibody set forth in any one of the following (1) to (4):
   (1) an anti-CDH3 humanized antibody having the amino acid sequence shown in SEQ ID NO: 48 in the heavy chain variable region and the amino acid sequence shown in SEQ ID NO: 49 in the light chain variable region;
   (2) an anti-CDH3 humanized antibody having the amino acid sequence shown in SEQ ID NO: 50 in the heavy chain variable region and the amino acid sequence shown in SEQ ID NO: 51 in the light chain variable region;
   (3) an anti-CDH3 humanized antibody having the amino acid sequence shown in SEQ ID NO: 52 in the heavy chain variable region and the amino acid sequence shown in SEQ ID NO: 53 in the light chain variable region; and
   (4) an anti-CDH3 humanized antibody having the amino acid sequence shown in SEQ ID NO: 54 in the heavy chain variable region and the amino acid sequence shown in SEQ ID NO: 55 in the light chain variable region.

15. A fragment of the anti-CDH3 humanized antibody according to claim 1, wherein the fragment has an ability to bind to CDH3 and is selected from the following group Fab, Fab', Fab'-SH, Fv, scFv, and (Fab')₂ fragments.

16. The fragment of the anti-CDH3 humanized antibody according to claim 15, which is Fab, F(ab')², or scFv.

17. The anti-CDH3 humanized antibody according to claim 1, wherein the CDH3 is human CDH3.

18. The anti-CDH3 humanized antibody according to claim 1, wherein the CDH3 is an extracellular region shown in SEQ ID NO: 2.

19. An immune complex, in which the anti-CDH3 humanized antibody according to claim 1, or Fab, Fab', Fab'-SH, Fv, scFv, or (Fab')₂ fragment thereof is conjugated to a chemotherapeutic agent or a radioactive material.

20. The immune complex according to claim 19, wherein the chemotherapeutic agent is a cytotoxic substance.

21. The immune complex according to claim 20, wherein the cytotoxic substance is a maytansinoid or a derivative thereof, or an auristatin or a derivative thereof.

22. The immune complex according to claim 20, wherein the cytotoxic substance is a maytansinoid selected from DM1, DM3 and DM4, or a derivative thereof, or an auristatin selected from MMAE and MMAF, or a derivative thereof.

23. The immune complex according to claim 20, wherein an average of one to seven DM1 molecules are bound to a single molecule of the anti-CDH3 humanized antibody, the fragment thereof, or the partial sequence thereof.

24. The immune complex according to claim 19, wherein the anti-CDH3 humanized antibody, the fragment thereof is conjugated to a chemotherapeutic agent via a linker.

25. The immune complex according to claim 19, wherein the anti-CDH3 humanized antibody, the fragment thereof is conjugated to a chemotherapeutic agent, via an intramolecular disulfide bond in the Fc region of the antibody, or by modifying the Fc region of the antibody through a genetic engineering technique.

26. The immune complex according to claim 24, wherein the linker is a divalent reaction crosslinking reagent.

27. The immune complex according to claim 24, wherein the linker is selected from the group consisting of N-succinimidyl 4-(maleimidomethyl)cyclohexanecarboxylate (SMCC), sulfosuccinimidyl-4-(N-maleimidomethyl)-cyclohexane-1-carboxylate (Sulfo-SMCC), N-succinimidyl-4-(N-maleimidomethyl)-cyclohexane-1-carboxy-(6-amidocaproate) (LC-SMCC), κ-maleimidoundecanoic acid N-succinimidyl ester (KMUA), γ-maleimide butyric acid N-succinimidyl ester (GMBS), ε-maleimidocaproic acid N-hydroxysuccinimide ester (EMCS), m-maleimide benzoyl-N-hydroxysuccinimide ester (MBS), N-(α-maleimidoacetoxy)-succinimide ester (AMAS), succinimidyl-6-(β-maleimidopropionamide)hexanoate (SMPH), N-succinimidyl 4-(p-maleimidophenyl)butyrate (SMPB), N-(p-maleimidophenyl)isocyanate (PMPI), N-succinimidyl 4(2-pyridylthio)pentanoate (SPP), N-succinimidyl(4-iodo-acetyl)aminobenzoate (SIAB), 6-maleimidocaproyl (MC), maleimidopropanoyl (MP), p-aminobenzyloxycarbonyl (PAB), and N-succinimidyl (4-(2-pyridylthio)butanoate (SPDB).

28. The immune complex according to claim 24, wherein the linker is cleaved by protease.

29. The immune complex according to claim 24, wherein the linker comprises at least one of valine-citrulline (Val-Cit), alanine-phenylalanine (ala-phe), and para-aminobenzoic acid (PABA).

30. The immune complex according to claim 19, wherein cytotoxic performance is reinforced by humanization of the framework region sequences of antibody variable regions.

31. A medicament for treating a disease that is characterized by overexpression of CDH3, wherein the medicament comprises the immune complex according to claim 19.

32. The medicament according to claim 31, wherein the disease characterized by overexpression of CDH3 is cancer.

33. The medicament according to claim 32, wherein the cancer is selected from among colorectal cancer, non-small-cell lung cancer, breast cancer, cancer of the head and neck, ovarian cancer, lung cancer, invasive bladder cancer, pancreatic cancer, metastatic brain tumor, thyroid cancer, squamous cell carcinoma of the head and neck, squamous cell carcinoma of the esophagus, squamous cell carcinoma of the lung, squamous cell carcinoma of the skin, melanoma, mammary cancer, pulmonary adenocarcinoma, squamous cell carcinoma of the uterine cervix, squamous cell carcinoma of the pancreas, squamous cell carcinoma of the colon, squamous cell carcinoma of the stomach, prostate cancer, osteosarcoma, and soft tissue sarcoma.

34. The medicament according to claim 31, which is used as an antitumor agent.

35. A method for producing an anti-CDH3 humanized antibody which comprises the complementarity determining region sequences of the heavy chain variable region that are shown in SEQ ID NO: 56, SEQ ID NO: 57, and SEQ ID NO: 58, and the complementarity determining region sequences of the light chain variable region that are shown in SEQ ID NO: 59, SEQ ID NO: 60, and SEQ ID NO: 61, and which also comprises the consensus framework residues of human heavy chain subgroup III and the consensus framework residues of human light chain κ subgroup I; wherein said method comprising;
(i) ligating nucleotide sequences encoding complementarity determining region sequences (CDR-H1, H2, and H3) obtained from the heavy chain variable region of an antibody produced by cells having Accession No. NITE BP-1536, to nucleotide sequence encoding the consensus framework residues of human heavy chain subgroup III;
(ii) ligating nucleotide sequences encoding complementarity determining region sequences (CDR-L1, L2, and L3) obtained from the light chain variable region of an antibody produced by cells having Accession No. NITE BP-1536, to nucleotide sequence encoding the consensus framework residues of human light chain κ subgroup I; and
(iii) expressing an antibody encoded by the thus-obtained recombinant DNA.

36. A method for producing an anti-CDH3 humanized antibody which comprises the complementarity determining region sequences of the heavy chain variable region that are shown in SEQ ID NO: 56, SEQ ID NO: 57, and SEQ ID NO: 58, and the complementarity determining region sequences of the light chain variable region that are shown in SEQ ID NO: 59, SEQ ID NO: 60, and SEQ ID NO: 61, and which also comprises framework region sequences that are derived from a human germline having the highest similarity to the mouse sequence;
wherein said method comprising;
(i) ligating nucleotide sequences encoding complementarity determining region sequences (CDR-H1, H2, and H3) obtained from the heavy chain variable region of an antibody produced by cells having Accession No. NITE BP-1536, to nucleotide sequence encoding a framework region sequence that is derived from a human germline having the highest similarity to the mouse sequence;

(ii) ligating nucleotide sequences encoding complementarity determining region sequences (CDR-L1, L2, and L3) obtained from the light chain variable region of an antibody produced by cells having Accession No. NITE BP-1536, to nucleotide sequence encoding a framework region sequence that is derived from a human germline having the highest similarity to the mouse sequence; and expressing an antibody encoded by the thus-obtained recombinant DNA.

* * * * *

SEQUENCE LISTING

```
<160> NUMBER OF SEQ ID NOS: 79

<210> SEQ ID NO 1
<211> LENGTH: 2490
<212> TYPE: DNA
```

```
<213> ORGANISM: human
<220> FEATURE:
<221> NAME/KEY: CDS
<222> LOCATION: (1)..(2490)

<400> SEQUENCE: 1 atg ggg ctc cct cgt gga cct ctc gcg tct ctc ctc ctt ctc cag gtt      48
Met Gly Leu Pro Arg Gly Pro Leu Ala Ser Leu Leu Leu Leu Gln Val
1               5                   10                  15 tgc tgg ctg cag tgc gcg gcc tcc gag ccg tgc cgg gcg gtc ttc agg      96
Cys Trp Leu Gln Cys Ala Ala Ser Glu Pro Cys Arg Ala Val Phe Arg
                20                  25                  30 gag gct gaa gtg acc ttg gag gcg gga ggc gcg gag cag gag ccc ggc     144
Glu Ala Glu Val Thr Leu Glu Ala Gly Gly Ala Glu Gln Glu Pro Gly
            35                  40                  45 cag gcg ctg ggg aaa gta ttc atg ggc tgc cct ggg caa gag cca gct     192
Gln Ala Leu Gly Lys Val Phe Met Gly Cys Pro Gly Gln Glu Pro Ala
        50                  55                  60 ctg ttt agc act gat aat gat gac ttc act gtg cgg aat ggc gag aca     240
Leu Phe Ser Thr Asp Asn Asp Asp Phe Thr Val Arg Asn Gly Glu Thr
65                  70                  75                  80 gtc cag gaa aga agg tca ctg aag gaa agg aat cca ttg aag atc ttc     288
Val Gln Glu Arg Arg Ser Leu Lys Glu Arg Asn Pro Leu Lys Ile Phe
                85                  90                  95 cca tcc aaa cgt atc tta cga aga cac aag aga gat tgg gtg gtt gct     336
Pro Ser Lys Arg Ile Leu Arg Arg His Lys Arg Asp Trp Val Val Ala
                100                 105                 110 cca ata tct gtc cct gaa aat ggc aag ggt ccc ttc ccc cag aga ctg     384
Pro Ile Ser Val Pro Glu Asn Gly Lys Gly Pro Phe Pro Gln Arg Leu
            115                 120                 125 aat cag ctc aag tct aat aaa gat aga gac acc aag att ttc tac agc     432
Asn Gln Leu Lys Ser Asn Lys Asp Arg Asp Thr Lys Ile Phe Tyr Ser
        130                 135                 140 atc acg ggg ccg ggg gca gac agc ccc cct gag ggt gtc ttc gct gta     480
Ile Thr Gly Pro Gly Ala Asp Ser Pro Pro Glu Gly Val Phe Ala Val
145                 150                 155                 160 gag aag gag aca ggc tgg ttg ttg ttg aat aag cca ctg gac cgg gag     528
Glu Lys Glu Thr Gly Trp Leu Leu Leu Asn Lys Pro Leu Asp Arg Glu
                165                 170                 175 gag att gcc aag tat gag ctc ttt ggc cac gct gtg tca gag aat ggt     576
Glu Ile Ala Lys Tyr Glu Leu Phe Gly His Ala Val Ser Glu Asn Gly
            180                 185                 190 gcc tca gtg gag gac ccc atg aac atc tcc atc atc gtg acc gac cag     624
Ala Ser Val Glu Asp Pro Met Asn Ile Ser Ile Ile Val Thr Asp Gln
        195                 200                 205 aat gac cac aag ccc aag ttt acc cag gac acc ttc cga ggg agt gtc     672
Asn Asp His Lys Pro Lys Phe Thr Gln Asp Thr Phe Arg Gly Ser Val
    210                 215                 220 tta gag gga gtc cta cca ggt act tct gtg atg cag gtg aca gcc acg     720
Leu Glu Gly Val Leu Pro Gly Thr Ser Val Met Gln Val Thr Ala Thr
225                 230                 235                 240 gat gag gat gat gcc atc tac acc tac aat ggg gtg gtt gct tac tcc     768
Asp Glu Asp Asp Ala Ile Tyr Thr Tyr Asn Gly Val Val Ala Tyr Ser
                245                 250                 255 atc cat agc caa gaa cca aag gac cca cac gac ctc atg ttc acc att     816
Ile His Ser Gln Glu Pro Lys Asp Pro His Asp Leu Met Phe Thr Ile
            260                 265                 270 cac cgg agc aca ggc acc atc agc gtc atc tcc agt ggc ctg gac cgg     864
His Arg Ser Thr Gly Thr Ile Ser Val Ile Ser Ser Gly Leu Asp Arg
        275                 280                 285
```

-continued

| | | |
|---|---|---|
| gaa aaa gtc cct gag tac aca ctg acc atc cag gcc aca gac atg gat<br>Glu Lys Val Pro Glu Tyr Thr Leu Thr Ile Gln Ala Thr Asp Met Asp<br>290                        295                      300 | 912 | |
| ggg gac ggc tcc acc acc acg gca gtg gca gta gtg gag atc ctt gat<br>Gly Asp Gly Ser Thr Thr Thr Ala Val Ala Val Val Glu Ile Leu Asp<br>305                        310                      315              320 | 960 | |
| gcc aat gac aat gct ccc atg ttt gac ccc cag aag tac gag gcc cat<br>Ala Asn Asp Asn Ala Pro Met Phe Asp Pro Gln Lys Tyr Glu Ala His<br>                    325                      330                      335 | 1008 | |
| gtg cct gag aat gca gtg ggc cat gag gtg cag agg ctg acg gtc act<br>Val Pro Glu Asn Ala Val Gly His Glu Val Gln Arg Leu Thr Val Thr<br>                  340                      345                      350 | 1056 | |
| gat ctg gac gcc ccc aac tca cca gcg tgg cgt gcc acc tac ctt atc<br>Asp Leu Asp Ala Pro Asn Ser Pro Ala Trp Arg Ala Thr Tyr Leu Ile<br>              355                      360                      365 | 1104 | |
| atg ggc ggt gac gac ggg gac cat ttt acc atc acc acc cac cct gag<br>Met Gly Gly Asp Asp Gly Asp His Phe Thr Ile Thr Thr His Pro Glu<br>370                        375                      380 | 1152 | |
| agc aac cag ggc atc ctg aca acc agg aag ggt ttg gat ttt gag gcc<br>Ser Asn Gln Gly Ile Leu Thr Thr Arg Lys Gly Leu Asp Phe Glu Ala<br>385                        390                      395              400 | 1200 | |
| aaa aac cag cac acc ctg tac gtt gaa gtg acc aac gag gcc cct ttt<br>Lys Asn Gln His Thr Leu Tyr Val Glu Val Thr Asn Glu Ala Pro Phe<br>                  405                      410                      415 | 1248 | |
| gtg ctg aag ctc cca acc tcc aca gcc acc ata gtg gtc cac gtg gag<br>Val Leu Lys Leu Pro Thr Ser Thr Ala Thr Ile Val Val His Val Glu<br>                  420                      425                      430 | 1296 | |
| gat gtg aat gag gca cct gtg ttt gtc cca ccc tcc aaa gtc gtt gag<br>Asp Val Asn Glu Ala Pro Val Phe Val Pro Pro Ser Lys Val Val Glu<br>              435                      440                      445 | 1344 | |
| gtc cag gag ggc atc ccc act ggg gag cct gtg tgt gtc tac act gca<br>Val Gln Glu Gly Ile Pro Thr Gly Glu Pro Val Cys Val Tyr Thr Ala<br>450                        455                      460 | 1392 | |
| gaa gac cct gac aag gag aat caa aag atc agc tac cgc atc ctg aga<br>Glu Asp Pro Asp Lys Glu Asn Gln Lys Ile Ser Tyr Arg Ile Leu Arg<br>465                        470                      475              480 | 1440 | |
| gac cca gca ggg tgg cta gcc atg gac cca gac agt ggg cag gtc aca<br>Asp Pro Ala Gly Trp Leu Ala Met Asp Pro Asp Ser Gly Gln Val Thr<br>                  485                      490                      495 | 1488 | |
| gct gtg ggc acc ctc gac cgt gag gat gag cag ttt gtg agg aac aac<br>Ala Val Gly Thr Leu Asp Arg Glu Asp Glu Gln Phe Val Arg Asn Asn<br>              500                      505                      510 | 1536 | |
| atc tat gaa gtc atg gtc ttg gcc atg gac aat gga agc cct ccc acc<br>Ile Tyr Glu Val Met Val Leu Ala Met Asp Asn Gly Ser Pro Pro Thr<br>                  515                      520                      525 | 1584 | |
| act ggc acg gga acc ctt ctg cta aca ctg att gat gtc aat gac cat<br>Thr Gly Thr Gly Thr Leu Leu Leu Thr Leu Ile Asp Val Asn Asp His<br>530                        535                      540 | 1632 | |
| ggc cca gtc cct gag ccc cgt cag atc acc atc tgc aac caa agc cct<br>Gly Pro Val Pro Glu Pro Arg Gln Ile Thr Ile Cys Asn Gln Ser Pro<br>545                        550                      555              560 | 1680 | |
| gtg cgc cag gtg ctg aac atc acg gac aag gac ctg tct ccc cac acc<br>Val Arg Gln Val Leu Asn Ile Thr Asp Lys Asp Leu Ser Pro His Thr<br>                  565                      570                      575 | 1728 | |
| tcc cct ttc cag gcc cag ctc aca gat gac tca gac atc tac tgg acg<br>Ser Pro Phe Gln Ala Gln Leu Thr Asp Asp Ser Asp Ile Tyr Trp Thr<br>              580                      585                      590 | 1776 | |
| gca gag gtc aac gag gaa ggt gac aca gtg gtc ttg tcc ctg aag aag<br>Ala Glu Val Asn Glu Glu Gly Asp Thr Val Val Leu Ser Leu Lys Lys<br>595                        600                      605 | 1824 | |

```
ttc ctg aag cag gat aca tat gac gtg cac ctt tct ctg tct gac cat    1872
Phe Leu Lys Gln Asp Thr Tyr Asp Val His Leu Ser Leu Ser Asp His
    610                 615                 620 ggc aac aaa gag cag ctg acg gtg atc agg gcc act gtg tgc gac tgc    1920
Gly Asn Lys Glu Gln Leu Thr Val Ile Arg Ala Thr Val Cys Asp Cys
625                 630                 635                 640 cat ggc cat gtc gaa acc tgc cct gga ccc tgg aag gga ggt ttc atc    1968
His Gly His Val Glu Thr Cys Pro Gly Pro Trp Lys Gly Gly Phe Ile
                645                 650                 655 ctc cct gtg ctg ggg gct gtc ctg gct ctg ctg ttc ctg ctg gtg        2016
Leu Pro Val Leu Gly Ala Val Leu Ala Leu Leu Phe Leu Leu Leu Val
            660                 665                 670 ctg ctt ttg ttg gtg aga aag aag cgg aag atc aag gag ccc ctc cta    2064
Leu Leu Leu Leu Val Arg Lys Lys Arg Lys Ile Lys Glu Pro Leu Leu
        675                 680                 685 ctc cca gaa gat gac acc cgt gac aac gtc ttc tac tat ggc gaa gag    2112
Leu Pro Glu Asp Asp Thr Arg Asp Asn Val Phe Tyr Tyr Gly Glu Glu
    690                 695                 700 ggg ggt ggc gaa gag gac cag gac tat gac atc acc cag ctc cac cga    2160
Gly Gly Gly Glu Glu Asp Gln Asp Tyr Asp Ile Thr Gln Leu His Arg
705                 710                 715                 720 ggt ctg gag gcc agg ccg gag gtg gtt ctc cgc aat gac gtg gca cca    2208
Gly Leu Glu Ala Arg Pro Glu Val Val Leu Arg Asn Asp Val Ala Pro
                725                 730                 735 acc atc atc ccg aca ccc atg tac cgt cct cgg cca gcc aac cca gat    2256
Thr Ile Ile Pro Thr Pro Met Tyr Arg Pro Arg Pro Ala Asn Pro Asp
            740                 745                 750 gaa atc ggc aac ttt ata att gag aac ctg aag gcg gct aac aca gac    2304
Glu Ile Gly Asn Phe Ile Ile Glu Asn Leu Lys Ala Ala Asn Thr Asp
        755                 760                 765 ccc aca gcc ccg ccc tac gac acc ctc ttg gtg ttc gac tat gag ggc    2352
Pro Thr Ala Pro Pro Tyr Asp Thr Leu Leu Val Phe Asp Tyr Glu Gly
    770                 775                 780 agc ggc tcc gac gcc gcg tcc ctg agc tcc ctc acc tcc tcc gcc tcc    2400
Ser Gly Ser Asp Ala Ala Ser Leu Ser Ser Leu Thr Ser Ser Ala Ser
785                 790                 795                 800 gac caa gac caa gat tac gat tat ctg aac gag tgg ggc agc cgc ttc    2448
Asp Gln Asp Gln Asp Tyr Asp Tyr Leu Asn Glu Trp Gly Ser Arg Phe
                805                 810                 815 aag aag ctg gca gac atg tac ggt ggc ggg gag gac gac tag            2490
Lys Lys Leu Ala Asp Met Tyr Gly Gly Gly Glu Asp Asp
            820                 825

<210> SEQ ID NO 2
<211> LENGTH: 829
<212> TYPE: PRT
<213> ORGANISM: human

<400> SEQUENCE: 2

Met Gly Leu Pro Arg Gly Pro Leu Ala Ser Leu Leu Leu Leu Gln Val
1               5                   10                  15

Cys Trp Leu Gln Cys Ala Ala Ser Glu Pro Cys Arg Ala Val Phe Arg
            20                  25                  30

Glu Ala Glu Val Thr Leu Glu Ala Gly Gly Ala Glu Gln Glu Pro Gly
        35                  40                  45

Gln Ala Leu Gly Lys Val Phe Met Gly Cys Pro Gly Gln Glu Pro Ala
    50                  55                  60

Leu Phe Ser Thr Asp Asn Asp Asp Phe Thr Val Arg Asn Gly Glu Thr
65                  70                  75                  80
```

```
Val Gln Glu Arg Arg Ser Leu Lys Glu Arg Asn Pro Leu Lys Ile Phe
                    85                  90                  95

Pro Ser Lys Arg Ile Leu Arg Arg His Lys Arg Asp Trp Val Val Ala
            100                 105                 110

Pro Ile Ser Val Pro Glu Asn Gly Lys Gly Pro Phe Pro Gln Arg Leu
        115                 120                 125

Asn Gln Leu Lys Ser Asn Lys Asp Arg Asp Thr Lys Ile Phe Tyr Ser
130                 135                 140

Ile Thr Gly Pro Gly Ala Asp Ser Pro Pro Glu Gly Val Phe Ala Val
145                 150                 155                 160

Glu Lys Glu Thr Gly Trp Leu Leu Leu Asn Lys Pro Leu Asp Arg Glu
                165                 170                 175

Glu Ile Ala Lys Tyr Glu Leu Phe Gly His Ala Val Ser Glu Asn Gly
            180                 185                 190

Ala Ser Val Glu Asp Pro Met Asn Ile Ser Ile Val Thr Asp Gln
        195                 200                 205

Asn Asp His Lys Pro Lys Phe Thr Gln Asp Thr Phe Arg Gly Ser Val
210                 215                 220

Leu Glu Gly Val Leu Pro Gly Thr Ser Val Met Gln Val Thr Ala Thr
225                 230                 235                 240

Asp Glu Asp Asp Ala Ile Tyr Thr Tyr Asn Gly Val Val Ala Tyr Ser
                245                 250                 255

Ile His Ser Gln Glu Pro Lys Asp Pro His Asp Leu Met Phe Thr Ile
            260                 265                 270

His Arg Ser Thr Gly Thr Ile Ser Val Ile Ser Ser Gly Leu Asp Arg
        275                 280                 285

Glu Lys Val Pro Glu Tyr Thr Leu Thr Ile Gln Ala Thr Asp Met Asp
290                 295                 300

Gly Asp Gly Ser Thr Thr Thr Ala Val Ala Val Val Glu Ile Leu Asp
305                 310                 315                 320

Ala Asn Asp Asn Ala Pro Met Phe Asp Pro Gln Lys Tyr Glu Ala His
                325                 330                 335

Val Pro Glu Asn Ala Val Gly His Glu Val Gln Arg Leu Thr Val Thr
            340                 345                 350

Asp Leu Asp Ala Pro Asn Ser Pro Ala Trp Arg Ala Thr Tyr Leu Ile
        355                 360                 365

Met Gly Gly Asp Asp Gly Asp His Phe Thr Ile Thr Thr His Pro Glu
370                 375                 380

Ser Asn Gln Gly Ile Leu Thr Thr Arg Lys Gly Leu Asp Phe Glu Ala
385                 390                 395                 400

Lys Asn Gln His Thr Leu Tyr Val Glu Val Thr Asn Glu Ala Pro Phe
                405                 410                 415

Val Leu Lys Leu Pro Thr Ser Thr Ala Thr Ile Val Val His Val Glu
            420                 425                 430

Asp Val Asn Glu Ala Pro Val Phe Val Pro Pro Ser Lys Val Val Glu
        435                 440                 445

Val Gln Glu Gly Ile Pro Thr Gly Glu Pro Val Cys Val Tyr Thr Ala
450                 455                 460

Glu Asp Pro Asp Lys Glu Asn Gln Lys Ile Ser Tyr Arg Ile Leu Arg
465                 470                 475                 480

Asp Pro Ala Gly Trp Leu Ala Met Asp Pro Asp Ser Gly Gln Val Thr
                485                 490                 495
```

```
Ala Val Gly Thr Leu Asp Arg Glu Asp Gln Phe Val Arg Asn Asn
                500                 505                 510

Ile Tyr Glu Val Met Val Leu Ala Met Asp Asn Gly Ser Pro Pro Thr
            515                 520                 525

Thr Gly Thr Gly Thr Leu Leu Leu Thr Leu Ile Asp Val Asn Asp His
        530                 535                 540

Gly Pro Val Pro Glu Pro Arg Gln Ile Thr Ile Cys Asn Gln Ser Pro
545                 550                 555                 560

Val Arg Gln Val Leu Asn Ile Thr Asp Lys Asp Leu Ser Pro His Thr
                565                 570                 575

Ser Pro Phe Gln Ala Gln Leu Thr Asp Asp Ser Asp Ile Tyr Trp Thr
            580                 585                 590

Ala Glu Val Asn Glu Glu Gly Asp Thr Val Val Leu Ser Leu Lys Lys
        595                 600                 605

Phe Leu Lys Gln Asp Thr Tyr Asp Val His Leu Ser Leu Ser Asp His
610                 615                 620

Gly Asn Lys Glu Gln Leu Thr Val Ile Arg Ala Thr Val Cys Asp Cys
625                 630                 635                 640

His Gly His Val Glu Thr Cys Pro Gly Pro Trp Lys Gly Gly Phe Ile
                645                 650                 655

Leu Pro Val Leu Gly Ala Val Leu Ala Leu Leu Phe Leu Leu Leu Val
            660                 665                 670

Leu Leu Leu Leu Val Arg Lys Lys Arg Lys Ile Lys Glu Pro Leu Leu
        675                 680                 685

Leu Pro Glu Asp Asp Thr Arg Asp Asn Val Phe Tyr Tyr Gly Glu Glu
690                 695                 700

Gly Gly Gly Glu Glu Asp Gln Asp Tyr Asp Ile Thr Gln Leu His Arg
705                 710                 715                 720

Gly Leu Glu Ala Arg Pro Glu Val Val Leu Arg Asn Asp Val Ala Pro
                725                 730                 735

Thr Ile Ile Pro Thr Pro Met Tyr Arg Pro Arg Pro Ala Asn Pro Asp
            740                 745                 750

Glu Ile Gly Asn Phe Ile Ile Glu Asn Leu Lys Ala Ala Asn Thr Asp
        755                 760                 765

Pro Thr Ala Pro Pro Tyr Asp Thr Leu Leu Val Phe Asp Tyr Glu Gly
770                 775                 780

Ser Gly Ser Asp Ala Ala Ser Leu Ser Ser Leu Thr Ser Ser Ala Ser
785                 790                 795                 800

Asp Gln Asp Gln Asp Tyr Asp Tyr Leu Asn Glu Trp Gly Ser Arg Phe
                805                 810                 815

Lys Lys Leu Ala Asp Met Tyr Gly Gly Gly Glu Asp Asp
            820                 825

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 3
cgcggtacca tggggctccc tcgt                                          24

<210> SEQ ID NO 4
<211> LENGTH: 29
```

```
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 4
ccgtctagat aacctcccttt ccagggtcc                                       29

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 5
gayatccagc tgactcagcc                                                  20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 6
gayattgttc tcwcccagtc                                                  20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 7
gayattgtgm tmactcagtc                                                  20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 8
gayattgtgy tracacagtc                                                  20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 9
gayattgtra tgacmcagtc                                                  20

<210> SEQ ID NO 10
<211> LENGTH: 20
<212> TYPE: DNA
```

<213> ORGANISM: Artificial Sequence
<220> FEATURE:
<223> OTHER INFORMATION: Description of Artificial Sequence: Synthetic
      DNA

<400> SEQUENCE: 10
gayattmaga tramccagtc                                          20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 11
gayattcaga tgaydcagtc                                          20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 12
gayatycaga tgacacagac                                          20

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 13
gayattgttc tcawccagtc                                          20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 14
gayattgwgc tsacccaatc                                          20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 15
gayattstra tgacccartc                                          20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 16
gayrttktga tgacccarac                                              20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 17
gayattgtga tgacbcagkc                                              20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 18
gayattgtga taacycagga                                              20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 19
gayattgtga tgacccagwt                                              20

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 20
gayattgtga tgacacaacc                                              20

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic DNA

<400> SEQUENCE: 21
gayattttgc tgactcagtc                                              20

<210> SEQ ID NO 22
<211> LENGTH: 21
<212> TYPE: DNA
<213> ORGANISM: Artificial Sequence
<220> FEATURE:

```
<223> OTHER INFORMATION: Description of Artificial Sequence: Synthetic
      DNA

<400> SEQUENCE: 22
ggsaccaarc tggaaatmaa a                                              21

<210> SEQ ID NO 23
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 23
gggacaaagt tggaaataaa a                                              21

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 24
gggaccaagc tggagctgaa a                                              21

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 25
atgragwcac akwcycaggt cttt                                           24

<210> SEQ ID NO 26
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 26
atggagacag acacactcct gctat                                          25

<210> SEQ ID NO 27
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 27
atggagwcag acacactsct gytatgggt                                      29

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
```

DNA
<220> FEATURE:
<221> NAME/KEY: misc_feature
<222> LOCATION: (27)..(27)
<223> OTHER INFORMATION: n is inosine

<400> SEQUENCE: 28
atgaggrccc ctgctcagwt tyttggnwtc tt                                     32

<210> SEQ ID NO 29
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 29
atgggcwtca agatgragtc acakwyycwg g                                      31

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 30
atgagtgtgc ycactcaggt cctggsgtt                                         29

<210> SEQ ID NO 31
<211> LENGTH: 31
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 31
atgtggggay cgktttyamm cttttcaatt g                                      31

<210> SEQ ID NO 32
<211> LENGTH: 28
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 32
atggaagccc cagctcagct tctcttcc                                          28

<210> SEQ ID NO 33
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (6)..(6)
<223> OTHER INFORMATION: n is inosine
<220> FEATURE:
<221> NAME/KEY: misc_feature
<222> LOCATION: (12)..(12)
<223> OTHER INFORMATION: n is inosine
<220> FEATURE:

<221> NAME/KEY: misc_feature
<222> LOCATION: (18)..(18)
<223> OTHER INFORMATION: n is inosine

<400> SEQUENCE: 33
atgagnmmkt cnmttcantt cytggg        26

<210> SEQ ID NO 34
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA
<220> FEATURE:
<221> NAME/KEY: misc_feature
<222> LOCATION: (12)..(12)
<223> OTHER INFORMATION: n is inosine
<220> FEATURE:
<221> NAME/KEY: misc_feature
<222> LOCATION: (24)..(24)
<223> OTHER INFORMATION: n is inosine

<400> SEQUENCE: 34
atgakgthcy cngctcagyt yctnrg        26

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 35
atggtrtccw casctcagtt ccttg         25

<210> SEQ ID NO 36
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 36
atgtatatat gtttgttgtc tatttct       27

<210> SEQ ID NO 37
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 37
atgaagttgc ctgttaggct gttggtgct     29

<210> SEQ ID NO 38
<211> LENGTH: 29
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 38

```
atggatttwc argtgcagat twtcagctt                                              29
```

<210> SEQ ID NO 39
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 39

```
atggtyctya tvtccttgct gttctgg                                                27
```

<210> SEQ ID NO 40
<211> LENGTH: 27
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 40

```
atggtyctya tvttrctgct gctatgg                                                27
```

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 41

```
actggatggt gggaagatgg a                                                      21
```

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 42

```
atggratgsa gctgkgtmat sctctt                                                 26
```

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 43

```
atgracttcg ggytgagctk ggtttt                                                 26
```

<210> SEQ ID NO 44
<211> LENGTH: 25
<212> TYPE: DNA
<213> ORGANISM: Artificial Sequence
<220> FEATURE:
<223> OTHER INFORMATION: Description of Artificial Sequence: Synthetic
      DNA

<400> SEQUENCE: 44

```
atggctgtct tggggctgct cttct                                                  25
```

<210> SEQ ID NO 45
<211> LENGTH: 18
<212> TYPE: DNA
<213> ORGANISM: Artificial Sequence
<220> FEATURE:
<223> OTHER INFORMATION: Description of Artificial Sequence: Synthetic DNA

<400> SEQUENCE: 45
atggrcagrc ttacwtyy                                                18

<210> SEQ ID NO 46
<211> LENGTH: 23
<212> TYPE: DNA
<213> ORGANISM: Artificial Sequence
<220> FEATURE:
<223> OTHER INFORMATION: Description of Artificial Sequence: Synthetic DNA

<400> SEQUENCE: 46
saggtsmarc tksagsagtc wgg                                          23

<210> SEQ ID NO 47
<211> LENGTH: 19
<212> TYPE: DNA
<213> ORGANISM: Artificial Sequence
<220> FEATURE:
<223> OTHER INFORMATION: Description of Artificial Sequence: Synthetic DNA

<400> SEQUENCE: 47 cascccatc dgtctatcc                                                19

<210> SEQ ID NO 48
<211> LENGTH: 116
<212> TYPE: PRT
<213> ORGANISM: Artificial Sequence
<220> FEATURE:
<223> OTHER INFORMATION: Synthetic antibody from mouse/human

<400> SEQUENCE: 48

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ser Tyr
            20                  25                  30

Gly Val His Trp Val Arg Gln Ala Pro Gly Lys Gly Leu Glu Trp Val
        35                  40                  45

Gly Val Ile Trp Ser Gly Gly Ser Thr Asp Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Ser Asn Asn Gly Phe Ala Tyr Trp Gly Gln Gly Thr Leu Val
            100                 105                 110

Thr Val Ser Ser
        115

<210> SEQ ID NO 49
<211> LENGTH: 107
<212> TYPE: PRT
<213> ORGANISM: Artificial Sequence
<220> FEATURE:
<223> OTHER INFORMATION: Synthetic antibody from mouse/human

<400> SEQUENCE: 49

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Tyr Ser Asn
            20                  25                  30

Leu Ala Trp Tyr Gln Gln Lys Pro Gly Lys Ala Pro Lys Leu Leu Val
        35                  40                  45

Tyr Ala Ala Lys Asn Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Asp Thr Pro Trp
                85                  90                  95

Thr Phe Gly Gln Gly Thr Lys Val Glu Ile Lys
            100                 105

<210> SEQ ID NO 50
<211> LENGTH: 116
<212> TYPE: PRT
<213> ORGANISM: Artificial Sequence
<220> FEATURE:
<223> OTHER INFORMATION: Synthetic antibody from mouse/human

<400> SEQUENCE: 50

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ser Tyr
            20                  25                  30

Gly Val His Trp Val Arg Gln Ala Pro Gly Lys Gly Leu Glu Trp Val
        35                  40                  45

Ala Val Ile Trp Ser Gly Gly Ser Thr Asp Tyr Ala Asp Ser Val Lys
    50                  55                  60

Gly Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asn Ser Asn Asn Gly Phe Ala Tyr Trp Gly Gln Gly Thr Leu Val
            100                 105                 110

Thr Val Ser Ser
        115

<210> SEQ ID NO 51
<211> LENGTH: 107
<212> TYPE: PRT
<213> ORGANISM: Artificial Sequence
<220> FEATURE:
<223> OTHER INFORMATION: Synthetic antibody from mouse/human

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Tyr Ser Asn
            20                  25                  30

Leu Ala Trp Tyr Gln Gln Lys Pro Gly Lys Ala Pro Lys Leu Leu Val
        35                  40                  45

Tyr Ala Ala Lys Asn Leu Ala Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Asp Thr Pro Trp
                85                  90                  95

Thr Phe Gly Gln Gly Thr Lys Val Glu Ile Lys
            100                 105

<210> SEQ ID NO 52
<211> LENGTH: 116
<212> TYPE: PRT
<213> ORGANISM: Artificial Sequence
<220> FEATURE:
<223> OTHER INFORMATION: Synthetic antibody from mouse/human

<400> SEQUENCE: 52

Gln Val Gln Leu Val Glu Ser Gly Gly Val Val Gln Pro Gly Arg
1               5                   10                  15

Ser Leu Arg Leu Ser Cys Ala Ala Ser Gly Phe Ser Leu Thr Ser Tyr
                20                  25                  30

Gly Val His Trp Val Arg Gln Ala Pro Gly Lys Gly Leu Glu Trp Val
            35                  40                  45

Gly Val Ile Trp Ser Gly Gly Ser Thr Asp Tyr Ala Asp Ser Val Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Asn Ser Asn Asn Gly Phe Ala Tyr Trp Gly Gln Gly Thr Leu Val
            100                 105                 110

Thr Val Ser Ser
        115

<210> SEQ ID NO 53
<211> LENGTH: 107
<212> TYPE: PRT
<213> ORGANISM: Artificial Sequence
<220> FEATURE:
<223> OTHER INFORMATION: Synthetic antibody from mouse/human

<400> SEQUENCE: 53

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asn Ile Tyr Ser Asn
                20                  25                  30

Leu Ala Trp Tyr Gln Gln Lys Pro Gly Lys Ala Pro Lys Leu Leu Val
            35                  40                  45

Tyr Ala Ala Lys Asn Leu Glu Ser Gly Val Pro Ser Arg Phe Ser Gly
            50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Asp Thr Pro Trp
                85                  90                  95

Thr Phe Gly Gln Gly Thr Lys Val Glu Ile Lys
            100                 105

<210> SEQ ID NO 54

```
<211> LENGTH: 116
<212> TYPE: PRT
<213> ORGANISM: Artificial Sequence
<220> FEATURE:
<223> OTHER INFORMATION: Synthetic antibody from mouse/human

<400> SEQUENCE: 54

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ser Leu Thr Ser Tyr
            20                  25                  30

Gly Val His Trp Val Arg Gln Ala Pro Gly Lys Gly Leu Glu Trp Val
        35                  40                  45

Gly Val Ile Trp Ser Gly Gly Ser Thr Asp Tyr Ala Asp Ser Val Lys
    50                  55                  60

Gly Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asn Ser Asn Asn Gly Phe Ala Tyr Trp Gly Gln Gly Thr Leu Val
            100                 105                 110

Thr Val Ser Ser
        115

<210> SEQ ID NO 55
<211> LENGTH: 107
<212> TYPE: PRT
<213> ORGANISM: Artificial Sequence
<220> FEATURE:
<223> OTHER INFORMATION: Synthetic antibody from mouse/human

<400> SEQUENCE: 55

Asp Ile Gln Leu Thr Gln Ser Pro Ser Ser Leu Ser Ala Ser Val Gly
1               5                   10                  15

Asp Arg Val Thr Ile Thr Cys Arg Ala Ser Gln Asn Ile Tyr Ser Asn
            20                  25                  30

Leu Ala Trp Tyr Gln Gln Lys Pro Gly Lys Ala Pro Lys Leu Leu Val
        35                  40                  45

Tyr Ala Ala Lys Asn Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln His Phe Tyr Asp Thr Pro Trp
                85                  90                  95

Thr Phe Gly Gln Gly Thr Lys Val Glu Ile Lys
            100                 105

<210> SEQ ID NO 56
<211> LENGTH: 8
<212> TYPE: PRT
<213> ORGANISM: mouse

<400> SEQUENCE: 56

Ser Leu Thr Ser Tyr Gly Val His
1               5

<210> SEQ ID NO 57
<211> LENGTH: 10
<212> TYPE: PRT
<213> ORGANISM: mouse
```

```
<400> SEQUENCE: 57

Gly Val Ile Trp Ser Gly Gly Ser Thr Asp
1               5                   10

<210> SEQ ID NO 58
<211> LENGTH: 10
<212> TYPE: PRT
<213> ORGANISM: mouse

<400> SEQUENCE: 58

Ala Arg Asn Ser Asn Asn Gly Phe Ala Tyr
1               5                   10

<210> SEQ ID NO 59
<211> LENGTH: 7
<212> TYPE: PRT
<213> ORGANISM: mouse

<400> SEQUENCE: 59

Asn Ile Tyr Ser Asn Leu Ala
1               5

<210> SEQ ID NO 60
<211> LENGTH: 8
<212> TYPE: PRT
<213> ORGANISM: mouse

<400> SEQUENCE: 60

Leu Leu Val Tyr Ala Ala Lys Asn
1               5

<210> SEQ ID NO 61
<211> LENGTH: 9
<212> TYPE: PRT
<213> ORGANISM: mouse

<400> SEQUENCE: 61

Gln His Phe Tyr Asp Thr Pro Trp Thr
1               5

<210> SEQ ID NO 62
<211> LENGTH: 27
<212> TYPE: PRT
<213> ORGANISM: human

<400> SEQUENCE: 62

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln
            20                  25

<210> SEQ ID NO 63
<211> LENGTH: 11
<212> TYPE: PRT
<213> ORGANISM: human

<400> SEQUENCE: 63

Trp Tyr Gln Gln Lys Pro Gly Lys Ala Pro Lys
1               5                   10

<210> SEQ ID NO 64
<211> LENGTH: 35
<212> TYPE: PRT
```

<213> ORGANISM: human

<400> SEQUENCE: 64

Leu Gln Ser Gly Val Pro Ser Arg Phe Ser Gly Ser Gly Ser Gly Thr
1               5                   10                  15
Asp Phe Thr Leu Thr Ile Ser Ser Leu Gln Pro Glu Asp Phe Ala Thr
            20                  25                  30
Tyr Tyr Cys
        35

<210> SEQ ID NO 65
<211> LENGTH: 10
<212> TYPE: PRT
<213> ORGANISM: human

<400> SEQUENCE: 65

Phe Gly Gln Gly Thr Lys Val Glu Ile Lys
1               5                   10

<210> SEQ ID NO 66
<211> LENGTH: 27
<212> TYPE: PRT
<213> ORGANISM: human

<400> SEQUENCE: 66

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe
            20                  25

<210> SEQ ID NO 67
<211> LENGTH: 13
<212> TYPE: PRT
<213> ORGANISM: human

<400> SEQUENCE: 67

Trp Val Arg Gln Ala Pro Gly Lys Gly Leu Glu Trp Val
1               5                   10

<210> SEQ ID NO 68
<211> LENGTH: 37
<212> TYPE: PRT
<213> ORGANISM: human

<400> SEQUENCE: 68

Tyr Ala Asp Ser Val Lys Gly Arg Phe Thr Ile Ser Arg Asp Asn Ser
1               5                   10                  15
Lys Asn Thr Leu Tyr Leu Gln Met Asn Ser Leu Arg Ala Glu Asp Thr
            20                  25                  30
Ala Val Tyr Tyr Cys
        35

<210> SEQ ID NO 69
<211> LENGTH: 11
<212> TYPE: PRT
<213> ORGANISM: human

<400> SEQUENCE: 69

Trp Gly Gln Gly Thr Leu Val Thr Val Ser Ser
1               5                   10

<210> SEQ ID NO 70

<211> LENGTH: 1362
<212> TYPE: DNA
<213> ORGANISM: Artificial Sequence
<220> FEATURE:
<223> OTHER INFORMATION: Synthetic antibody from human/mouse
<220> FEATURE:
<221> NAME/KEY: CDS
<222> LOCATION: (1)..(1362)

<400> SEQUENCE: 70

| | | | | | | | | | | | | | | | | |
|---|---|---|---|---|---|---|---|---|---|---|---|---|---|---|---|---|
| gat | tgg | gtc | gtc | gct | cct | atc | tcc | gtc | cct | gag | aat | ggg | aag | ggt | ccc | 48 |
| Asp | Trp | Val | Val | Ala | Pro | Ile | Ser | Val | Pro | Glu | Asn | Gly | Lys | Gly | Pro | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ttc | cct | cag | cga | ctg | aac | cag | ctg | aag | agt | aac | aag | gac | cgt | gat | act | 96 |
| Phe | Pro | Gln | Arg | Leu | Asn | Gln | Leu | Lys | Ser | Asn | Lys | Asp | Arg | Asp | Thr | |
| | | | 20 | | | | | 25 | | | | | 30 | | | |

| | | | | | | | | | | | | | | | | |
|---|---|---|---|---|---|---|---|---|---|---|---|---|---|---|---|---|
| aag | atc | ttc | tac | tca | att | acc | gga | cca | gga | gca | gat | tcc | cca | cct | gaa | 144 |
| Lys | Ile | Phe | Tyr | Ser | Ile | Thr | Gly | Pro | Gly | Ala | Asp | Ser | Pro | Pro | Glu | |
| | | | 35 | | | | | 40 | | | | | 45 | | | |

| | | | | | | | | | | | | | | | | |
|---|---|---|---|---|---|---|---|---|---|---|---|---|---|---|---|---|
| ggg | gtc | ttt | gcc | gtg | gaa | aag | gag | act | ggt | tgg | ctg | ctg | ctg | aac | aaa | 192 |
| Gly | Val | Phe | Ala | Val | Glu | Lys | Glu | Thr | Gly | Trp | Leu | Leu | Leu | Asn | Lys | |
| | 50 | | | | | 55 | | | | | 60 | | | | | |

| | | | | | | | | | | | | | | | | |
|---|---|---|---|---|---|---|---|---|---|---|---|---|---|---|---|---|
| cct | ctg | gac | cga | gag | gaa | atc | gcc | aag | tat | gag | ctg | ttt | ggg | cac | gct | 240 |
| Pro | Leu | Asp | Arg | Glu | Glu | Ile | Ala | Lys | Tyr | Glu | Leu | Phe | Gly | His | Ala | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| gtc | agc | gaa | aac | ggt | gca | tct | gtg | gag | gat | ccc | atg | aat | att | agc | atc | 288 |
| Val | Ser | Glu | Asn | Gly | Ala | Ser | Val | Glu | Asp | Pro | Met | Asn | Ile | Ser | Ile | |
| | | | | 85 | | | | | 90 | | | | | 95 | | |

| | | | | | | | | | | | | | | | | |
|---|---|---|---|---|---|---|---|---|---|---|---|---|---|---|---|---|
| att | gtg | acc | gat | cag | aac | gac | cat | aag | cct | aaa | ttc | aca | cag | gac | act | 336 |
| Ile | Val | Thr | Asp | Gln | Asn | Asp | His | Lys | Pro | Lys | Phe | Thr | Gln | Asp | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| ttt | cgg | ggc | agt | gtc | ctg | gaa | ggc | gtg | ctg | cca | gga | act | tca | gtc | atg | 384 |
| Phe | Arg | Gly | Ser | Val | Leu | Glu | Gly | Val | Leu | Pro | Gly | Thr | Ser | Val | Met | |
| | | 115 | | | | | 120 | | | | | 125 | | | | |

| | | | | | | | | | | | | | | | | |
|---|---|---|---|---|---|---|---|---|---|---|---|---|---|---|---|---|
| cag | gtg | acc | gcc | aca | gat | gag | gac | gat | gct | atc | tac | acc | tat | aac | ggc | 432 |
| Gln | Val | Thr | Ala | Thr | Asp | Glu | Asp | Asp | Ala | Ile | Tyr | Thr | Tyr | Asn | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| gtg | gtc | gct | tac | tct | att | cac | agt | cag | gag | ccc | aag | gat | cct | cac | gac | 480 |
| Val | Val | Ala | Tyr | Ser | Ile | His | Ser | Gln | Glu | Pro | Lys | Asp | Pro | His | Asp | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| ctg | atg | ttc | aca | atc | cat | aga | agt | act | ggc | acc | atc | tca | gtg | att | tcc | 528 |
| Leu | Met | Phe | Thr | Ile | His | Arg | Ser | Thr | Gly | Thr | Ile | Ser | Val | Ile | Ser | |
| | | | 165 | | | | | 170 | | | | | 175 | | | |

| | | | | | | | | | | | | | | | | |
|---|---|---|---|---|---|---|---|---|---|---|---|---|---|---|---|---|
| agc | gga | ctg | gac | cgc | gaa | aag | gtg | ccc | gag | tat | aca | ctg | act | att | cag | 576 |
| Ser | Gly | Leu | Asp | Arg | Glu | Lys | Val | Pro | Glu | Tyr | Thr | Leu | Thr | Ile | Gln | |
| | | 180 | | | | | 185 | | | | | 190 | | | | |

| | | | | | | | | | | | | | | | | |
|---|---|---|---|---|---|---|---|---|---|---|---|---|---|---|---|---|
| gca | act | gac | atg | gat | ggg | gac | ggt | agc | acc | aca | act | gcc | gtg | gct | gtg | 624 |
| Ala | Thr | Asp | Met | Asp | Gly | Asp | Gly | Ser | Thr | Thr | Thr | Ala | Val | Ala | Val | |
| | 195 | | | | | 200 | | | | | 205 | | | | | |

| | | | | | | | | | | | | | | | | |
|---|---|---|---|---|---|---|---|---|---|---|---|---|---|---|---|---|
| gtc | gag | atc | ctg | gat | gca | aac | gac | aat | gcc | cca | atg | ttt | ccc | agg | ggc | 672 |
| Val | Glu | Ile | Leu | Asp | Ala | Asn | Asp | Asn | Ala | Pro | Met | Phe | Pro | Arg | Gly | |
| | 210 | | | | | 215 | | | | | 220 | | | | | |

| | | | | | | | | | | | | | | | | |
|---|---|---|---|---|---|---|---|---|---|---|---|---|---|---|---|---|
| cct | acc | att | aag | cca | agc | cca | ccc | tgc | aaa | tgt | cca | gct | ccc | aat | ctg | 720 |
| Pro | Thr | Ile | Lys | Pro | Ser | Pro | Pro | Cys | Lys | Cys | Pro | Ala | Pro | Asn | Leu | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| ctg | ggc | gga | ccc | tct | gtg | ttc | atc | ttt | cct | cca | aag | atc | aag | gat | gtg | 768 |
| Leu | Gly | Gly | Pro | Ser | Val | Phe | Ile | Phe | Pro | Pro | Lys | Ile | Lys | Asp | Val | |
| | | | 245 | | | | | 250 | | | | | 255 | | | |

| | | | | | | | | | | | | | | | | |
|---|---|---|---|---|---|---|---|---|---|---|---|---|---|---|---|---|
| ctg | atg | atc | tct | ctg | agt | cct | att | gtc | aca | tgc | gtg | gtc | gtg | gat | gtg | 816 |
| Leu | Met | Ile | Ser | Leu | Ser | Pro | Ile | Val | Thr | Cys | Val | Val | Val | Asp | Val | |
| | | | 260 | | | | | 265 | | | | | 270 | | | |

| | | | | | | | | | | | | | | | | |
|---|---|---|---|---|---|---|---|---|---|---|---|---|---|---|---|---|
| agc | gag | gac | gat | cca | gac | gtc | cag | atc | tct | tgg | ttc | gtg | aac | aat | gtc | 864 |
| Ser | Glu | Asp | Asp | Pro | Asp | Val | Gln | Ile | Ser | Trp | Phe | Val | Asn | Asn | Val | |
| | | 275 | | | | 280 | | | | | 285 | | | | | |
| gaa | gtg | cac | acc | gcc | cag | acc | cag | aca | cat | agg | gag | gac | tac | aac | tct | 912 |
| Glu | Val | His | Thr | Ala | Gln | Thr | Gln | Thr | His | Arg | Glu | Asp | Tyr | Asn | Ser | |
| | 290 | | | | | 295 | | | | | 300 | | | | | |
| aca | ctg | cgg | gtc | gtg | agt | gct | ctg | cca | atc | cag | cat | cag | gat | tgg | atg | 960 |
| Thr | Leu | Arg | Val | Val | Ser | Ala | Leu | Pro | Ile | Gln | His | Gln | Asp | Trp | Met | |
| 305 | | | | | 310 | | | | | 315 | | | | | 320 | |
| tct | ggg | aaa | gag | ttc | aag | tgc | aaa | gtg | aac | aat | aag | gac | ctg | cct | gct | 1008 |
| Ser | Gly | Lys | Glu | Phe | Lys | Cys | Lys | Val | Asn | Asn | Lys | Asp | Leu | Pro | Ala | |
| | | | | 325 | | | | | 330 | | | | | 335 | | |
| cca | atc | gag | agg | aca | att | tcc | aag | cca | aaa | gga | agc | gtg | cgg | gca | cca | 1056 |
| Pro | Ile | Glu | Arg | Thr | Ile | Ser | Lys | Pro | Lys | Gly | Ser | Val | Arg | Ala | Pro | |
| | | 340 | | | | | 345 | | | | | 350 | | | | |
| cag | gtc | tat | gtg | ctg | cca | cct | cca | gag | gaa | gag | atg | aca | aag | aaa | cag | 1104 |
| Gln | Val | Tyr | Val | Leu | Pro | Pro | Pro | Glu | Glu | Glu | Met | Thr | Lys | Lys | Gln | |
| | | 355 | | | | | 360 | | | | | 365 | | | | |
| gtc | act | ctg | acc | tgt | atg | gtg | act | gat | ttc | atg | cct | gaa | gac | atc | tac | 1152 |
| Val | Thr | Leu | Thr | Cys | Met | Val | Thr | Asp | Phe | Met | Pro | Glu | Asp | Ile | Tyr | |
| 370 | | | | | 375 | | | | | 380 | | | | | | |
| gtg | gag | tgg | acc | aac | aat | ggc | aag | aca | gaa | ctg | aac | tat | aaa | aat | acc | 1200 |
| Val | Glu | Trp | Thr | Asn | Asn | Gly | Lys | Thr | Glu | Leu | Asn | Tyr | Lys | Asn | Thr | |
| 385 | | | | | 390 | | | | | 395 | | | | | 400 | |
| gag | cca | gtg | ctg | gat | tca | gac | gga | tcc | tac | ttt | atg | tat | tcc | aag | ctg | 1248 |
| Glu | Pro | Val | Leu | Asp | Ser | Asp | Gly | Ser | Tyr | Phe | Met | Tyr | Ser | Lys | Leu | |
| | | | | 405 | | | | | 410 | | | | | 415 | | |
| aga | gtc | gaa | aag | aaa | aac | tgg | gtg | gag | cgc | aat | tca | tac | tcc | tgt | agc | 1296 |
| Arg | Val | Glu | Lys | Lys | Asn | Trp | Val | Glu | Arg | Asn | Ser | Tyr | Ser | Cys | Ser | |
| | | 420 | | | | | 425 | | | | | 430 | | | | |
| gtc | gtg | cac | gag | ggt | ctg | cac | aac | cac | cac | aca | aca | aag | agt | ttc | tca | 1344 |
| Val | Val | His | Glu | Gly | Leu | His | Asn | His | His | Thr | Thr | Lys | Ser | Phe | Ser | |
| | | 435 | | | | | 440 | | | | | 445 | | | | |
| cgg | agt | ctg | ggt | aaa | taa | | | | | | | | | | | 1362 |
| Arg | Ser | Leu | Gly | Lys | | | | | | | | | | | | |
| | | 450 | | | | | | | | | | | | | | |

<210> SEQ ID NO 71
<211> LENGTH: 453
<212> TYPE: PRT
<213> ORGANISM: Artificial Sequence
<220> FEATURE:
<223> OTHER INFORMATION: Synthetic Construct

<400> SEQUENCE: 71

```
Asp Trp Val Val Ala Pro Ile Ser Val Pro Glu Asn Gly Lys Gly Pro
 1               5                  10                  15

Phe Pro Gln Arg Leu Asn Gln Leu Lys Ser Asn Lys Asp Arg Asp Thr
                20                  25                  30

Lys Ile Phe Tyr Ser Ile Thr Gly Pro Gly Ala Asp Ser Pro Pro Glu
            35                  40                  45

Gly Val Phe Ala Val Glu Lys Glu Thr Gly Trp Leu Leu Leu Asn Lys
        50                  55                  60

Pro Leu Asp Arg Glu Glu Ile Ala Lys Tyr Glu Leu Phe Gly His Ala
65                  70                  75                  80

Val Ser Glu Asn Gly Ala Ser Val Glu Asp Pro Met Asn Ile Ser Ile
                85                  90                  95

Ile Val Thr Asp Gln Asn Asp His Lys Pro Lys Phe Thr Gln Asp Thr
            100                 105                 110
```

```
Phe Arg Gly Ser Val Leu Glu Gly Val Leu Pro Gly Thr Ser Val Met
            115                 120                 125

Gln Val Thr Ala Thr Asp Glu Asp Ala Ile Tyr Thr Tyr Asn Gly
    130                 135                 140

Val Val Ala Tyr Ser Ile His Ser Gln Glu Pro Lys Asp Pro His Asp
145                 150                 155                 160

Leu Met Phe Thr Ile His Arg Ser Thr Gly Thr Ile Ser Val Ile Ser
                165                 170                 175

Ser Gly Leu Asp Arg Glu Lys Val Pro Glu Tyr Thr Leu Thr Ile Gln
            180                 185                 190

Ala Thr Asp Met Asp Gly Asp Gly Ser Thr Thr Thr Ala Val Ala Val
        195                 200                 205

Val Glu Ile Leu Asp Ala Asn Asp Asn Ala Pro Met Phe Pro Arg Gly
    210                 215                 220

Pro Thr Ile Lys Pro Ser Pro Cys Lys Cys Pro Ala Pro Asn Leu
225                 230                 235                 240

Leu Gly Gly Pro Ser Val Phe Ile Phe Pro Pro Lys Ile Lys Asp Val
                245                 250                 255

Leu Met Ile Ser Leu Ser Pro Ile Val Thr Cys Val Val Asp Val
        260                 265                 270

Ser Glu Asp Asp Pro Asp Val Gln Ile Ser Trp Phe Val Asn Asn Val
275                 280                 285

Glu Val His Thr Ala Gln Thr Gln Thr His Arg Glu Asp Tyr Asn Ser
    290                 295                 300

Thr Leu Arg Val Val Ser Ala Leu Pro Ile Gln His Gln Asp Trp Met
305                 310                 315                 320

Ser Gly Lys Glu Phe Lys Cys Lys Val Asn Asn Lys Asp Leu Pro Ala
                325                 330                 335

Pro Ile Glu Arg Thr Ile Ser Lys Pro Lys Gly Ser Val Arg Ala Pro
            340                 345                 350

Gln Val Tyr Val Leu Pro Pro Pro Glu Glu Met Thr Lys Lys Gln
        355                 360                 365

Val Thr Leu Thr Cys Met Val Thr Asp Phe Met Pro Glu Asp Ile Tyr
    370                 375                 380

Val Glu Trp Thr Asn Asn Gly Lys Thr Glu Leu Asn Tyr Lys Asn Thr
385                 390                 395                 400

Glu Pro Val Leu Asp Ser Asp Gly Ser Tyr Phe Met Tyr Ser Lys Leu
                405                 410                 415

Arg Val Glu Lys Lys Asn Trp Val Glu Arg Asn Ser Tyr Ser Cys Ser
            420                 425                 430

Val Val His Glu Gly Leu His Asn His His Thr Thr Lys Ser Phe Ser
        435                 440                 445

Arg Ser Leu Gly Lys
    450

<210> SEQ ID NO 72
<211> LENGTH: 27
<212> TYPE: PRT
<213> ORGANISM: human

<400> SEQUENCE: 72

Asp Ile Gln Leu Thr Gln Ser Pro Ser Leu Ser Ala Ser Val Gly
1               5                   10                  15

Asp Arg Val Thr Ile Thr Cys Arg Ala Ser Gln
            20                  25
```

<210> SEQ ID NO 73
<211> LENGTH: 11
<212> TYPE: PRT
<213> ORGANISM: human

<400> SEQUENCE: 73

Trp Tyr Gln Gln Lys Pro Gly Lys Ala Pro Lys
1               5                   10

<210> SEQ ID NO 74
<211> LENGTH: 35
<212> TYPE: PRT
<213> ORGANISM: human

<400> SEQUENCE: 74

Leu Glu Ser Gly Val Pro Ser Arg Phe Ser Gly Ser Gly Ser Gly Thr
1               5                   10                  15

Asp Phe Thr Leu Thr Ile Ser Ser Leu Gln Pro Glu Asp Phe Ala Thr
            20                  25                  30

Tyr Tyr Cys
        35

<210> SEQ ID NO 75
<211> LENGTH: 10
<212> TYPE: PRT
<213> ORGANISM: human

<400> SEQUENCE: 75

Phe Gly Gln Gly Thr Lys Val Glu Ile Lys
1               5                   10

<210> SEQ ID NO 76
<211> LENGTH: 27
<212> TYPE: PRT
<213> ORGANISM: human

<400> SEQUENCE: 76

Gln Val Gln Leu Val Glu Ser Gly Gly Gly Val Val Gln Pro Gly Arg
1               5                   10                  15

Ser Leu Arg Leu Ser Cys Ala Ala Ser Gly Phe
            20                  25

<210> SEQ ID NO 77
<211> LENGTH: 13
<212> TYPE: PRT
<213> ORGANISM: human

<400> SEQUENCE: 77

Trp Val Arg Gln Ala Pro Gly Lys Gly Leu Glu Trp Val
1               5                   10

<210> SEQ ID NO 78
<211> LENGTH: 37
<212> TYPE: PRT
<213> ORGANISM: human

<400> SEQUENCE: 78

Tyr Ala Asp Ser Val Lys Gly Arg Phe Thr Ile Ser Arg Asp Asn Ser
1               5                   10                  15

Lys Asn Thr Leu Tyr Leu Gln Met Asn Ser Leu Arg Ala Glu Asp Thr
            20                  25                  30

```
Ala Val Tyr Tyr Cys
        35

<210> SEQ ID NO 79
<211> LENGTH: 11
<212> TYPE: PRT
<213> ORGANISM: human

<400> SEQUENCE: 79

Trp Gly Gln Gly Thr Leu Val Thr Val Ser Ser
1               5                   10
```